United States Patent
Namsaraev

(10) Patent No.: US 8,828,688 B2
(45) Date of Patent: Sep. 9, 2014

(54) MULTIPLEX AMPLIFICATION METHODS

(75) Inventor: Eugeni A. Namsaraev, Palo Alto, CA (US)

(73) Assignee: Affymetrix, Inc., Santa Clara, CA (US)

( * ) Notice: Subject to any disclaimer, the term of this patent is extended or adjusted under 35 U.S.C. 154(b) by 320 days.

(21) Appl. No.: 13/118,363

(22) Filed: May 27, 2011

(65) Prior Publication Data

US 2011/0294689 A1 Dec. 1, 2011

Related U.S. Application Data

(60) Provisional application No. 61/394,004, filed on May 27, 2010.

(51) Int. Cl.
*C40B 50/06* (2006.01)
*C12Q 1/68* (2006.01)

(52) U.S. Cl.
CPC .............. *C12Q 1/6853* (2013.01); *C12Q 1/686* (2013.01); *C12Q 1/6816* (2013.01)
USPC ............................................ 435/91.2; 506/26

(58) Field of Classification Search
None
See application file for complete search history.

(56) References Cited

U.S. PATENT DOCUMENTS

| | | | |
|---|---|---|---|
| 4,883,750 A | 11/1989 | Whiteley et al. |
| 5,168,038 A | 12/1992 | Tecott et al. |
| 5,185,243 A | 2/1993 | Ullman et al. |
| 5,210,015 A | 5/1993 | Gelfand et al. |
| 5,426,180 A | 6/1995 | Kool |
| 5,476,930 A | 12/1995 | Letsinger et al. |
| 5,573,907 A | 11/1996 | Carrino et al. |
| 5,593,826 A | 1/1997 | Fung et al. |
| 5,635,400 A | 6/1997 | Brenner |
| 5,679,524 A | 10/1997 | Nikiforov et al. |
| 5,871,921 A | 2/1999 | Landegren et al. |
| 5,925,517 A | 7/1999 | Tyagi et al. |
| 5,981,176 A | 11/1999 | Wallace |
| 6,150,516 A | 11/2000 | Brenner et al. |
| 6,174,670 B1 | 1/2001 | Wittwer et al. |
| 6,569,627 B2 | 5/2003 | Wittwer et al. |
| 6,713,294 B1 | 3/2004 | Krokan et al. |

(Continued)

FOREIGN PATENT DOCUMENTS

| | | |
|---|---|---|
| EP | 0320308 | 6/1989 |
| EP | 0336731 | 10/1989 |

(Continued)

OTHER PUBLICATIONS

Barringer et al, Blunt-end and Single-strand ligations by *Escherichia coli* ligase: influence on an in vitro samplification scheme, Gene 89 *1990) 117-122.

(Continued)

*Primary Examiner* — Stephanie K Mummert
(74) *Attorney, Agent, or Firm* — Banner & Witcoff, Ltd.

(57) ABSTRACT

Compositions and methods for amplifying selected polynucleotides, including DNA and RNA, particularly in multiplex amplification reactions using common primers amplification. Generally, methods of the invention employ multiple steps such as template-specific hybridization, a linear amplification, partial degradation of nucleic acid, and ligation. At the end of the process the sequences of selected polynucleotides are flanked by the common sequences which can be used for exponential amplification using common primers. In some aspects the polynucleotides are associated with a barcode and the presence of the barcode is detected to measure the amount of the polynucleotide.

9 Claims, 46 Drawing Sheets

(56) References Cited

U.S. PATENT DOCUMENTS

| | | | |
|---|---|---|---|
| 6,858,412 | B2 | 2/2005 | Willis et al. |
| 7,682,999 | B2 | 3/2010 | Teyssedre |
| 2003/0049616 | A1 | 3/2003 | Brenner et al. |
| 2004/0110213 | A1 | 6/2004 | Namsaraev |
| 2005/0136414 | A1* | 6/2005 | Gunderson et al. ............... 435/6 |
| 2007/0218478 | A1 | 9/2007 | Bai et al. |
| 2008/0242560 | A1* | 10/2008 | Gunderson et al. ............. 506/26 |
| 2011/0269631 | A1* | 11/2011 | Fu et al. ............................ 506/2 |

FOREIGN PATENT DOCUMENTS

| | | |
|---|---|---|
| EP | 0439182 | 7/1991 |
| EP | 0799897 | 10/1997 |
| WO | WO 89/09835 | 10/1989 |
| WO | WO 89/12696 | 12/1989 |
| WO | WO 90/01069 | 2/1990 |
| WO | WO 96/41012 | 12/1996 |

OTHER PUBLICATIONS

Barzilay et al., Identification of Critical Active-site residues in the multifunctional human DNA repair enzyme HAP1, Nature Structural Biology vol. 2, No. 7, Jul. 1995, 561-568.

Barzilay et al, Site-Directed mutagenesis of the human DNA repair enzyme HAP1: Identification of residues important for AP endonuclease and RNase H activity, Nucleic Acids Research 1995, vol. 23, No. 9, 1544-1550

Becker et al, Absolute mRNA quantification using the polymerase chain reaction (PCR). A novel approach by a PCR aided transcript titration assay (PATTY), Nucleic Acids Research, vol. 17, No. 22, 1989, 9437-9446.

Bernard et al, Color Multiplexing Hybridization Probes Using the Apolipoprotein E Locus as a Model System for Genotyping, Analytical Biochemistry 273, 221-228 (1999).

Brenner et al, In vitro cloning of complex mixtures of DNA on microbeads: Physical separation of differentially expressed cDNAs, PNAS, Feb. 15, 2000, vol. 97, No. 4, 1665-1670.

Bullard et al, Direct Comparison of nick-joining activity of the nucleic acid ligases from bacteriophage T4, Biochem. J. (2006) 398. 135-144

Bullard et al, Direct Comparison of nick-joining activity of the nucleic acid ligases from bacteriophage T4, Supplementary Information, School of Biological Sciences, University of East Anglia, Norwich NR4 7TJ, United Kingdom Demple et al, Cloning and expression of APE, the cDNA encoding the major human apurinic endonuclease: Definition of a family of DNA repair enzymes, Proc. Natl. Acad. Sci. USA. vol. 88, 11450-11454, Dec. 1991

Diviacco et al, A Novel procedure for quantitative polymerase chain reaction by coamplification of competitive templates, Gene, 122 (1992) 313-320.

Dong et al, Flexible Use of high-Density Oligonucleotide Arrays for Single-Nucleotide Polymorphism Discovery and Validation, Affymetrix, Santa Clara, CA 95051, USA, Genome Research, 11:1418-1424.

Eckert et al, DNA Polymerase Fidelity and the Polymerase Chain Reaction, 1:17-24, PCR Methods and Applications.

Engler et al, DNA Ligases, The Enzymes, vol. XV.

Fan et al, Parallel Genotyping of Human SNPs Using Generic High-Density Oligonucleotide Tag Arrays, Genome Research, 10:853-860.

Flaherty et al, AP Endonucleases and the many functions of Ref-1, Am. J. Respir. Cell Mol Biol. vol. 25, 664-667 (2001).

Freeman et al, Quantitative RT-PCR: Pitfalls and Potential, BioTechniques 26:112-125 (Jan. 1999).

Gorman et al, The crystal structure of the human DNA repair endonuclease HAP1 suggests the recognition extra-helical deoxyribose at DNA abasic sites, The EMBO Journal, vol. 16, No. 21, 6548-6558. (1997).

Guatelli et al, Isothermal, in vitro amplification of nucleic acids by a multienzyme reaction modeled after retrovirat replication, Proc. Natl. Acad. Sci USA, vol. 87, 1874-1878, (Mar. 5, 1990).

Higgins et al, DNA—Joining Enzymes: A Review, Enzymes in Recombinant, Methods in Enzymology, vol. 68, 50-71.

Kwoh et al, Transcription-based amplification system and detection of amplified human immunodeficiency virus type 1 with a bead-based sandwich hybridization format, Proc. Natl. Acad. Sci, USA, vol. 86, 1173-1177 (Feb. 1989).

Landegren et al, A Ligase-Medicated Gene Detection Technique, Science, vol. 241, 1078-1080 (1988).

Levin et al, Homogeneous *Esoherichia coli* Endonuclease IV, The Journal of Bioiogical Chemistry, vol. 263, No. 17, 8066-8071 (Jun. 15, 1988).

Ljungquist, S, A New Endonuclease from *Escherichia coli* acting at apurinic sites in DNA, J. Biol. Chem. 1977, 252: 2808-2814.

Mackay et al, Real-time PCR in Virology, Nucleic Acids Research, 2002, vol. 30, No. 6, 1292-1305.

Makrigiogos et al, A PCR-based amplification method retaining the quantitative difference between two complex genomes, Nature Biotechnology, vol. 20, 2002, 936-939.

Marenstein et al, Human AP endonuclease (APE1) demonstrates endonucleolytic activity against AP sites in single-stranded DNA, Elsevier, DNA Repair 3 (2004), 527-533.

Mattila et al, Fidelity of DNA Synthesis by the Thermococcus litoralis DNA Polymerase—an extremely heat stable enzyme with proofreading activity, Nucleic Acids Research, vol. 19, No. 18, 4967-4973.

Robson, et al, Isolation of cDNA clones encoding a human apurinic/apyrimidnic endonuclease that corrects DNA repair and mutagenesis defects in *E. coli* xth (exonuclease III) mutants, Nucleic Acids Research, vol. 19, No. 20, 5519-5523.

Shoemaker et al, Quantitative phenotypic analysis of yeast deletion mutants using a highiy parallel molecular bar-coding strategy, Nature Genetics, vol. 14, Dec. 1996, 450-456.

Tchou et al, Substrate Specificity of Fpg Protein, The Journal of Biological Chemistry. vol. 269, No. 21, May 27, 1994, 15318-15324.

Vidal et al, XRCC1 coordinates the initial and late stages of DNA abasic site repair through protein-protein interactions, the EMBO Journal, vol. 20, No. 22, 6530-6539, (2001).

Walker et al, Identification of Residues in the Human DNA Repair Enzyme HAP1 (Ref-1) that are Essential for Redox Regulation of Jun DNA Binding, Molecular and Cellular Biology, Sep. 1993, vol. 13, No. 9, 5370-5376.

Walker et al, Strand Displacement amplification—an isothermal, in vitro DNA amplification technique, Nucleic Acids Research, vol. 20, No. 7, 1691-1696.

Wilson et al, Incision Activity of Human Apurinic Endonuclease (Ape) at Abasic Site Analogs in DNA, The Journal of Biological Chemistry, vol. 270, No. 27, Jul. 7, 1995, 16002-16007.

Wu et al, The Ligation Amplification Reaction (LAR)—Ampiification of Specific DNA Sequences Using Sequential Rounds of Template-Dependent Litigation, Genomics 4, 560-569 (1989).

Xanthoudakis et al, Redox Activationn of Fos—Jun DNA binding activity is mediated by a DNA repair enzyme, The EMBO Journal, vol. 11, No. 9, 3323-3355, (1992).

Xu et al, High Sequence Fidelity in a non-enzymatic DNA autoligation reaction, Nucleic Acids Research, 1999, vol. 27, No. 3, 875-881.

Zimmermann et al, Technical Aspects of Quantitative Competitive PCR, BioTechniques 21:268-279, Aug. 1996.

\* cited by examiner

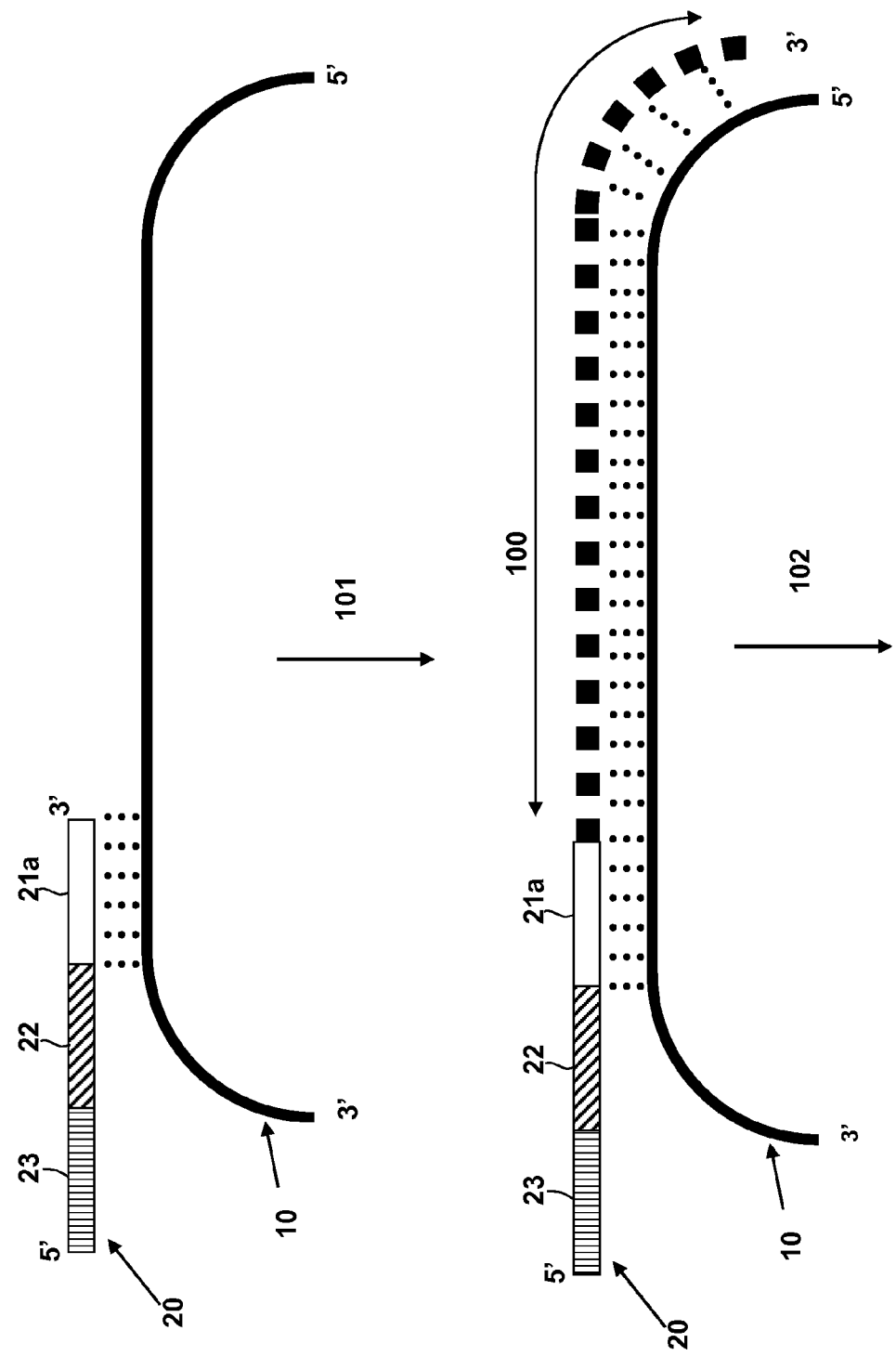

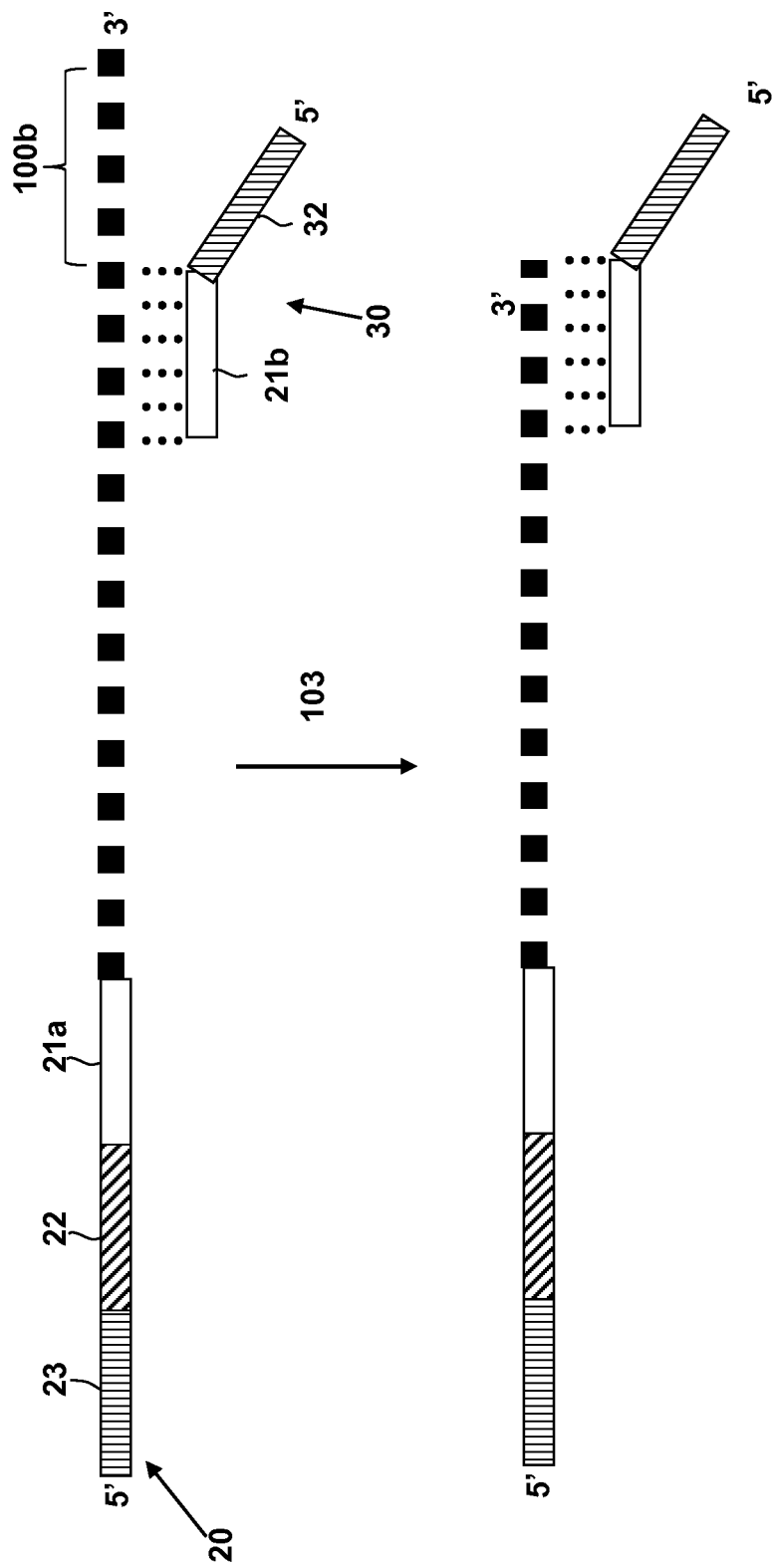

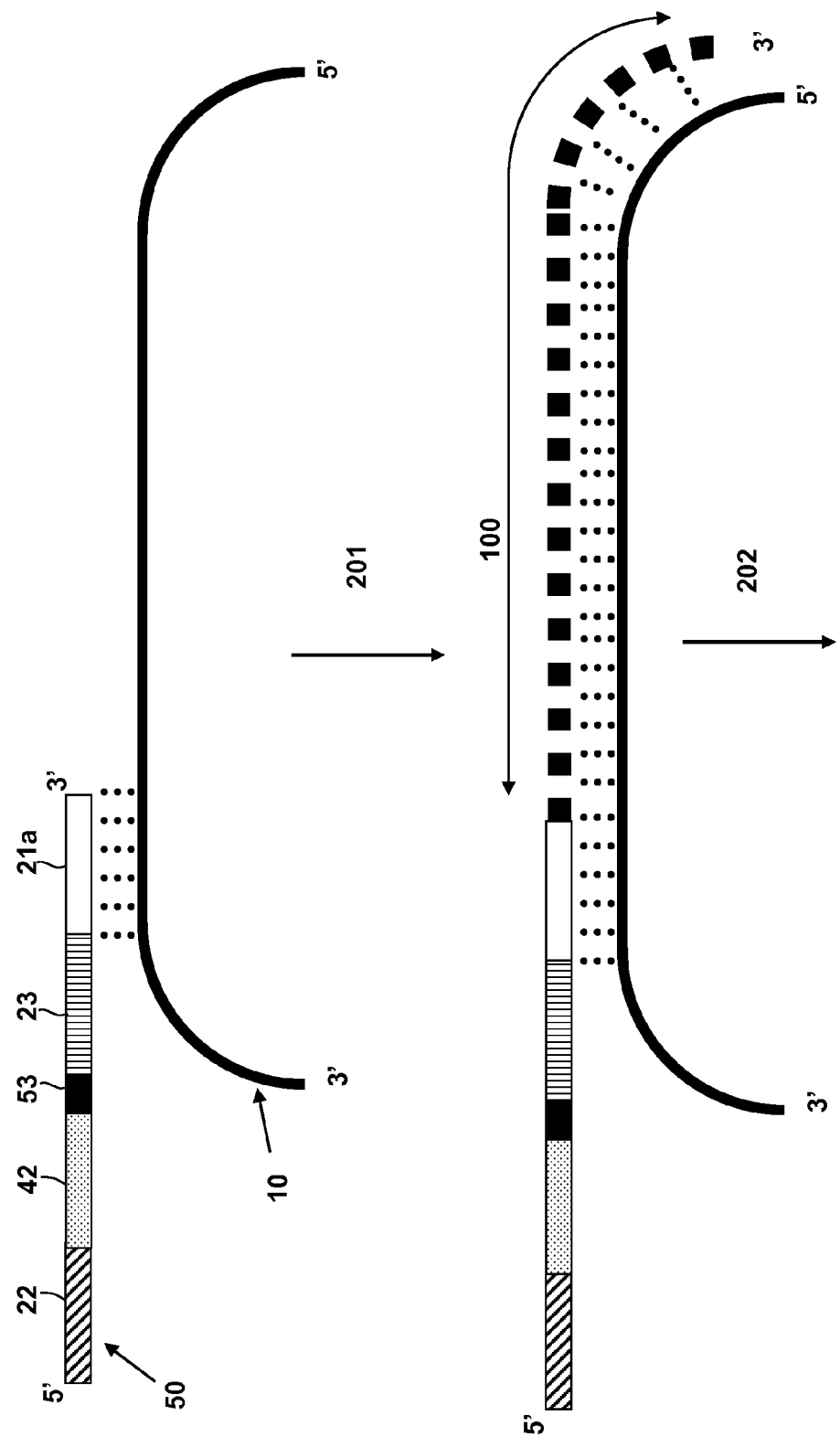

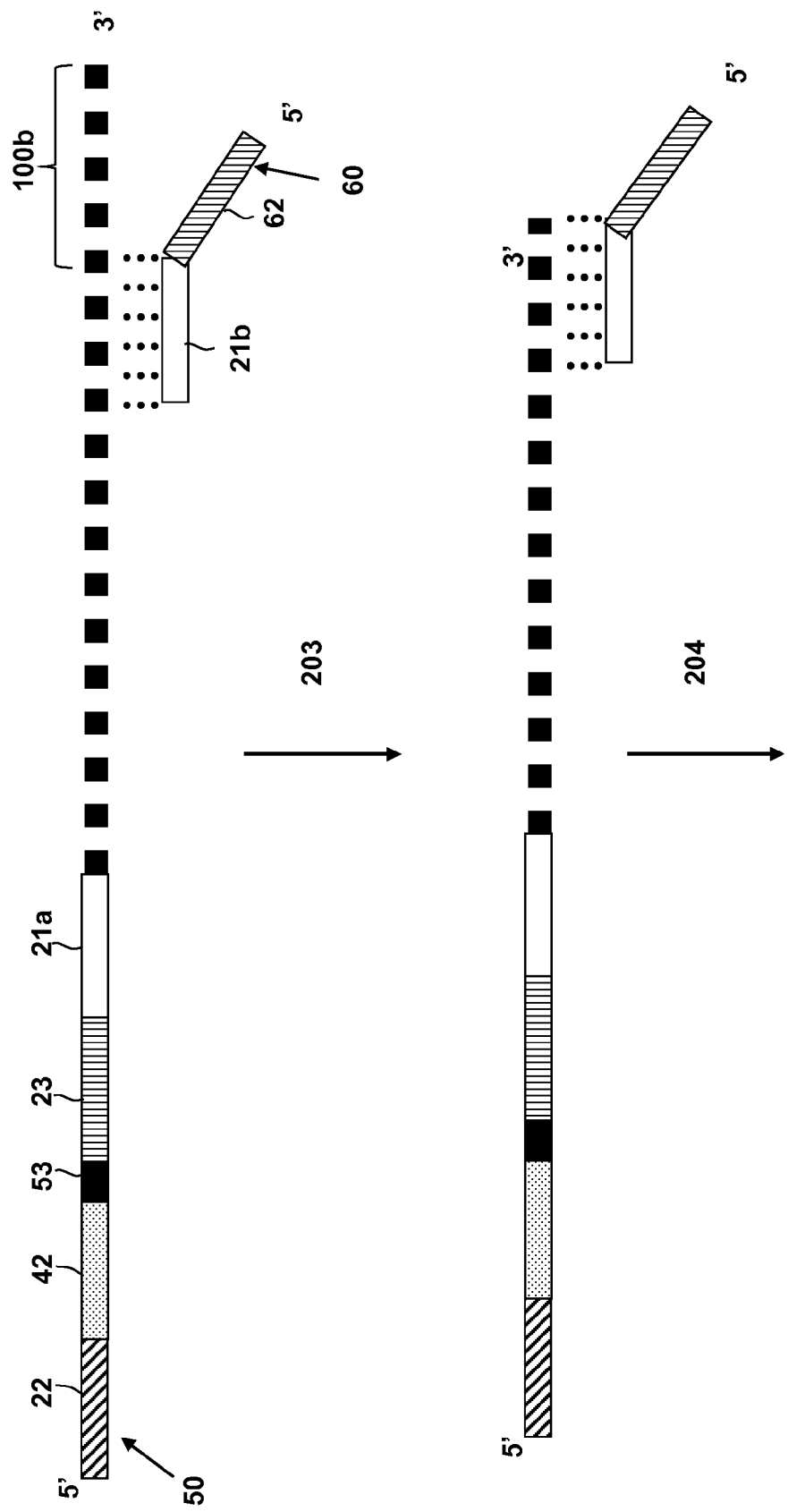

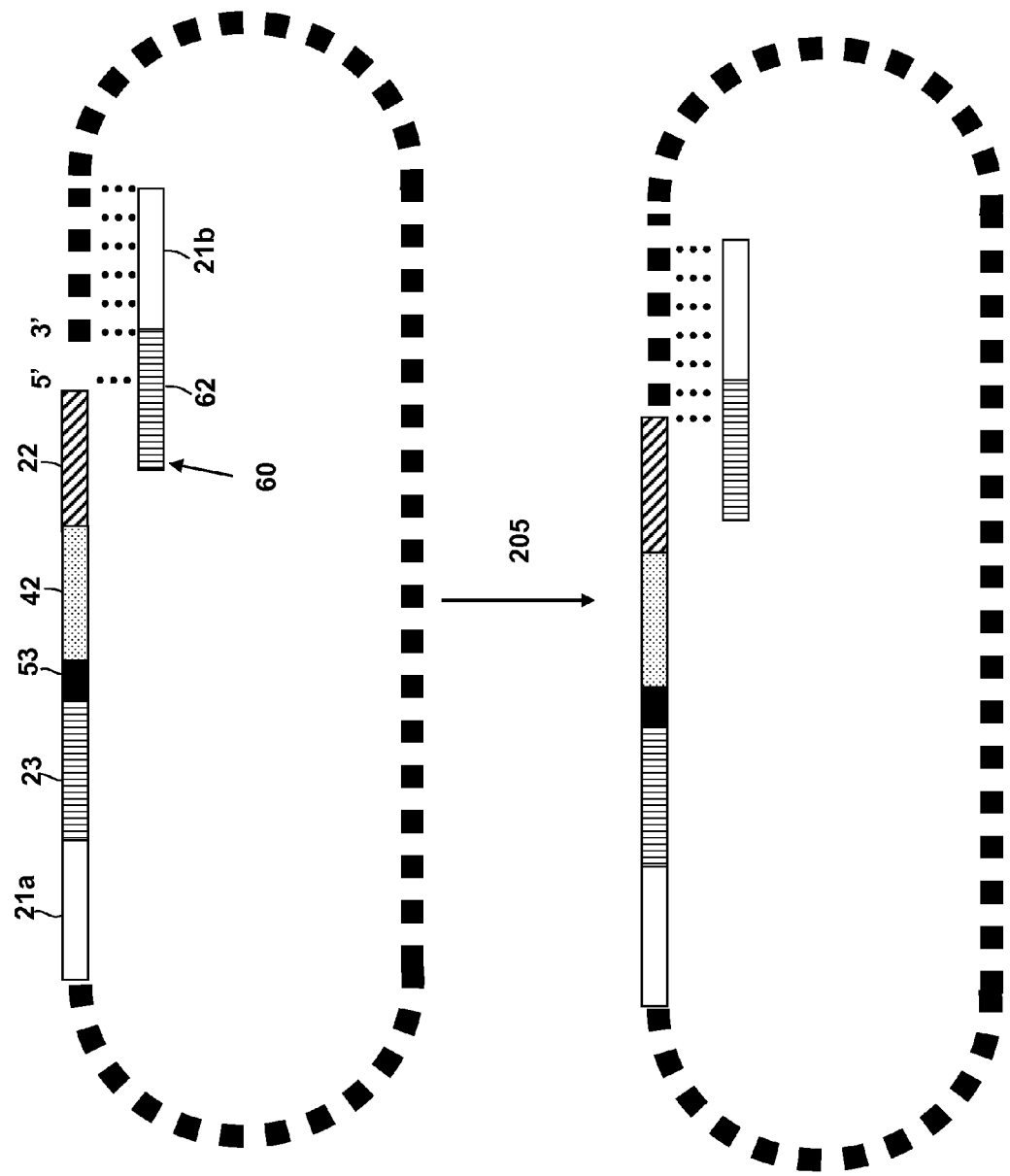

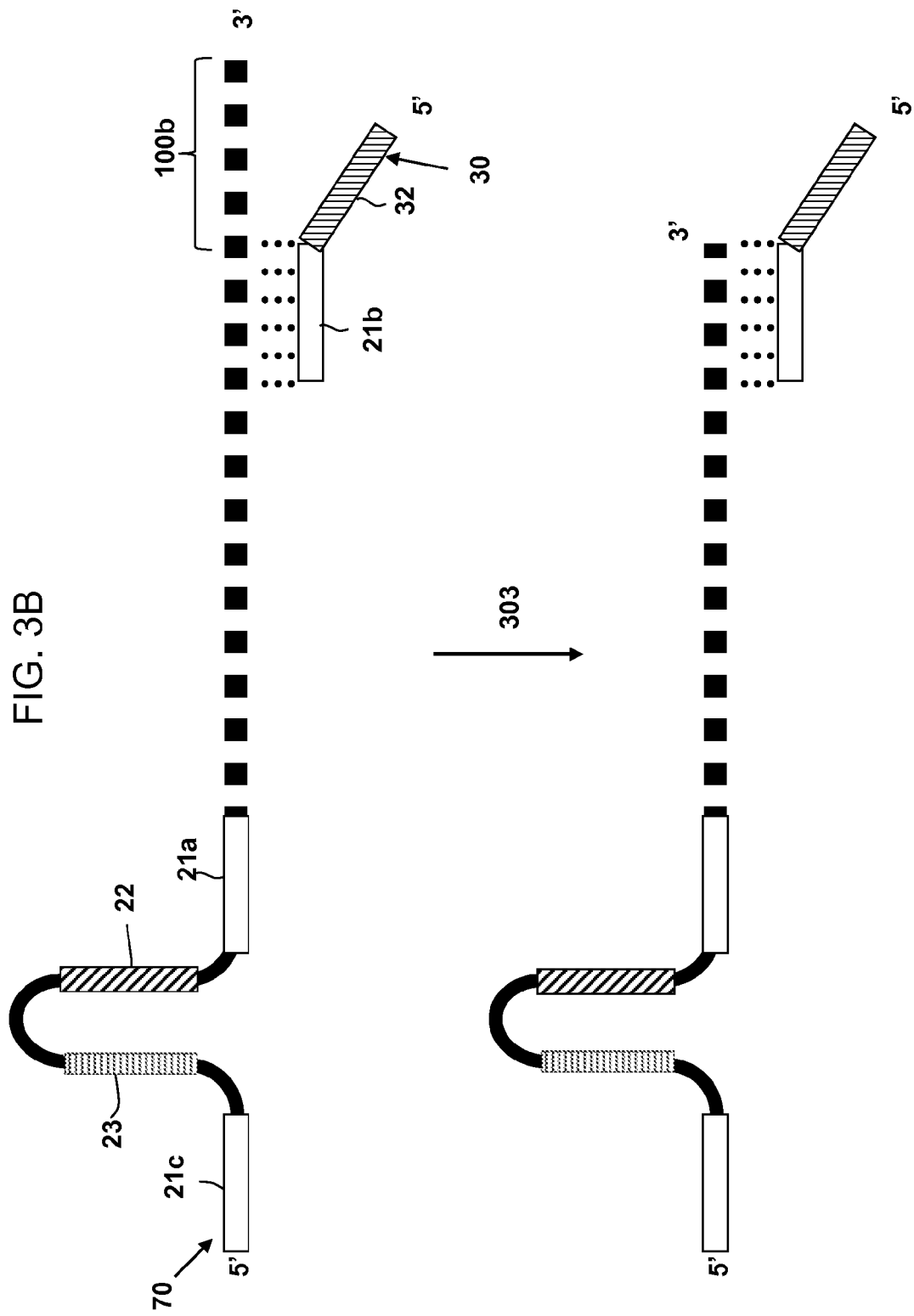

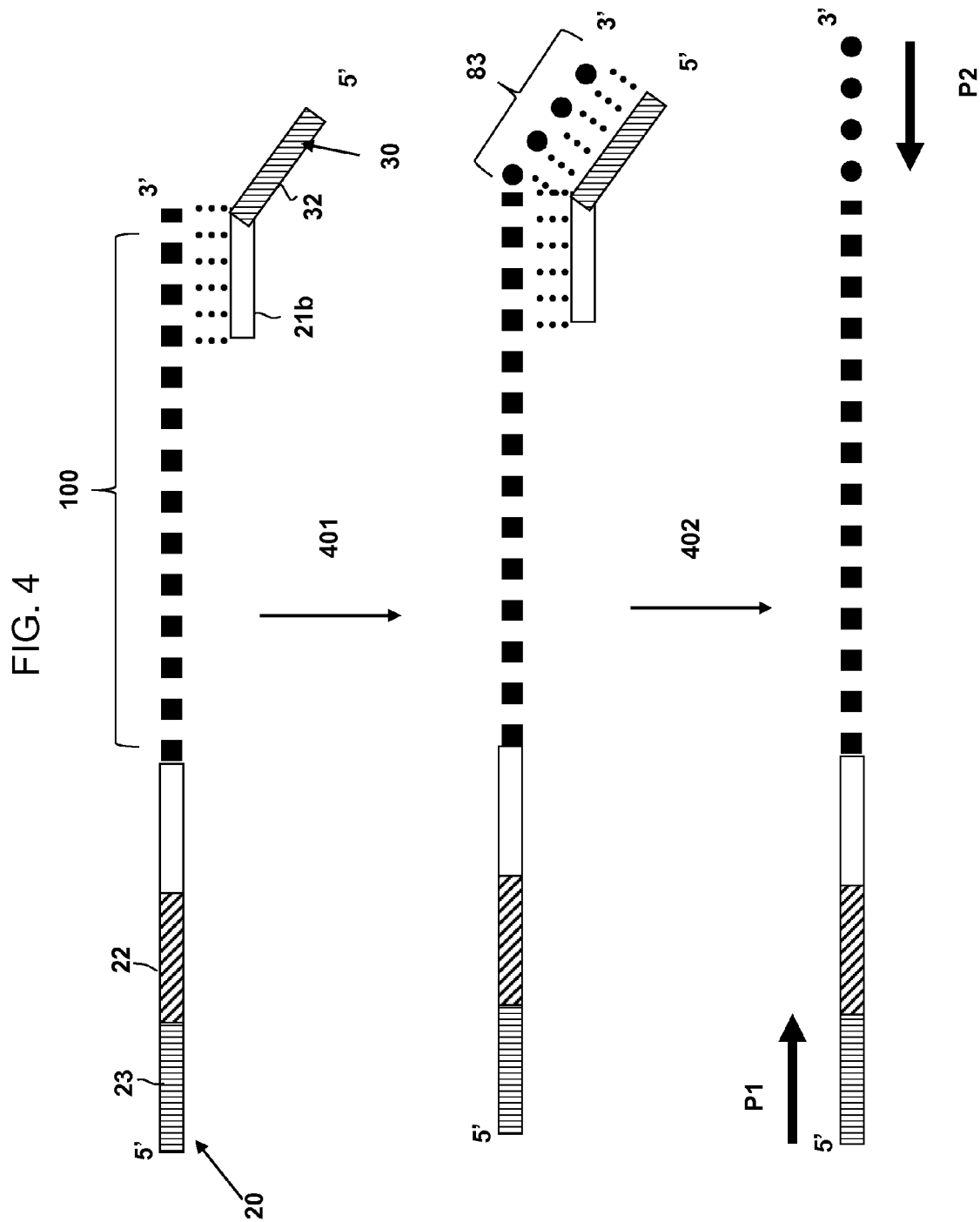

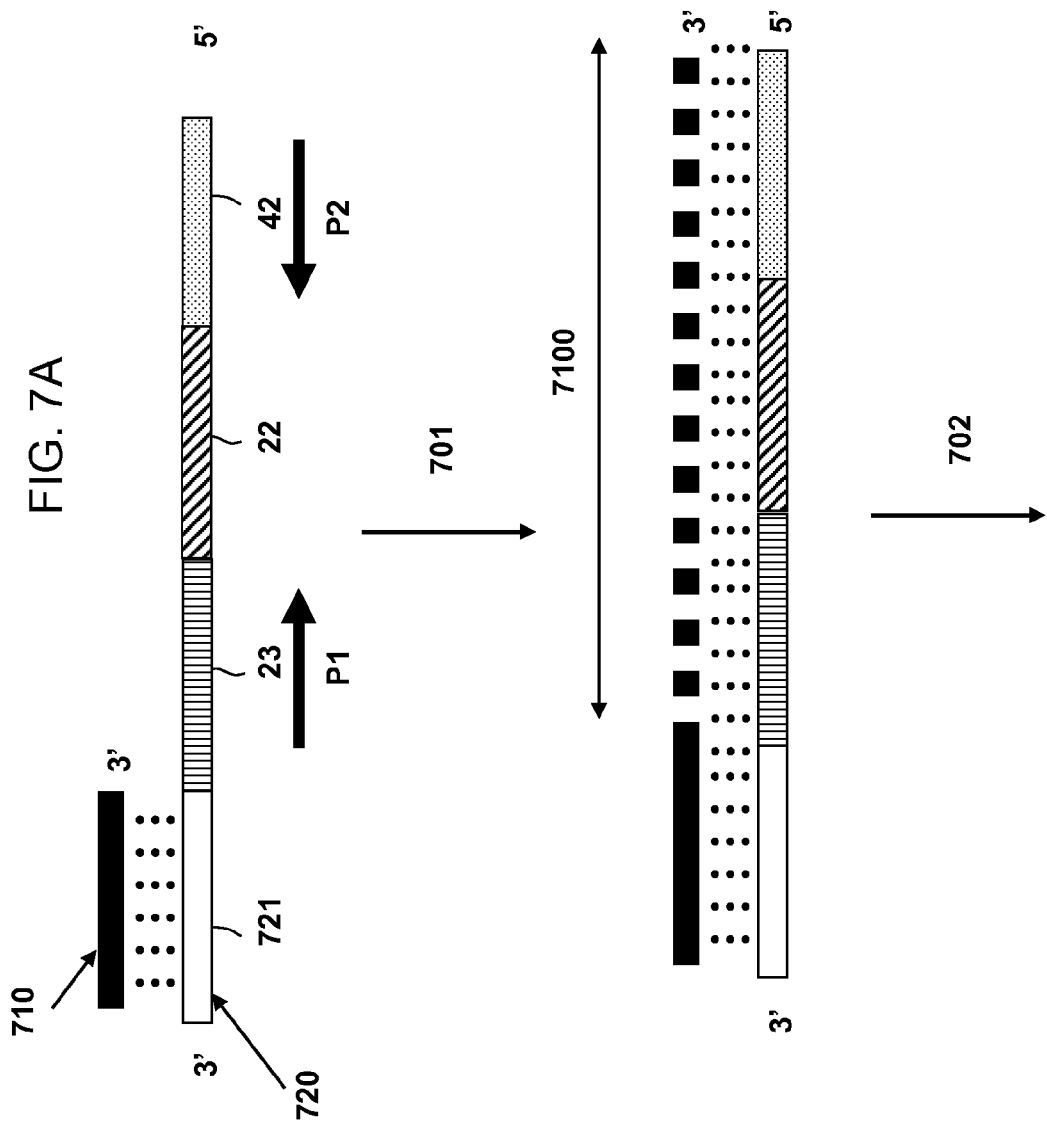

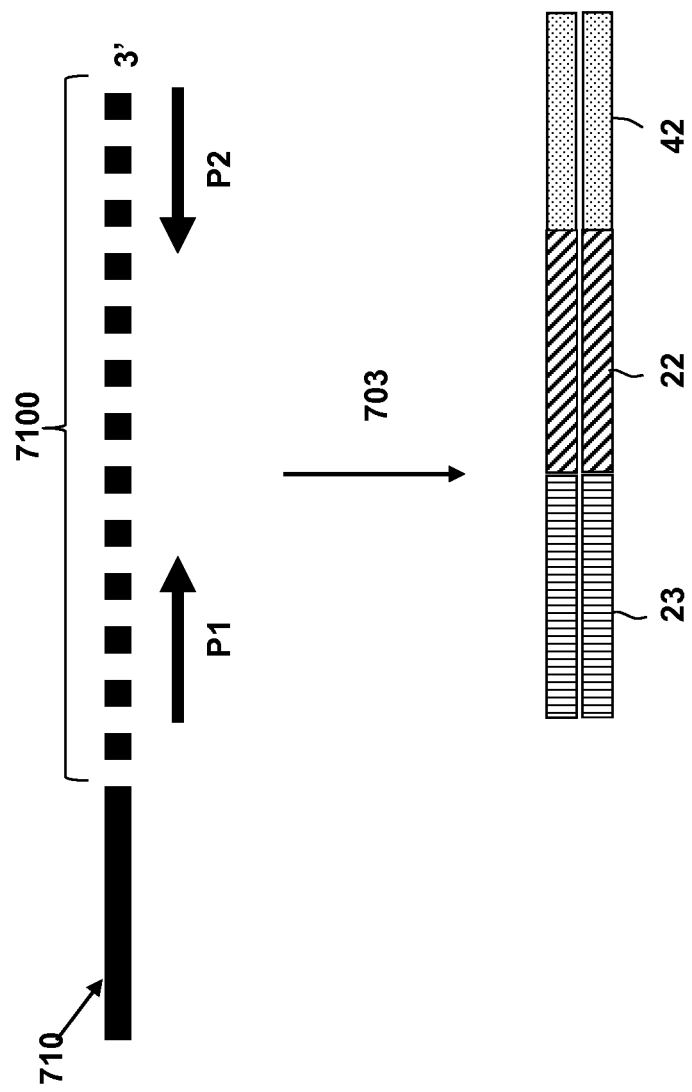

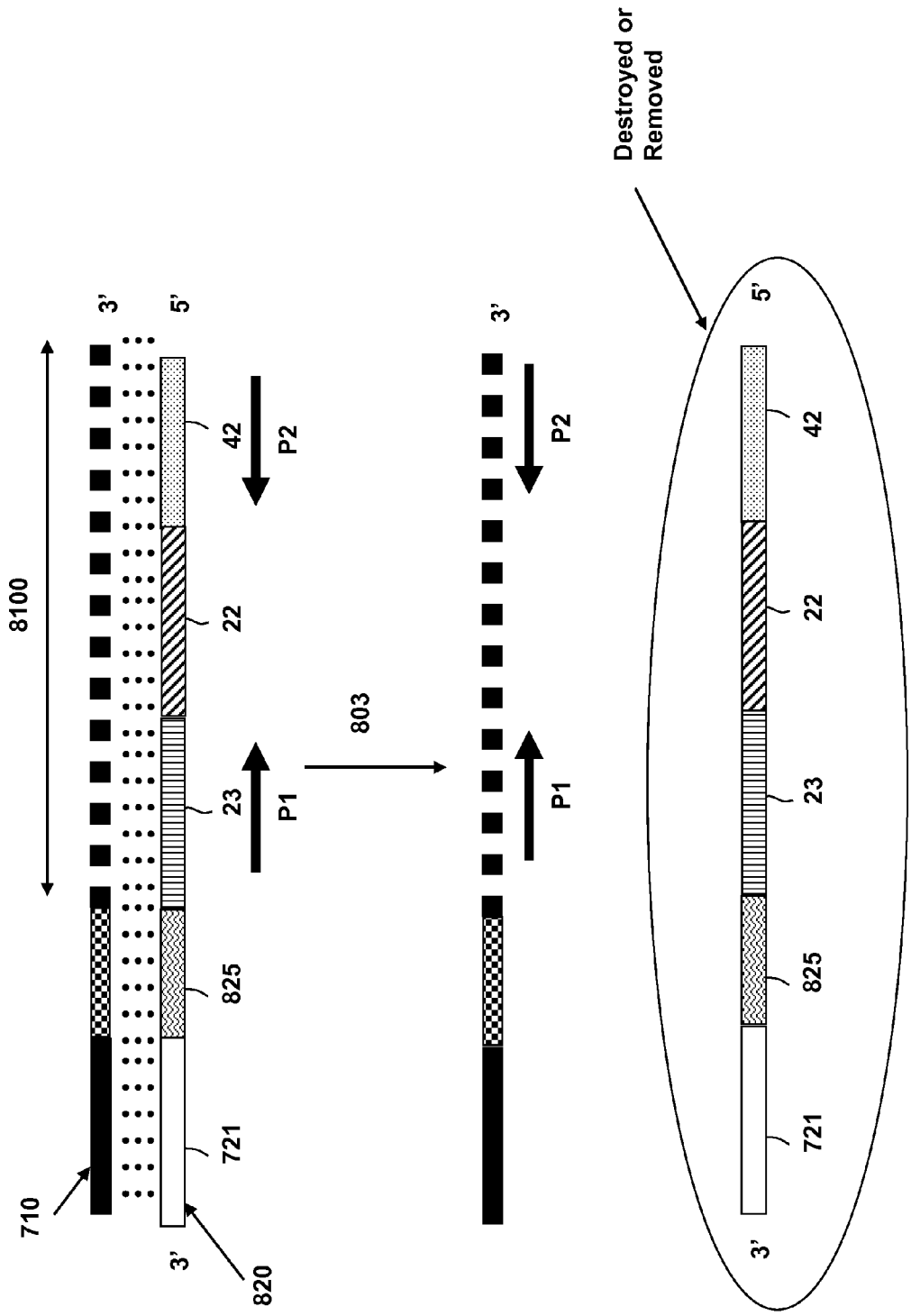

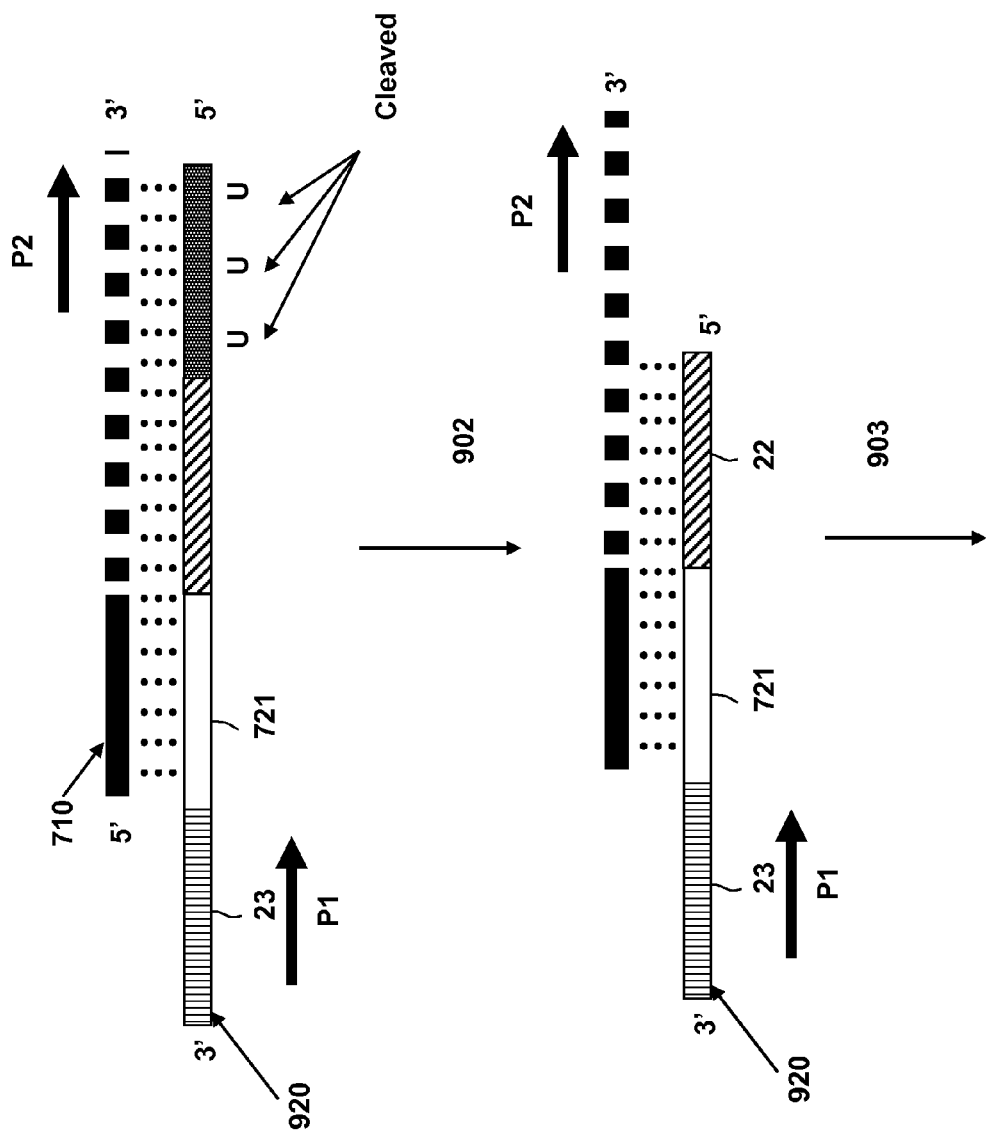

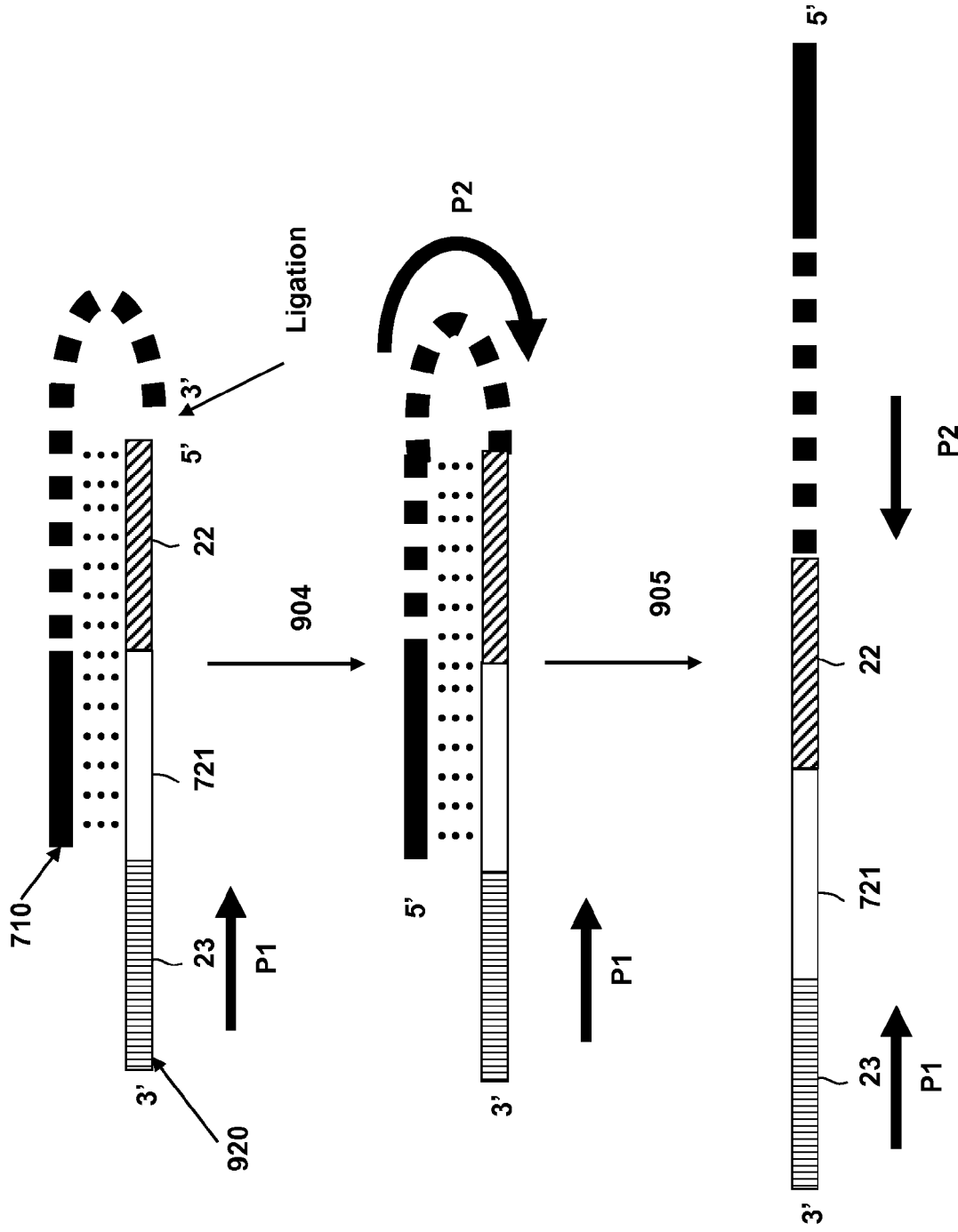

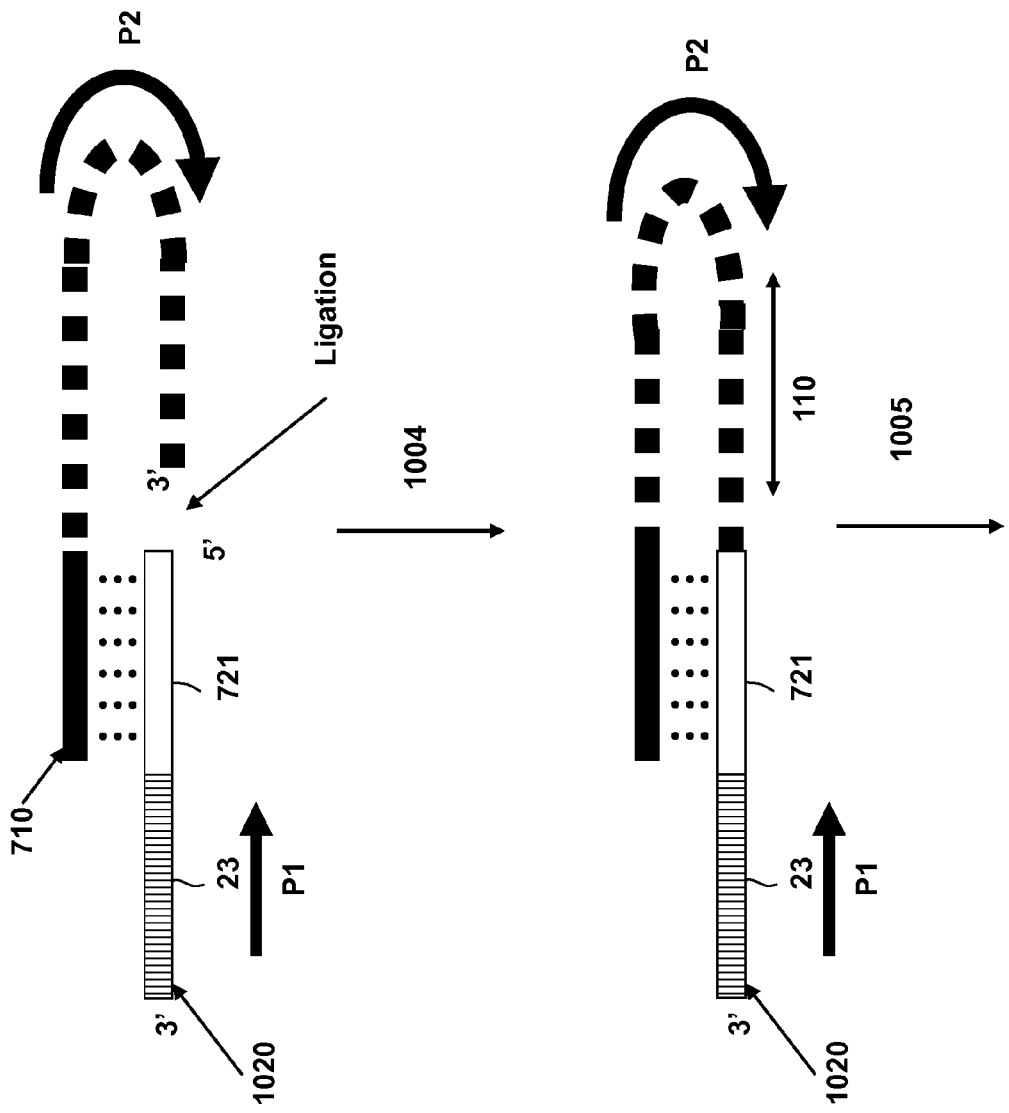

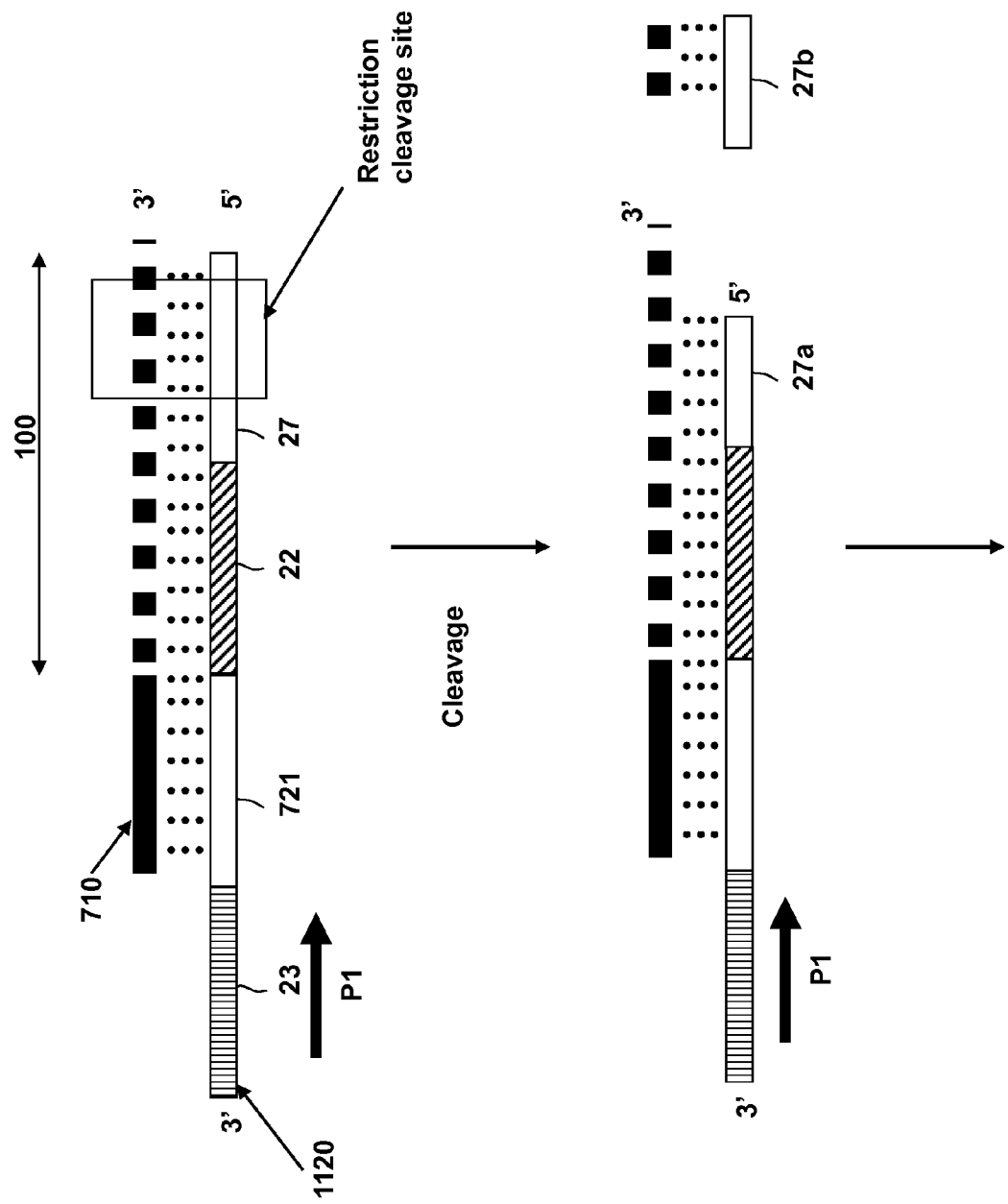

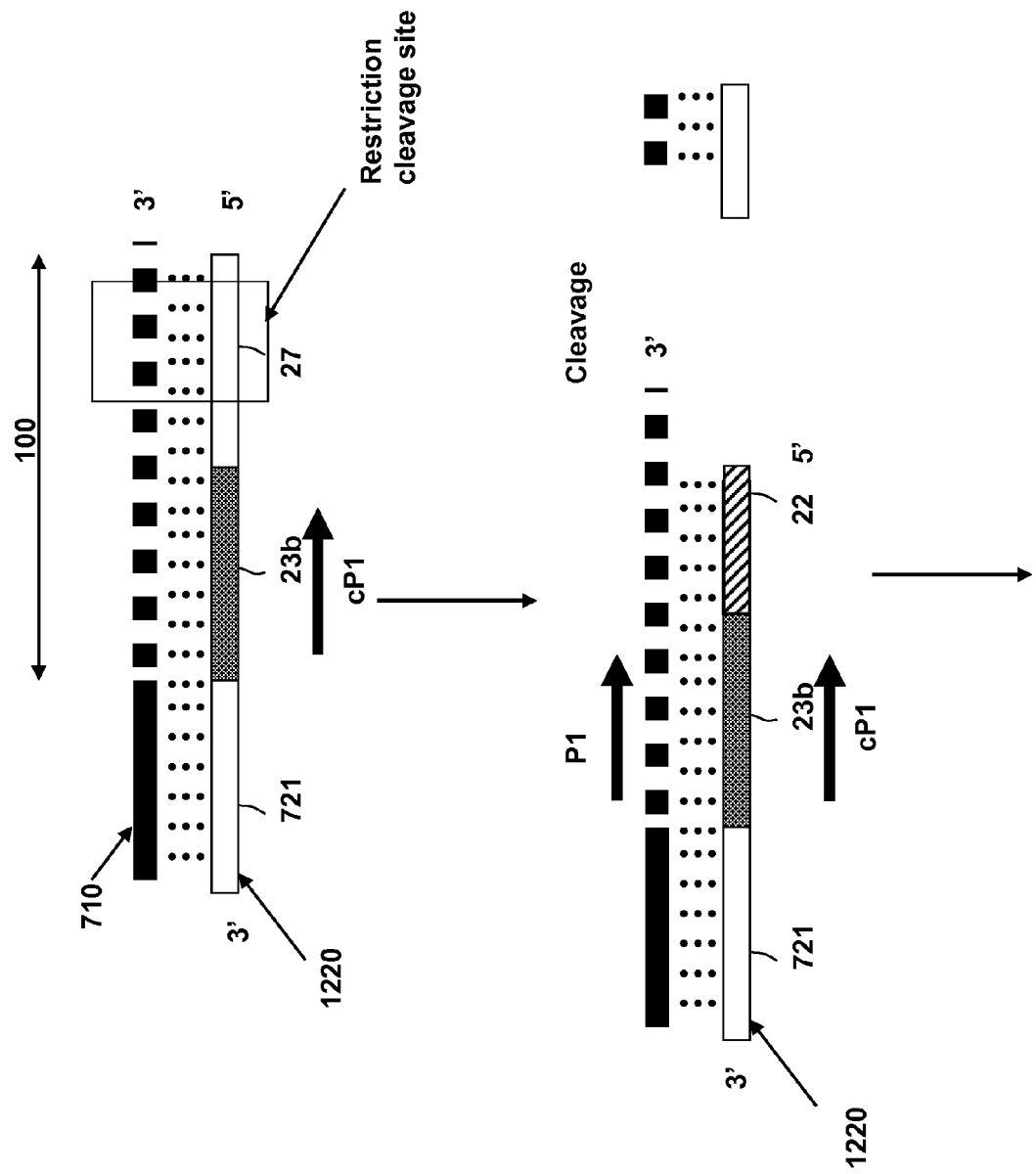

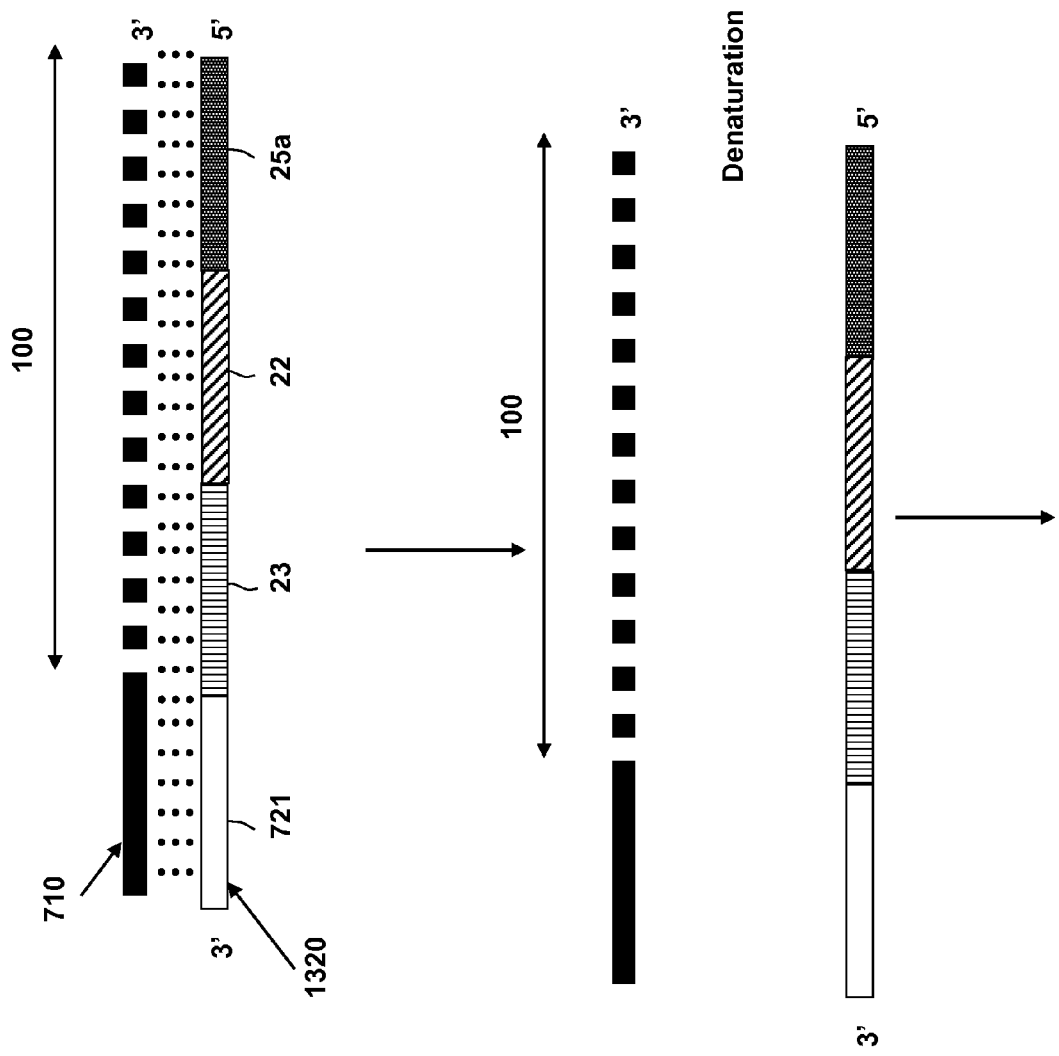

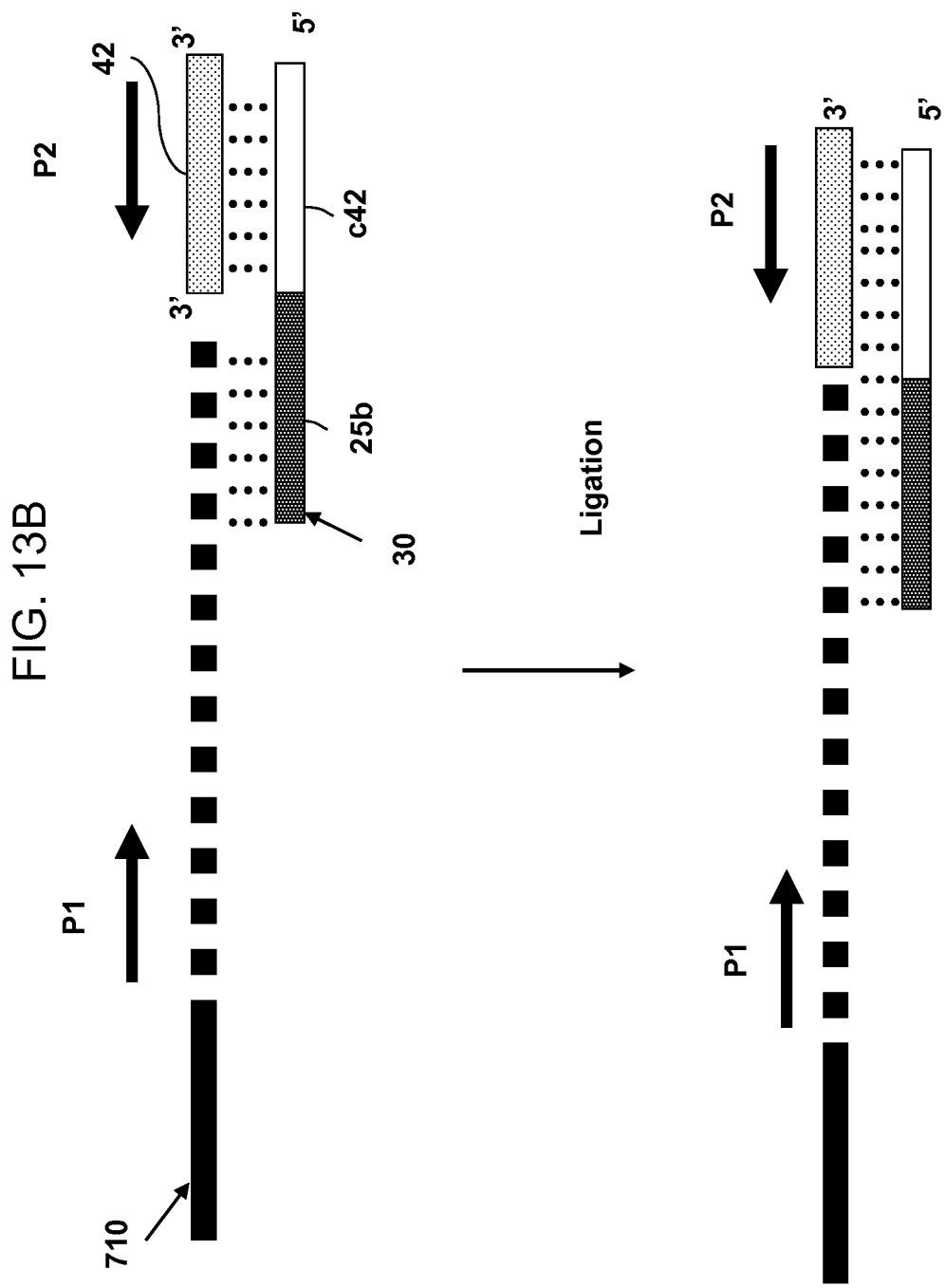

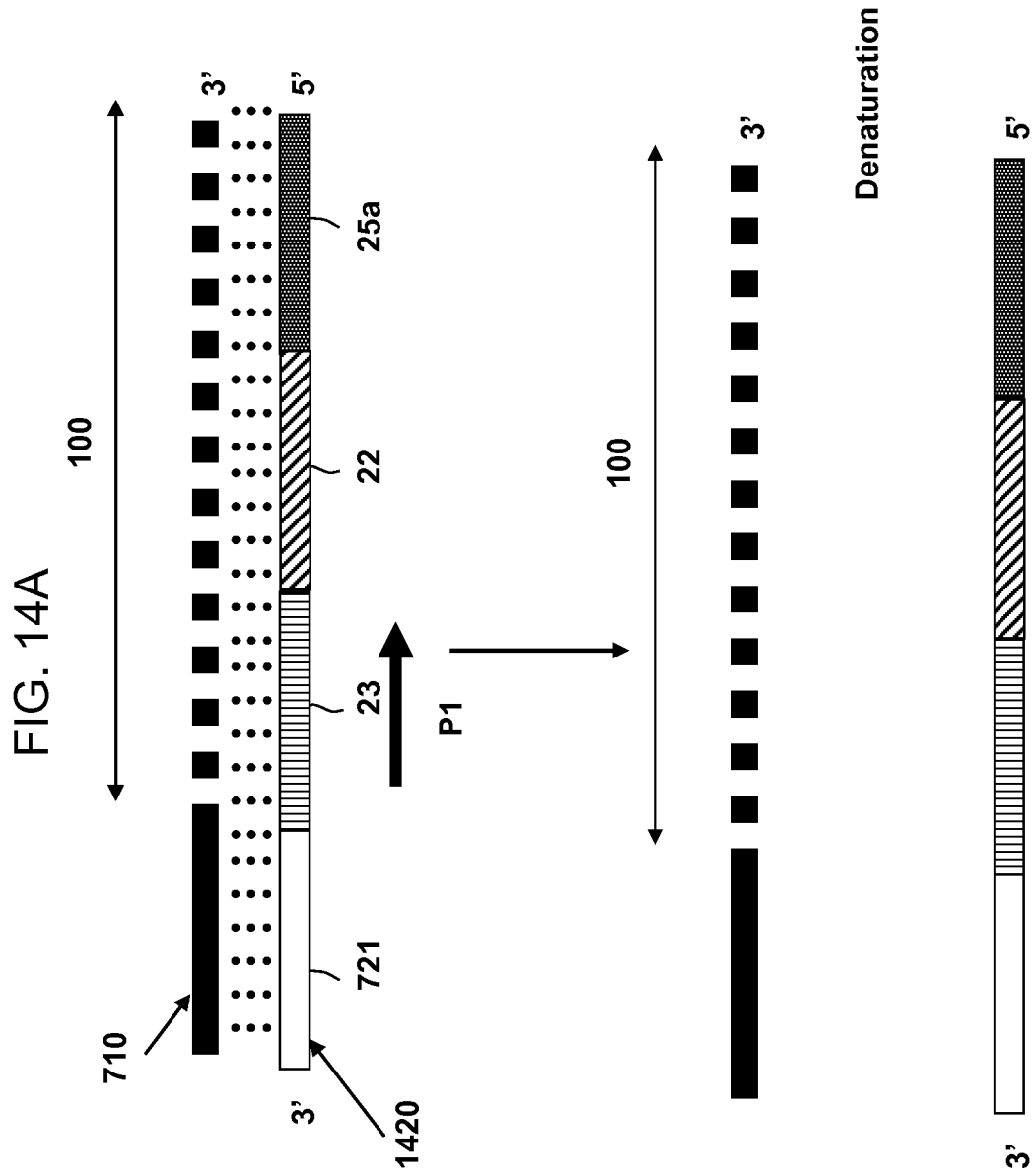

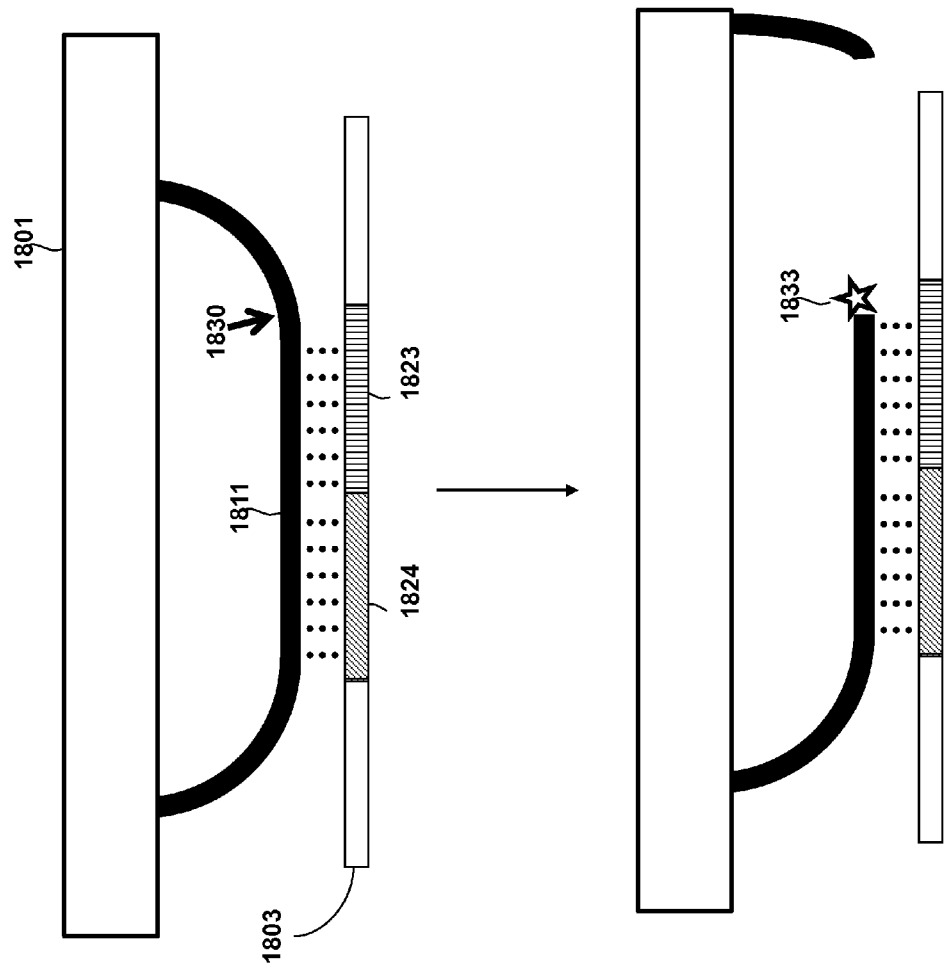

MULTIPLEX AMPLIFICATION METHODS

RELATED APPLICATIONS

This application claims priority to U.S. Provisional application No. 61/349,004 filed May 27, 2010, the entire disclosure of which is incorporated herein by reference in its entirety.

FIELD OF THE INVENTION

The invention is related to methods for preparing a sample that is enriched for selected target sequences. Specifically, this invention provides methods, computer software products and systems for the selective amplification of target nucleic acids including DNA and RNA.

BACKGROUND OF THE INVENTION

Amplification of nucleic acids and analysis of the resulting amplification products has revolutionized the basic and clinical sciences. Applications of these techniques include molecular cloning, nucleic acid sequencing, genotyping, detection and identification of single nucleotide polymorphisms (SNP) and other polymorphisms and mutations and the quantitation of gene expression, Various techniques for nucleic acid amplification have been developed, such as strand displacement amplification, transcription-based amplification, and polymerase chain reaction (PCR).

Use of PCR in large scale research projects and in clinical applications entails amplification of many distinct target sequences with the concomitant generation of a great number of PCR amplicons. As the scale of such projects increases, it has become cost prohibitive and inefficient to undertake the necessary reactions singly. Thus, there is great interest in developing methods of performing multiple amplification reactions in parallel in the same reaction vessel using a common pool of template and reagents.

Such multiplex PCR methods, in which multiple pairs of target-specific primers are used to co-amplify multiple targets, have met with only qualified success. Combining all the required primers in the same tube greatly increases the frequency of formation of primer-dimer and other spurious amplification products. As the number of primer pairs rises in multiplex PCR, the number of potential primer-dimer interactions (or spurious amplicons generated by two different primers) increases exponentially according to the number of primers used.

Even with careful attention paid to the design of the multiplex primer pairs to avoid obvious primer-dimer incompatibilities, conventional multiplex PCR is generally limited to about 10-20 simultaneous amplification reactions before undesired amplification products predominate. Different approaches to ameliorate the problems associated with multiplex PCR have been developed, but none with unqualified success.

PCT publication WO 96/41012 discloses a method for multiplex PCR that entails two rounds of amplification and that uses primer pairs comprising template-specific sequences at their respective 3' ends and universal, or common, primer sequences at their respective 5' ends. The first round of amplification uses the specific primer sequences and the second amplification uses the universal primer sequences. The second round normalizes differential binding of the specific primers to different templates.

Another multiplex method uses a single specific primer for each target and a single common primer. N. E. Broude, et al., *Proc. Natl. Acad. Sci. USA* 98:206-211 (2001). This method still suffers from the amplification of spurious products, however, and therefore remains limited in its application.

Yet another multiplex method uses a precircle probe to form a hybridization complex with sequence of interest. After hybridization complex is contacted with a ligase to form a closed circular probe, and cleaving the dosed circular probe at the cleavage site to form a cleaved probe. In the precircle probe the common sequences are in opposite directions, but in the cleaved probe they are facing toward each other and can be used for amplification by PCR. U.S. Pat. No. 6,858,412.

The oligonucleotide ligation assay (OLA; sometimes referred to as the ligation chain reaction (LCR)) involves the ligation of at least two smaller probes into a single long probe, using the target sequence as the template for the ligase. See generally U.S. Pat. Nos. 5,185,243, 5,679,524 and 5,573,907; EP 0 320 308 B1; EP 0 336 731 B1; EP 0 439 182 B1; WO 90/01069; WO 89/12696; and WO 89/09835, all of which are incorporated by reference.

Many of the methods are used to archive the highest level of the enrichment at the early enzymatic steps and use simple detection steps after selective amplification. Thus, remains a need in the art for methods of simultaneous multiplex amplification of large numbers of specific nucleic acid sequences that relatively simple, cost effective and do not require highest degree of enrichment.

Other type methods rely on the converting the small RNA into cDNA by using short LNA primers or attaching primer at the 3' end of the RNA molecule and using it as template for reverse transcription.

For other type of RNA analysis like RNA expression profiling the quality of the RNA is important issue. Often the degradation of RNA or chemically modifications of RNA in FFPE samples prevent usage of those samples in expression analysis. The conversion of the RNA molecule into cDNA molecule is mostly affected by the RNA quality. Developing new method which avoiding cDNA synthesis would be beneficial for such RNA sample usage.

In each of these methods, analysis of the small RNAs or damaged RNA is problematic. Accordingly, it is an object of the invention to provide compositions and methods for the detection and quantification of the products by capturing the ribonucleotides on the template and converting the captured molecule into the amplifiable detectable decoding sequence.

SUMMARY OF THE INVENTION

Methods and compositions are disclosed herein selective attachment of common sequences to collections of specific nucleic acid targets so they can be amplified in one or more multiplex reactions by PCR with common primers. The methods may be used for connecting common sequences to the ends of the specific target nucleic acids so for amplification by multiplex PCR using a single primer or a pair of common primers.

In some aspects the common sequences are attached in two steps. In a first step, a first oligonucleotide, containing the priming sequence at or near the 5' end, is hybridized to the target sequence and extended by DNA synthesis using the target as template. The first oligonucleotide sequence is attached to the 5' end of the newly synthesized sequence of interest. In second step, another nucleotide (probe) is attached to 3' end of the newly synthesized stand by degradation of 3' end and ligation reaction.

Accordingly, in a first aspect, the present disclosure provides for a method of nucleic acid amplification by which a linear amplification molecule contacts a nucleic acid template under conditions that support its specific hybridization thereto. In some embodiments, the linear amplification molecule is a DNA oligonucleotide. According to some embodiments the template is DNA and in other embodiments template is RNA.

In the next step, one or more nucleotides complementary to corresponding nucleotides present in the template are added sequentially to the linear amplification molecule at the end hybridized to the template, resulting in the formation of an extended linear amplification molecule. In some embodiments, addition of complementary nucleotides is carried out using a DNA polymerase.

In the next step, second probe contacts to the newly synthesized extended linear molecule under conditions that support its specific hybridization, resulting in the formation of a double-stranded hybridization region in 3' end area and non hybridized single stranded ends.

In the next step, the single stranded portion of 3' end of extended linear amplification molecule is degraded by 3' to 5' exonuclease activity to form the 3' recessed end with the probe.

In the next step, to the recessed 3' end newly created by the exonuclease degradation, another ligatable oligonucleotide containing common sequence at 3' end and 4 or more bases at 5' end complementary to the corresponding nucleotides present in the second probe are added by ligation resulting in the attachment of common sequence to the 3' end of newly synthesized linear amplification molecule.

In last step, the extended linear molecule flanked with common sequences is used as template in an exponential amplification reaction, such as PCR. Where multiple amplifications are desired to be carried out in parallel in the same reaction, common primers can be used in the PCR. After PCR, the exponentially amplified sequences from the starting template are analyzed.

In another aspect, the methods disclosed herein provide an alternative method for attaching of common sequence at 3' end of the newly synthesized linear molecule by intra-molecular ligation of 5' end of first probe to recessed 3' end of the newly synthesized linear molecule. In the first step, a linear amplification molecule contacts a nucleic acid template under conditions that support its specific hybridization thereto. In the next step, one or more nucleotides complementary to corresponding nucleotides present in the template are added sequentially to the linear amplification molecule at the end hybridized to the template, resulting in the formation of an extended linear amplification molecule. In the next step, the second probe is hybridized to the extended linear molecule near 3' end area. Single stranded 3' end of the extended linear amplification molecule is degraded to form recessed 3' end with second probe. The 5' end of the second probe contains sequence which is complementary to the sequence located 5' end of the first probe. Under conditions that support specific intra-molecular interaction, covalent bond can be formed by ligating 5' end of the first probe to recessed 3' end of the newly synthesized linear molecule. An closed circle is formed after ligation and can be used as template for amplification reaction. In an optional last step, the closed circle can be opened by cleavage site in first probe and used as a template in an exponential amplification reaction, such as PCR.

In another aspect, the first probe contains common sequence flanked by two sequences, which form two double stranded regions with the nucleic acid template. Once the two duplexes formed the looped structure in between is protected from degradation by single stranded exonucease activities and can be used for increasing specificity of first hybridization.

In another aspect, an alternative method for attaching of common sequence at the 3' end of the newly synthesized linear molecule by DNA synthesis is provided. After formation of extended linear molecule the second probe is hybridized near 3' end area. The second probe contains template specific sequence 3' end and common sequence at 5' end. After hybridization of the second probe the single stranded 3' end of newly synthesized linear molecule is degraded with formation of recessed 3' end. By extending recessed 3' end of linear molecule using second probe as template the complementary common sequence is added at 3' end of the linear molecule. The added common sequence is used as primer site for amplification by PCR.

In another aspect, an alternative method for attaching of common sequence at the 3' end of the newly synthesized linear molecule by intra-molecular ligation of 5' end of second probe is provided. After formation of extended linear molecule the second probe is hybridized near its 3' end area. The second probe contains template specific sequence 3' end and common sequence at 5' end. After hybridization of the second probe the single stranded 3' end of newly synthesized linear molecule is degraded with formation of recessed 3' end. Under specific conditions suitable for intra-molecular interaction the 5' end of the second probe is ligated to recessed 3' end of linear molecule with formation of loop structure. After ligation the common sequence at 5' end of the second probe is attached to 3' end of linear molecule and used as primer site for amplification by PCR.

According to alternative embodiments, additional methods useful for further reducing the formation of spurious reaction from the first and second probe and ligatable oligonucleotide products during amplification are disclosed. Thus, one embodiment provides for the elimination of excess of non reacted and nonspecific product by incorporating the cleavable nucleotides in the sequence of the first and second probe and ligatable oligonucleotide. For example uracil base is degraded by uracil glycosidase. The uracil base is incorporated in first and second probes and ligatable oligonucleotides. The common sequences are attached to both ends of the newly synthesized linear molecule. Under current invention the linear molecule will be flanked by uracil containing sequences. The second PCR primer is added to the PCR ready template and first DNA strand is synthesized using linear molecule as template and in the presence of natural nucleotides. After first PCR cycle the uracil glycosidase is added to destroy all the polynucleotides containing uracil. Only first PCR DNA strand containing natural nucleotides will be intact and used for subsequent PCR amplification.

In yet other embodiments, biotinylated nucleotides are either incorporated into the linear amplification molecule. Thereafter, a streptavidin coated substrate is used to purify biotinylated complexes away from molecules that contribute to formation of spurious reaction products.

According to alternative embodiments, a first probe further comprising a barcode sequence, i.e., a unique pattern of nucleotides that uniquely identifies the linear amplification molecule with which it is associated is disclosed.

In another aspect, the methods provide for an alternative linear molecule for nucleic acid amplification containing single primer sequence. According to this embodiment, first probe and ligatable polynucleotide contain the sequences which can be amplified with single primer PCR.

It is also an object of the disclosure to provide novel and improved methods for selectively measuring the levels of small RNAs or other RNAs in complex mixtures by capturing RNA using a probe and converting the captured molecule into measurable barcode sequences.

It is further an object of the disclosure to provide novel compositions useful in capturing multiple specific RNA molecules using multiple corresponding capture probes, each probe containing RNA specific barcode sequence flanked by common sequences so they can be used in multiplex amplification reactions with common primers.

In some embodiments the methods use two steps to convert the target RNA into a product that includes a corresponding barcode sequence. In the first step, after specific hybridization between a capturing oligonucleotide (probe) and the RNA target sequence and using captured RNA as primer, the sequence information is copied from the capture probe by linear DNA synthesis. In the second step, the original capture probe is degraded and the newly synthesized linear molecule containing copied barcode sequence is used for detection.

Accordingly, in a first aspect, the disclosure provides methods of detecting RNA levels by which RNA molecules contact a capture probe under conditions that support its specific hybridization of the probe to the target RNA. In some embodiments, the capture probe molecule is a DNA oligonucleotide containing cleavable nucleotides. According to some embodiments capture probe is DNA, and in other embodiments probe is RNA, yet in other embodiments probe is compose of mixture deoxyribonucleotides and ribonucleotides.

In the next step, one or more nucleotides complementary to corresponding nucleotides present in the capture probe are added sequentially to the end of captured RNA, resulting in the formation of an extended linear amplification molecule. In some embodiments, addition of complementary nucleotides is carried out using a DNA polymerase which can extend from ribonucleotide primer.

In the next step, capture probe is destroyed by cleavage in cleavable sites. In some embodiments the uracil base is used and cleaved by uracil glucosidase (UDG).

In another aspect, the capture probe contains the barcode sequence flanked by common sequences. After DNA synthesis the genetic information is copied from captured probe into newly synthesized linear molecule.

In last step, the newly synthesized linear molecule is used as template in an exponential amplification reaction, such as PCR. Where multiple amplifications are desired to be carried out in parallel in the same reaction, common primers can be used in the PCR.

In another aspect, a method for specific selection of RNA molecule with defined 3' end is provided. In the first step, a RNA molecule with defined 3' end contacts to capture probe under conditions that support its specific hybridization thereto. In the next step, additional oligonucleotide, which can hybridize to the probe in the area adjacent to 3' end of the RNA molecule, is added resulting in the formation of a duplex molecule with the nick. In the next step, the nick is closed by ligation covalently attaching RNA molecule to the oligonucleotide. The new hybrid molecule can use as primer for DNA synthesis using a DNA polymerase which can extend only from deoxyribonucleotide primer. Only RNA molecules forming duplex molecule with perfect nick will be selected. In an optional last step, the higher temperature can be use to select longer ligated hybrid primer.

In another aspect, an alternative selection of RNA molecule with a defined 3' end is disclosed. In the first step, a RNA molecule with defined 3' end contacts to capture probe under conditions that support its specific hybridization thereto. The capture probe has the definitive sequence adjacent to 3' end of the RNA molecule. The adjacent sequence composes of one base homopolymer. Addition of corresponding single nucleotide will ensure the extension of the RNA primer and generation longer hybrid molecule, which can be selected by higher temperature and usage of DNA polymerase extending from deoxyribonucleotide primer.

In another aspect, the capture probe contains barcode sequences flanked by two sequences, which use the primers directed toward each other, and newly synthesized linear molecule can be used directly for amplification by PCR.

In another aspect, the method of using capture probe with common sequences for the primers forwarding in the same direction is disclosed. In first step, after specific hybridization between a capturing oligonucleotide (probe) and the specific ribonucleic nucleic acid sequence (RNA), the captured RNA is extended and coping genetic information from captured probe by linear DNA synthesis. In second step, the sequence near 5' end of capture probe is degraded with generation the overhang 3' end of newly synthesized linear molecule. Under specific conditions suitable for intra-molecular interaction the recessed 5' end of the capture probe is ligated to overhang 3' end of linear molecule with formation of loop structure. In new structure the barcode sequence is flanked by primer sequences which are forwarding to each another and can be amplified by PCR.

In another aspect, methods of using capture probe with common sequences for the one primer and subsequent attachment of second primer sequence after synthesis of linear molecule are disclosed. In first step, after specific hybridization between a capturing oligonucleotide (probe) and the specific RN sequence, the captured RNA is extended and coping genetic information from captured probe by linear DNA synthesis. In second step, the second primer is ligated to either 3' end of the newly synthesized linear molecule or to 5' end of the capture probe. In new structure the barcode sequence is flanked by primer sequences which are forwarding to each another and can be amplified by PCR. The ligation of the second primer to 3' end of the newly synthesized linear molecule can be archived by variety known to art methods.

In another aspect, an alternative method for attaching of second primer sequence at 3' end of the newly synthesized linear molecule by DNA synthesis is disclosed. After formation of extended linear molecule the second probe is hybridized at or near 3' end area. The second probe contains template specific sequence 3' end and second primer sequence at 5' end. The second probe forms completely paired duplex with 3' end of newly synthesized linear molecule. By extending recessed 3' end of linear molecule using second probe as template the complementary sequence is added at 3' end of the linear molecule. The added sequence is used as second primer site for amplification by PCR. If the second probe anneals near 3' end of the linear molecule, the single stranded portion of 3' end of newly synthesized linear molecule is degraded by exonuclease or endonuclease activity with formation of recessed 3' end.

In another aspect, a method for measuring levels of regular RNA molecules, significantly degraded RNA, and damaged or modified RNA molecules which can not be used as template for cDNA synthesis is disclosed. Additional step is added to convert captured RNA molecule into extendable RNA primer. After specific hybridization between a capturing oligonucleotide (probe) and the specific ribonucleic nucleic acid sequence (RNA) the complex between probe and RNA molecule is treated with ribonuclease activity which degrades non hybridized portion of RNA molecule. For example this can be archived by using RNase I, RNase A, RNase V1, or T1 or other type of RNase activity degrading single strand RNA molecule. In next step, the DNA polymerase with 3' to 5' activity is added to remove the mispaired bases at the 3' end of the RNA molecule with generation of extendable RNA primer. In followed steps the sequence information is copied from captured probe by linear DNA synthesis. The newly synthesized linear molecule can be amplified using PCR as described above.

In another aspect, an alternative method for generation of extendable RNA primer by using RNase H nicking activity is provided. According to alternative embodiment, the complex between capturing oligonucleotide probe and the specific ribonucleic acid sequence (RNA) is treated by RNase H like activity. RNase H recognizes the RNA-DNA duplex molecule and generates the nicks in RNA strand of the duplex. In next step, the nicked RNA is used as the RNA primer by DNA polymerase I activity, and the sequence information is copied from captured probe by DNA synthesis. The newly synthesized linear molecule can be amplified using PCR as described above.

In yet other embodiments, biotinylated nucleotides are either incorporated into the linear amplification molecule. Thereafter, a streptavidin coated substrate is used to purify biotinylated complexes away from original probe molecules.

According to alternative embodiments, capture probe further comprising a barcode sequence, i.e., a unique pattern of nucleotides that uniquely identifies the linear amplification molecule with which it is associated is disclosed.

In another aspect, the present disclosure provides methods of amplification with a single primer. According to this embodiment, the sequences which are used to amplify linear molecule are comprise of the same composition so single primer used for PCR amplification. In another embodiment, newly synthesized linear molecule is circularized, and single primers are used for rolling cycle amplification.

In another aspect, alternative methods of amplification of linear molecule are disclosed. According to this embodiment capture probe contains T7, T3 or other RNA polymerase primer sequences, so linear molecule can be amplified by RNA transcription.

BRIEF DESCRIPTION OF THE DRAWINGS

The above and other objects and advantages of the disclosed methods will be apparent upon consideration of the following detailed description taken in conjunction with the accompanying drawings, in which like characters refer to like parts throughout. In the representations herein, dotted vertical lines extending between hybridized nucleic acid strands are intended to indicate base pairing generally; the number of lines is not intended to reflect any specific number of basepairs.

FIG. 1A is a schematic illustrating a method for attaching a first oligonucleotide directly to a single-stranded nucleic acid template by extending the 3' end of first oligonucleotide by template directed DNA synthesis.

FIG. 1B shows hybridization of an oligonucleotide to the extension product from FIG. 1A followed by degradation of the single stranded 3' end of the newly synthesized extension product to generate a 3' recessed end.

FIG. 2A is a schematic illustrating the template based extension of the capture probe to form an extension product having sequence complementary to the target.

FIG. 2B is a schematic illustrating hybridization of an oligonucleotide to an internal region of the extension product followed by degradation at the 3' end to form a recessed 3' end.

FIG. 2C is a schematic illustrating how the oligonucleotide brings the 5' and 3' ends of the extension product together for ligation to form a circle.

FIG. 3B illustrates hybridization of the oligonucleotide (probe) directly to the newly synthesized single-stranded linear molecule and degradation of the single stranded 3' end of the newly synthesized linear molecule to generate a 3' recessed end.

FIG. 4 illustrates an alternative method where the second primer sequence is added by extension of the linear extension product after hybridization of an oligonucleotide to the 3' end of the extension product and the resulting product.

FIG. 7A is a schematic illustrating a method for appending small RNA molecule directly to a single stranded capturing oligonucleotide (probe) by hybridizing the RNA to the capture probe and extending the RNA using the capture probe as template.

FIG. 7B shows the extension product with priming sites P1 and P2 and the removal of the capture probe.

FIG. 8B shows extension of the 3' end of the hybrid RNA-DNA primer by DNA polymerase followed by separation of the duplex.

FIG. 9B shows cleavage at the multiple cleavage sites at the 5' end of the capture probe.

FIG. 9C shows intra-molecular looping between the recessed 5' end of the degraded probe and the overhang of the linear molecule followed by ligation.

FIG. 10C illustrates the intra-molecular looping between recessed 5' end of the degraded probe and the overhang 3' end of the linear molecule and the ligation of the 5' end of the degraded probe to the 3' end of the linear molecule.

FIG. 11A is a schematic representation illustrating using a capture probe containing only one primer sequence and attaching second primer sequence by ligation.

FIG. 12A is a schematic representation illustrating a method for using capture probe containing only one primer sequence and attaching a second primer sequence by ligation of an adapter after cleavage with an introduced restriction site.;

FIG. 13A is a schematic representation illustrating a method for using capture probe containing one primer sequence and attaching second primer sequence by ligation.

FIG. 13B shows the hybridization of a splint oligo to which the second primer sequence hybridizes so that it can be ligated to the 3' end of the extension product.

FIG. 14A illustrates extension of a small RNA hybridized to a capture probe and then denaturation of the duplex to form a single stranded extension product.

FIG. 18C shows cleavage of the ligated probes from FIG. 18B followed by labeling of one of the ends created by cleavage.

DETAILED DESCRIPTION OF THE INVENTION

Figure 1C:
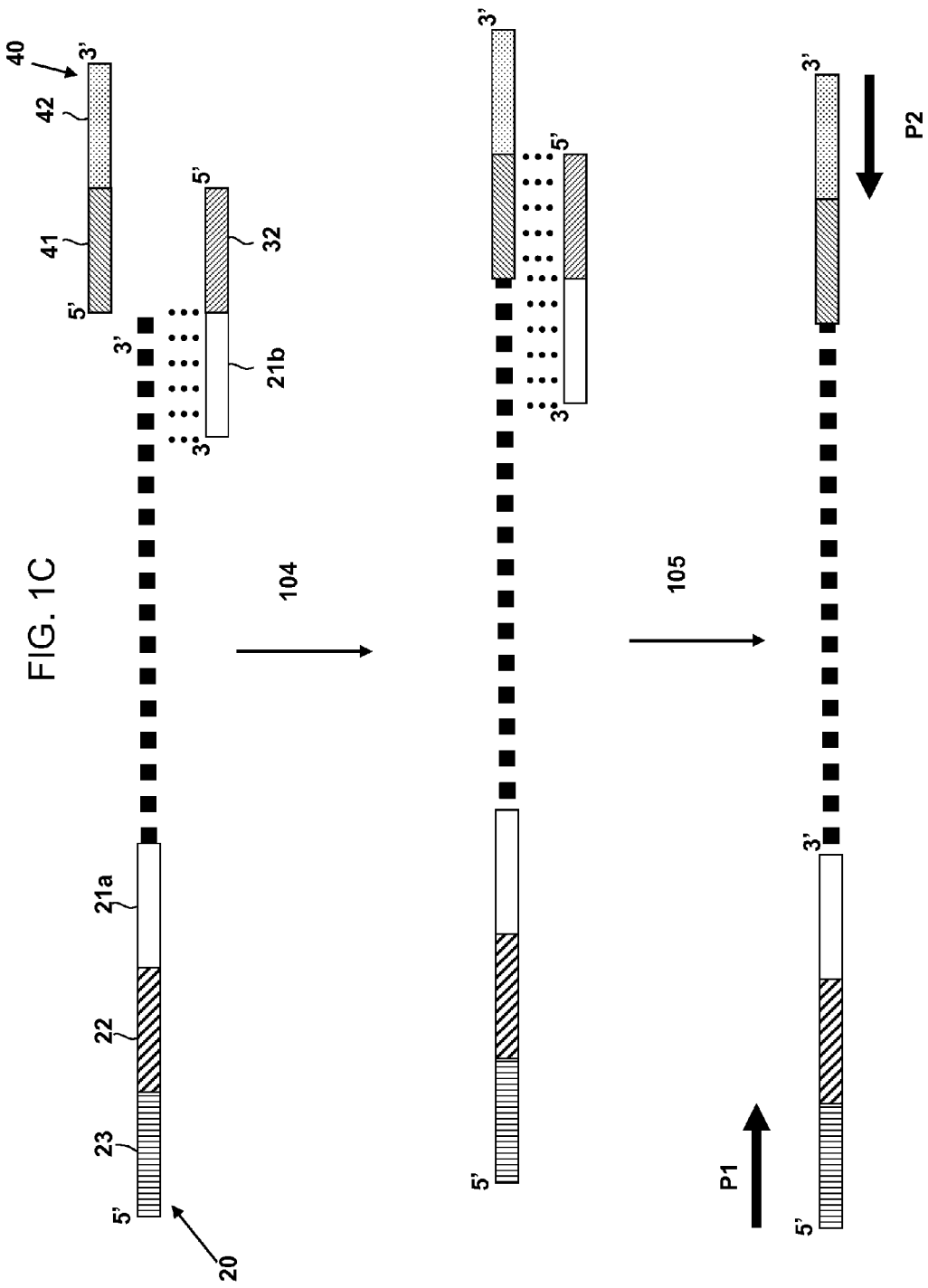
FIG. 1C shows ligation of an oligonucleotide containing a second primer sequence to the 3' end of the extension product and the resulting product suitable for PCR amplification.

Reference will now be made in detail to exemplary embodiments of the invention. While the invention will be described in conjunction with the exemplary embodiments, it will be understood that they are not intended to limit the invention to these embodiments. On the contrary, the invention is intended to cover alternatives, modifications and equivalents, which may be included within the spirit and scope of the invention.

The disclosed methods have many preferred embodiments and rely on many patents, applications and other references for details known to those of the art. Therefore, when a patent, application, or other reference is cited or repeated below, it should be understood that it is incorporated by reference in its entirety for all purposes as well as for the proposition that is recited.

As used in this application, the singular form "a," "an," and "the" include plural references unless the context clearly dictates otherwise. For example, the term "an agent" includes a plurality of agents, including mixtures thereof.

An individual is not limited to a human being but may also be other organisms including but not limited to mammals, plants, bacteria, or cells derived from any of the above.

Throughout this disclosure, various aspects of this invention can be presented in a range format. It should be understood that the description in range format is merely for convenience and brevity and should not be construed as an inflexible limitation on the scope of the invention. Accordingly, the description of a range should be considered to have specifically disclosed all the possible subranges as well as individual numerical values within that range. For example, description of a range such as from 1 to 6 should be considered to have specifically disclosed subranges such as from 1 to 3, from 1 to 4, from 1 to 5, from 2 to 4, from 2 to 6, from 3 to 6 etc., as well as individual numbers within that range, for example, 1, 2, 3, 4, 5, and 6. This applies regardless of the breadth of the range. All references to the function log default to e as the base (natural log) unless stated otherwise (such as log.sub.10).

The practice of the disclosed methods may employ, unless otherwise indicated, conventional techniques and descriptions of organic chemistry, polymer technology, molecular biology (including recombinant techniques), cell biology, biochemistry, and immunology, which are within the skill of the art. Such conventional techniques include polymer array synthesis, hybridization, ligation, and detection of hybridization using a label. Specific illustrations of suitable techniques can be had by reference to the example herein below. However, other equivalent conventional procedures can, of course, also be used. Such conventional techniques and descriptions can be found in standard laboratory manuals such as Genome Analysis: A Laboratory Manual Series (Vols. I-IV), Using Antibodies: A Laboratory Manual, Cells: A Laboratory Manual, PCR Primer: A Laboratory Manual, and Molecular Cloning: A Laboratory Manual (all from Cold Spring Harbor Laboratory Press), Stryer, L. (1995) Biochemistry (4th Ed.) Freeman, New York, Gait, "Oligonucleotide Synthesis: A Practical Approach" 1984, IRL Press, London, Nelson and Cox (2000), Lehninger, Principles of Biochemistry 3.sup.rd Ed., W.H. Freeman Pub., New York, N.Y. and Berg et al. (2002) Biochemistry, 5.sup.th Ed., W.H. Freeman Pub., New York, N.Y., all of which are herein incorporated in their entirety by reference for all purposes.

The methods can employ solid substrates, including arrays in some preferred embodiments. Methods and techniques applicable to polymer (including protein) array synthesis have been described in U.S. Ser. No. 09/536,841 (now abandoned), WO 00/58516, U.S. Pat. Nos. 5,143,854, 5,242,974, 5,252,743, 5,324,633, 5,384,261, 5,405,783, 5,424,186, 5,451,683, 5,482,867, 5,491,074, 5,527,681, 5,550,215, 5,571,639, 5,578,832, 5,593,839, 5,599,695, 5,624,711, 5,631,734, 5,795,716, 5,831,070, 5,837,832, 5,856,101, 5,858,659, 5,936,324, 5,968,740, 5,974,164, 5,981,185, 5,981,956, 6,025,601, 6,033,860, 6,040,193, 6,090,555, 6,136,269, 6,269,846 and 6,428,752, in PCT Applications Nos. PCT/US99/00730 (International Publication Number WO 99/36760) and PCT/US01/04285, and U.S Patent Pub. 20050074787 (now abandoned), which are all incorporated herein by reference in their entirety for all purposes. Patents that describe synthesis techniques in specific embodiments include U.S. Pat. Nos. 5,412,087, 6,147,205, 6,262,216, 6,310,189, 5,889,165, and 5,959,098. Nucleic acid arrays are described in many of the above patents, but the same techniques are applied to polypeptide arrays.

The disclosure also contemplates many uses for polymers attached to solid substrates. These uses include gene expression monitoring, profiling, library screening, genotyping and diagnostics. Gene expression monitoring, and profiling methods can be shown in U.S. Pat. Nos. 5,800,992, 6,013,449, 6,020,135, 6,033,860, 6,040,138, 6,177,248 and 6,309,822. Genotyping and uses therefore are shown in U.S. Pat. Pub. No. 20070065816 (now abandoned) and U.S. Pat. Nos. 5,856, 092, 6,300,063, 5,858,659, 6,284,460, 6,361,947, 6,368,799, 6,872,529 and 6,333,179. Other uses are embodied in U.S. Pat. Nos. 5,871,928, 5,902,723, 6,045,996, 5,541,061, and 6,197,506.

The disclosure also contemplates sample preparation methods in certain preferred embodiments. Prior to or concurrent with genotyping, the genomic sample may be amplified by a variety of mechanisms, some of which may employ PCR. See, e.g., PCR Technology: Principles and Applications for DNA Amplification (Ed. H. A. Erlich, Freeman Press, NY, N.Y., 1992); PCR Protocols: A Guide to Methods and Applications (Eds. Innis, et al., Academic Press, San Diego, Calif., 1990); Mattila et al., Nucleic Acids Res. 19, 4967 (1991); Eckert et al., PCR Methods and Applications 1, 17 (1991); PCR (Eds. McPherson et al., IRL Press, Oxford); and U.S. Pat. Nos. 4,683,202, 4,683,195, 4,800,159 4,965,188 and 5,333,675, and each of which is incorporated herein by reference in their entireties for all purposes. The sample may be amplified on the array. See, for example, U.S. Pat. No. 6,300, 070 and U.S. patent application Ser. No. 09/513,300, which are incorporated herein by reference.

Other suitable amplification methods include the ligase chain reaction (LCR) (for example, Wu and Wallace, Genomics 4, 560 (1989), Landegren et al., Science 241, 1077 (1988) and Barringer et al. Gene 89:117 (1990)), transcription amplification (Kwoh et al., Proc. Natl. Acad. Sci. USA 86, 1173 (1989) and WO88/10315), self-sustained sequence replication (Guatelli et al., Proc. Nat. Acad. Sci. USA, 87, 1874 (1990) and WO90/06995), selective amplification of target polynucleotide sequences (U.S. Pat. No. 6,410,276), consensus sequence primed polymerase chain reaction (CP-PCR) (U.S. Pat. No. 4,437,975), arbitrarily primed polymerase chain reaction (AP-PCR) (U.S. Pat. Nos. 5,413,909, 5,861, 245) and nucleic acid based sequence amplification (NASBA). (See, U.S. Pat. Nos. 5,409,818, 5,554,517, and 6,063,603, each of which is incorporated herein by reference). Other amplification methods that may be used include: Qbeta Replicase, described in PCT Patent Application No. PCT/US87/00880, isothermal amplification methods such as SDA, described in Walker et al. 1992, Nucleic Acids Res. 20(7):1691-6, 1992, and rolling circle amplification, described in U.S. Pat. No. 5,648,245. Other amplification methods that may be used are described in, U.S. Pat. Nos. 5,242,794, 5,494,810, 4,988,617 and 6,582,938 and US Pub. No. 7,655,791, each of which is incorporated herein by reference. In some embodiments DNA is amplified by multiplex locus-specific PCR. In a preferred embodiment the DNA is amplified using adaptor-ligation and single primer PCR. Other available methods of amplification, such as balanced PCR (Makrigiorgos, et al. (2002), Nat Biotechnol, Vol. 20, pp. 936-9), may also be used.

Additional methods of sample preparation and techniques for reducing the complexity of a nucleic sample are described in Dong et al., Genome Research 11, 1418 (2001), in U.S. Pat. Nos. 6,361,947, 6,391,592, 6,632,611, 6,872,529, and 6,958, 225 and U.S. application Ser. No. 09/916,135 (now abandoned).

Methods for conducting polynucleotide hybridization assays have been well developed in the art. Hybridization assay procedures and conditions will vary depending on the application and are selected in accordance with the general binding methods known including those referred to in: Maniatis et al. Molecular Cloning: A Laboratory Manual (2.sup.nd Ed. Cold Spring Harbor, N.Y., 1989); Berger and Kimmel Methods in Enzymology, Vol. 152, Guide to Molecular Cloning Techniques (Academic Press, Inc., San Diego, Calif., 1987); Young and Davism, P.N.A.S, 80: 1194 (1983). Methods and apparatus for carrying out repeated and controlled hybridization reactions have been described in U.S. Pat. Nos. 5,871,928, 5,874,219, 6,045,996 and 6,386,749, 6,391,623 each of which are incorporated herein by reference.

The disclosure also contemplates signal detection of hybridization between ligands in certain preferred embodiments. See U.S. Pat. Nos. 5,143,854, 5,578,832; 5,631,734; 5,834,758; 5,936,324; 5,981,956; 6,025,601; 6,141,096; 6,185,030; 6,201,639; 6,218,803, 6,225,625, 7,689,022 and 7,871,812 and in PCT Application PCT/US99/06097 (published as WO99/47964), each of which also is hereby incorporated by reference in its entirety for all purposes.

Methods and apparatus for signal detection and processing of intensity data are disclosed in, for example, U.S. Pat. Nos. 5,143,854, 5,547,839, 5,578,832, 5,631,734, 5,800,992, 5,834,758; 5,856,092, 5,902,723, 5,936,324, 5,981,956, 6,025,601, 6,090,555, 6,141,096, 6,185,030, 6,201,639, 6,218,803, 6,225,625, 7,689,022 and 7,871,812 and in PCT Application PCT/US99/06097 (published as WO99/47964), each of which also is hereby incorporated by reference in its entirety for all purposes.

The practice of the methods may also employ conventional biology methods, software and systems. Computer software products of the invention typically include computer readable medium having computer-executable instructions for performing the logic steps of the method of the invention. Suitable computer readable medium include floppy disk, CD-ROM/DVD/DVD-ROM, hard-disk drive, flash memory, ROM/RAM, magnetic tapes and etc. The computer executable instructions may be written in a suitable computer language or combination of several languages. Basic computational biology methods are described in, e.g. Setubal and Meidanis et al, Introduction to Computational Biology Methods (PWS Publishing Company, Boston, 1997); Salzberg, Searles, Kasif, (Ed.), Computational Methods in Molecular Biology, (Elsevier, Amsterdam, 1998); Rashidi and Buehler, Bioinformatics Basics: Application in Biological Science and Medicine (CRC Press, London, 2000) and Ouelette and Bzevanis Bioinformatics: A Practical Guide for Analysis of Gene and Proteins (Wiley & Sons, Inc., 2nd ed., 2001). The methods may also make use of various computer program products and software for a variety of purposes, such as probe design, management of data, analysis, and instrument operation. See, U.S. Pat. Nos. 5,593,839, 5,795,716, 5,733,729, 5,974,164, 6,066,454, 6,090,555, 6,185,561, 6,188,783, 6,223,127, 6,229,911, 6,804,679 and 6,308,170. Computer methods related to genotyping using high density microarray analysis may also be used in the present methods, see, for example, U.S. Pat. No. 7,202,039 and US Patent Pub. Nos. 20050250151 (now U.S. Pat. No. 7,280,922), 20050244883 (now abandoned), 20050108197 (now abandoned) and 20050042654 (now abandoned). Related methods for preparing and analyzing nucleic acids on arrays are disclosed, for example, in US Patent Publication Nos. 20060134652 (now abandoned), which discloses methods for fragmenting cDNA prepared from RNA using uracil incorporation, 20050106591 (now abandoned) which discloses methods of preparing cDNA from RNA using random primers attached to an RNA polymerase promoter, The practice of the methods may employ, unless otherwise indicated, conventional techniques and descriptions of organic chemistry, polymer technology, molecular biology (including recombinant techniques), cell biology, biochemistry, and immunology, which are within the skill of the art. Such conventional techniques include polymer array synthesis, hybridization, ligation, and detection of hybridization using a label. Specific illustrations of suitable techniques can be had by reference to the example herein below. However, other equivalent conventional procedures can, of course, also be used. Such conventional techniques and descriptions can be found in standard laboratory manuals such as Genome Analysis: A Laboratory Manual Series (Vols. I-IV), Using Antibodies: A Laboratory Manual, Cells: A Laboratory Manual, PCR Primer: A Laboratory Manual, and Molecular Cloning: A Laboratory Manual (all from Cold Spring Harbor Laboratory, Press), Stryer L. (1995) Biochemistry (4th Ed.) Freeman, New York, Gait, "Oligonucleotide Synthesis: A Practical Approach" 1984, IRL Press, London, Nelson and Cox (2000), Lehninger, Principles of Biochemistry 3.sup.rd Ed., W.H. Freeman Pub., New York, N.Y. and Berg et al. (2002) Biochemistry 5.sup.th Ed., W.H. Freeman Pub., New York, N.Y., all of which are herein incorporated in their entirety by reference for all purposes.

"Complementary" or "substantially complementary" refers to the hybridization or base pairing or the formation of a duplex between nucleotides or nucleic acids, such as, for instance, between the two strands of a double stranded DNA molecule or between an oligonucleotide primer and a primer binding site on a single stranded nucleic acid. Complementary nucleotides are, generally, A and T (or A and U), or C and G. Two single stranded RNA or DNA molecules are said to be substantially complementary when the nucleotides of one strand, optimally aligned and compared and with appropriate nucleotide insertions or deletions, pair with at least about 80% of the nucleotides of the other strand, usually at least about 90% to 95%, and more preferably from about 98 to 100%. Alternatively, substantial complementarity exists when an RNA or DNA strand will hybridize under selective hybridization conditions to its complement. Typically, selective hybridization will occur when there is at least 65% complementary over a stretch of at least 14 to 25 nucleotides, preferably at least about 75%, more preferable at least about 90% complementary. See, M. Kanehisa Nucleic Acids Res. 12:203 (1984), incorporated herein by reference.

"Complexity" or "complex" in reference to mixtures of nucleic acids means the total length of unique sequences in the mixture. In reference to genomic DNA, complexity means the total length of unique sequence DNA in a genome. The complexity of a genome can be equivalent to or less than the length of a single copy of the genome (i.e. the haploid sequence). Estimates of genome complexity can be less than the total length if adjusted for the presence of repeated sequences. In other words, in reference to genomic DNA, "complexity" means the total number of basepairs present in non-repeating sequences, e.g. Wetmur, Critical Reviews in Biochemistry and Molecular Biology, 26:227-259 (1991); Britten and Davidson, chapter 1 in Hames et al, editors, Nucleic Acid Hybridization: A Practical Approach (IRL Press, Oxford, (1985).

"Duplex" means at least two oligonucleotides and/or polynucleotides that are fully or partially complementary undergo Watson-Crick type base pairing among all or most of their nucleotides so that a stable complex is formed. The terms "annealing" and "hybridization" are used interchangeably to mean the formation of a stable duplex. In one aspect, stable duplex means that a duplex structure is not destroyed by a stringent wash, e.g. conditions including temperature of about 5.degree. C. less that the T.sub.m of a strand of the duplex and low monovalent salt concentration, e.g. less than 0.2 M, or less than 0.1 M. "Perfectly matched" in reference to a duplex means that the poly- or oligonucleotide strands making up the duplex from a double Watson-Crick basepairing with a nucleotide in the other strand. The term "duplex" comprehends the pairing of nucleoside analogs, such as deoxyinosine, nucleosides with 2-aminopurine bases, PNAs, and the like, that may be employed. A "mismatch" in a duplex between two oligonucleotides or polynucleotides means that at pair of nucleotides in the duplex fails to undergo Watson-Crick bonding.

"Hybridization" refers to the process in which two single-stranded polynucleotides bind non-covalently to form a stable double-stranded polynucleotide. The term "hybridization" may also refer to triple-stranded hybridization. The resulting (usually) double-stranded polynucleotide is a "hybrid" or "duplex." "Hybridization conditions" will typically include salt concentrations of less than about 1 M, more usually less than about 500 mM or less than about 200 mM. Hybridization temperatures can be as low as 5° C. but are typically greater than 22° C. more typically greater than about 30° C., and preferably in excess of about 37° C.

Hybridizations are usually performed under stringent conditions, i.e. conditions under which a probe will hybridize to its target subsequence. Stringent conditions are sequence-dependent and are different in different circumstances. Longer fragments may require higher hybridization temperatures for specific hybridization. As other factors may affect the stringency of hybridization, including base composition and length of the complementary strands, presence of organic solvents and extent of base mismatching, the combination of parameters is more important than the absolute measure of any one alone. Generally, stringent conditions are selected to be about 5° C. lower than the $T_m$ for the specific sequence at s defined ionic strength and pH. Exemplary stringent conditions include salt concentration of at least 0.01 M to no more than 1 M Na ion concentration (or other salts) at a pH 7.0 to 8.3 and a temperature of at least 25° C. For example, conditions of 5×SSPE (750 mM NaCl, 5.0 mM NaPhosphate, 5 mM EDTA, pH 7.4) and a temperature of 25-30° C. are suitable for allele-specific probe hybridizations. For stringent conditions, see for example, Sambrook, Fritsche and Maniatis. "Molecular Cloning A Laboratory Manual" 2.sup.nd Ed. Cold Spring Harbor Press (1989) and Anderson "Nucleic Acid Hybridization" 1st Ed. BIOS Scientific Publishers Limited (1999), which are hereby incorporated by reference in its entirety for all purposes above. "Hybridizing specifically to" or "specifically hybridizing to" or like expressions refer to the binding, duplexing, or hybridizing of a molecule substantially to or only to a particular nucleotide sequence or sequences under stringent conditions when that sequence is present in a complex mixture (e.g., total cellular) DNA or RNA.

"Hybridization-based assay" means any assay that relies on the formation of a stable duplex or triplex between a probe and a target nucleotide sequence for detecting or measuring such a sequence. In one aspect, probes of such assays anneal to (or form duplexes with) regions of target sequences in the range of from 8 to 100 nucleotides; or in other aspects, they anneal to target sequences in the range of from 8 to 40 nucleotides, or more usually, in the range of from 8 to 20 nucleotides.

A "probe" in reference to a hybridization-based assay refers to a polynucleotide that has a sequence that is capable of forming a stable hybrid (or triplex) with its complement in a target nucleic acid and that is capable of being detected, either directly or indirectly. Hybridization-based assays include, without limitation, assays based on use of oligonucleotide, such as polymerase chain reactions, NASBA reactions, oligonucleotide ligation reactions, single-based extensions of primers, circularizable probe reactions, allele-specific oligonucleotides hybridizations, either in solution phase in solution phase or bound to solid phase supports, such as microarrays or microbeads. There is extensive guidance in the literature on hybridization-based assays, e.g. Hames et al, editors, Nucleic Acid Hybridization a Practical Approach (IRL Press, Oxford, 1985), Tijssen, Hybridization with Nucleic Acid Probes, Parts I & II (Elsevier Publishing Company, 1993); Hardiman, Microarray Methods Applications (DNA Press, 2003); Schena, editor, DNA Microarrays a Practical Approach (IRL Press, Oxford, 1990); and the like. In one aspect, hybridization-based assays are solution phase assays; that is, both probes and target sequences hybridize under conditions that are substantially free of surface effects influences on reaction rate. A solution phase assay may include circumstances where either probes or target sequences are attached to microbeads.

"Ligation" means to form a convalent bond or linkage between the termini of two or more nucleic acids, e.g. oligonucleotide and/or polynucleotide, in a template-driven reaction. The nature of the bond or linkage may vary widely and the ligation may be carried out enzymatically or chemically. As used herein, ligations are usually carried out enzymatically to form a phosphodiester linkage between a 5' carbon of a terminal nucleotide of one oligonucleotide with 3' carbon of another oligonucleotide. A variety of template-driven ligation reactions are described in the following references, which are incorporated by reference: Whitely et al, U.S. Pat. No. 4,883,750; Letsinger et al, U.S. Pat. No. 5,476,930; Fung et al, U.S. Pat. No. 5,593,826; Kool, U.S. Pat. No. 5,426,180; Landegren et al, U.S. Pat. No. 5,871,921; Xu and Kool, Nucleic Acids Research, 27:875-881 (1999); Higgins et al, Methods in Enzymology, 68:50-71 (1979); Engler et al. The Enzymes. 15:3-29 (1982); and Namsaraev, U.S. patent publication 20040110213 (now abandoned).

"Microarray" refers to a solid phase support having a planar surface, which carries an array of nucleic acids, each member of the array comprising identical copies of an oligonucleotide or polynucleotide immobilized to a spatially defined region or site, which does not overlap with those of other members of the array; that is, the regions or sites are spatially discrete. Spatially defined hybridization sites may additionally be "addressable" in that its location and the identity of its immobilized oligonucleotide are known, predetermined, or determinable. Typically, the oligonucleotides or polynucleotides are single stranded and are covalently attached to thee solid phase support usually by a 5'-end or a 3'-end. The density of non-overlapping regions containing nucleic acids in a microarray is typically greater than 100 per cm.sup.2, and more preferably, greater than 1000 per $cm^2$. Microarray technology is reviewed in the following references. Schena, Editor, Microarray. A Practical Approach (IRL Press, Oxford, 2000); Southern, Current Opin. Chem. Biol., 2:404-410 (1998); Nature Genetics Supplement, 21:1-60 (1999). As used herein, "random microarray" refers to a microarray whose spatially discrete regions of oligonucleotides or polynucleotides are not spatially addressed, absent a decoding step to identify the sequence of an immobilized oligonucleotide. That is, the identity of the attached oligonucleotides or polynucleotides is not discernable, at least initially, from its location; it requires a decoding step to determine which probe or tag hybridizes to which site. In one aspect, random microarrays are planar arrays of microbeads wherein each microbead has attached a single kind of hybridization tag complement, such as from a minimally cross-hybridizing set of oligonucleotides. Arrays of microbeads may be formed in a variety of ways, e.g. Brenner et al, Nature Biotechnology 18:630-634 (2000); Tulley, et al, U.S. Pat. No. 6,133,043; Stuelpnagel et al, U.S. Pat. No. 6,396,995; Chee et al, U.S. Pat. Nos. 6,544,732; 6,620,584; and the like. Likewise, microbeads solid supports e.g. in a random array, may be identified, or addressable, in a variety of ways, including by optical labels, e.g. fluoresecnt dye ratios or quantum dots, shape, sequence analysis, radio frequency identification tags, or the like.

"Nucleoside" as used herein includes the natural nucleosides, including 2'-deoxy and 2'-hydroxyl forms, e.g. as described in Komberg and Baker. DNA Replication, 2nd Ed. (Freeman, San Francisco, 1992). "Analogs" in reference to nucleosides includes synthetic nucleosides having modified base moieties and/or modified sugar moieties, e.g. described by Scheit, Nucleotide Analogs (John Wiley, New York, 1980): Uhlman and Peyman, Chemical Reviews, 90:543-584 (1990), or the like, with the proviso that they are capable of specific hybridization. Such analogs include synthetic nucleosides designed to enhance binding properties, reduce complexity, increase specificity, and the like. Polynucleotides comprising analogs with enhanced hybridization or nuclease resistance properties are described in Uhlman and Peyman (cited above): Crooke et al, Exp. Opin. Ther. U.S. Pat. No. 6,855,870 (1996), Mesmacker et al, Current Opinion in Structured Biology, 5:343-355 (1995); and the like. Exemplary types of polynucleotides that are capable of enhancing duplex stability include oligonucleotide N3'+.fwdarw.P5' phosphoramidates (referred to herein as "amidates"), peptide nucleic acids (referred to herein as "PNAs"), oligo-2'-O-alkylribonucleotides, polynucleotides containing C-5 propynlpyrimidines, locked nucleic acids (LNAs), an like compounds. Such oligonucleotides are either available commercially or may be Synthesized using methods described in the literature.

"Decoding sequence" means an oligonucleotide that is attached to a polynucleotide and is used to identify and/or track the polynucleotide in a reaction. Usually, a oligonucleotide tag is attached to the 3'- or 5'-end of a polynucleotide to form a linear conjugate, sometime referred to herein as a "barcode polynucleotide," or "tag polynucleotide" equivalently, a "oligonucleotide tag-polynucleotide conjugate," or "tag-polynucleotide conjugate." Oligonucleotide barcodes may vary widely in size and compositions; the following references provide guidance for selecting sets of oligonucleotide barcodes appropriate for particular embodiments: Brenner, U.S. Pat. No. 5,635,400; Brenner et al, Proc. Natl. Acad. Sci. 97:1665-1670 (2000), Shoemaker et al, Nature Genetics, 14:450-456 (1996); Morris et al, European patent publication 0799897A1; Wallace, U.S. Pat. No. 5,981,179; and the like. In different applications of the invention, oligonucleotide barcodes can each have a length within a range of from 4 to 36 nucleotides, or from 6 to 30 nucleotides, or from 8 to 20 nucleotides, respectively. In one aspect, oligonucleotide barcodes are used in sets, or repertoires, wherein each oligonucleotide barcode of the set has a unique nucleotide sequence. In some embodiment, particularly where oligonucleotide barcodes are used to sort polynucleotides, or where they are identified by specific hybridization, each oligonucleotide barcode of such a set has a melting temperature that is substantially the same as that of every other member of the same set. In such aspects, the melting temperatures of oligonucleotide barcodes within a set are within 10 degrees C. of one another, in another embodiment, they are within 5 degrees C. of one another; and in another embodiment, they are within 2 degrees C. of one another. In another aspect, oligonucleotide barcodes are members of a mutually discriminable set as described more fully below. The size of mutually discriminable sets of oligonucleotide barcodes may vary widely. Such a set of oligonucleotide barcodes may have a size in the range of from several tens to many thousands, or even millions, e.g. 50 to $1.6 \times 10^6$. In another embodiment, such a size is in the range of from 200 to 40,000; or from 1000 to 40,000; or from 1000 to 10,000. In another aspect of the invention of oligonucleotide barcodes comprise a concatenation of subunits, such as described by Brenner et al, Proc. Natl. Acad. Sci., 97:1665-1670 (2000). In such concatenates, oligonucleotide subunits, or words, can be selected from a set of subunits with the properties of mutual discriminability and substantially equivalent melting temperature. Constructing oligonucleotide barcodes from a plurality of oligonucleotide subunits permits the convenient and inexpensive formation of very large sets of oligonucleotide barcodes e.g. as described by Brenner et al, *Proc. Natl. Acad. Sci.,* 97:1665-1670 (2000). Also, the use of oligonucleotide subunits permits enzymatic synthesis and/or attachment of oligonucleotide barcodes to polynucleotides, e.g. as described below and in Brenner and Williams, U.S. patent publication 20030049616 (now abandoned).

In one aspect, oligonucleotide barcodes comprise a plurality of oligonucleotide subunits. Such subunits may vary widely in length. In one aspect, the length of oligonucleotide subunits is in the range of from 2 to 18 nucleotides; in another aspect, the length of oligonucleotide subunits is in the range of from 2 to 8 nucleotides; and in another aspect the length of oligonucleotide subunits is in the range of from 2 to 5 nucleotides. A plurality of oligonucleotide subunits making up an oligonucleotide barcode may also vary widely depending on their application. In one aspect, such plurality is a number in the range of 2 to 10; and in another aspect, such plurality is a number in the range of from 2 to 6. The size of a set of oligonucleotide subunits is usually smaller than the size of a set of oligonucleotide barcodes. Usually, a set of oligonucleotide subunits has a size in the range from 2 to 20; or in another embodiment, from 2 to 10 or in another embodiment, from 4 to 8. It is clear to one of ordinary skill that for subunit only two nucleotides in length that the size of a set of subunits would be smaller than that of subunits having greater lengths.

"Polymerase chain reactions" or "PCR," means a reaction for the in vitro amplification of specific DNA sequences by the simultaneous primer extension of complementary strands of DNA. In other words, PCR is a reaction for making multiple copies or replicates of a target nucleic acid flanked by primer binding sites, such reaction comprising one or more repetitions of the following steps: (i) denaturing the target nucleic acid, (ii) annealing primers to the primer binding sites, and (iii) extending the primers by a nucleic acid polymerase in the presence of nucleoside triphosphates. Usually the reaction is cycled through different temperatures optimized for each step in a thermal cycler instrument. Particular temperatures, durations at each step, and rates of change, between steps depend on many factor, well-known to those of ordinary skill in the art, e.g. exemplified by the references. McPherson et al, editors, PCR; A Practical Approach and PCR2: A Practical Approach (IRL Press, Oxfold, 1991 and 1995, respectively). For example, in a conventional PCR using Taq DNA polymerase, a double stranded target nucleic acid may be denatured at a temperature, >90.degree.C., primers annealed at a temperature in the range 50-75.degree. C., and primers extended at a temperature in the range 72-78.degree. C.

The term "PCR" encompasses derivative forms of the reaction, including but not limited to, RT-PCR, real-time PCR nested PCR, quantitative PCR, multiplexed PCR, and the like. Reaction volumes range from a few hundred nanoliters e.g. 200 nL, to a few hundred .mu.L, e.g. 200.mu.L. "Reverse transcription PCR," or RT-PCR," means a PCR that is preceded by a reverse transcription reaction that converts a target RNA to a complementary single stranded DNA, which is then amplified e.g. Tecott et al, U.S. Pat. No. 5,168,038, which patent is incorporated herein by reference "Real-time PCR" means a PCR for which the amount of reaction product, i.e. amplicon, is monitored as the reaction proceeds. There are many forms of real-time PCR that differ mainly in the detection chemistries used for monitoring the reaction product, e.g. Gelfand et al, U.S. Pat. No. 5,210,015 ("taqman"); Wittwer et al, U.S. Pat. Nos. 6,174,670 and 6,569,627 (intercalating dyes); Tyagi et al, U.S. Pat. No. 5,925,517 (molecular beacons); which patents are incorporated herein by reference. Detection chemistries for real-time PCR are reviewed in Mackay et al, Nucleic Acids Research, 30:1292-1305 (2002), which is also incorporated herein by reference. "Nested PCR" means a two-stage PCR wherein the amplicon of a first PCR becomes the sample for a second PCR using a new set of primers, at least one of which binds to an interior location of the first amplicon.

As used herein, "initial primers" in reference to a nested amplification reaction mean the primers used to generate a first amplicon, and "secondary primers" mean the one or more primers used to generate a second, or nested amplicon. "Multiplexed PCR" means PCR wherein multiple target sequences (or a single target sequence and one or more reference sequence) are simultaneously carried out in the same reaction mixture, e.g. Bernard et al, Anal. Biochem., 273:221-228 (1999) (two-color real-time PCR). Usually, distinct sets of primers are employed for each sequence being amplified.

"Quantitative PCR" means a PCR designed to measure the abundance of one or more specific target sequences in a sample or specimen. Quantitative PCR includes both absolute quantitation and relative quantitation of such target sequences. Quantitative measurements are made using one or more reference sequences that may be assayed separately or together with a target sequence. The reference sequences may be endogenous or exongenous to a sample or specimen, and in the latter case, may comprise one or more competitor templates. Typical endogenous reference sequences include segments of transcripts of the following genes: beta-actin, GAPDH, beta 2-microglobulin, ribosomal RNA, and the like. Techniques for quantitative PCR are well-known to those of ordinary skill in the art, as exemplified in the following references that are incorporated by reference. Freeman et al, Biotechniques, 26:112-126 (1999); Becker-Andre et al, Nucleic Acids Research, 17:9437-9447 (1989); Zimmerman et al, Biotechniques, 21:268-279 (1996); Diviacco et al, Gene, 122:3013-3020 (1992); Becker-Andre et al, Nucleic Acids Research, 17:9437-9446 (1989); and the like.

"Polynucleotide" and "oligonucleotide" are used interchangeably and each mean a linear polymer of nucleotide monomers. Monomers making up polynucleotides and oligonucleotides are capable of specifically binding to a natural polynucleotide by way of a regular pattern of monomer-to-monomer interactions, such as Watson-Crick type of base pairing, base stacking. Hoogsteen or reverse Hoogsteen types of base pairing, or the like. Such monomers and their internucleotide linkages may be naturally occurring or may be analogs thereof, e.g. naturally occurring or non-naturally occurring analogs. Non-naturally occurring analogs may include PNAs, phosphorothioate internucleosides linkages, bases containing linking groups permitting the attachment of labels, such as fluorophores, or haptens and the like. Whenever the use of an oligonucleotide or polynucleotide requires enzymatic processing, such as extension by a polymerase, ligation by a ligase, or the like, one of ordinary skill would understand that oligonucleotides or polynucleotides in those instances would not contain certain analogs of internucleoside linkages, sugar moities, or bases at any or some positions. Polynucleotides typically range in size from a few monomeric units, e.g. 5-40, when they are usually referred to as "oligonucleotides", to several thousand monomeric units. Whenever a polynucleotide or oligonucleotide is represented by a sequence of letters (upper or lower case), such as "ATGCCTG," it will be understood that the nucleotides are in 5'.fwdarw.3' order from left to right and that "A" denotes deoxyadenosine, "C" denotes deoxcytidine, "G" denotes deoxyguanosine, and "T" denotes thymidine, "I" denotes deoxyinosine, "U" denotes uridine, unless otherwise indicated or obvious from context. Unless otherwise noted the terminology and atom numbering conventions will follow those disclosed in Strachan and Read, Human Molecular Genetics 2 (Wiley-Liss New York 1999). Usually polynucleotides comprise the four natural nucleosides (e.g. deoxyadenosine, deoxycytidine, deoxyguanosine, deoxythymidine for DNA or their ribose counterparts for RNA) linked by phosphodiester linkages; however, they may also comprise non-natural nucleotide analogs, e.g. including modified bases, sugars, or internucleoside linkages. It is clear to those skilled in the art that where an enzyme has specific oligonucleotide or polynucleotide substrate requirements for activity, e.g. single stranded DNA, RNA/DNA duplex, or the like, then selection of appropriate composition for the oligonucleotide or polynucleotide substrates is well within the knowledge of one of ordinary skill, especially with guidance from treatises, such as Sambrook et al, Molecular Cloning, Second Edition (Cold Spring Harbor Laboratory, New York, 1989), and like references.

"Primer" means an oligonucleotide, either natural or synthetic that is capable, upon forming a duplex with a polynucleotide template, of acting as a point of initiation of nucleic acid synthesis and being extended from its 3' end along the template so that an extended duplex is formed. The sequence of nucleotides added during the extension process are determined by the sequence of the template polynucleotide. Usually primers are extended by a DNA polymerase. Primers usually have a length in the range of from 14 to 36 nucleotides. Preferably, primers have a length in the range of from 18 to 24 nucleotides.

"Readout" means a parameter, or parameters, which are measured and/or detected that can be converted to a number or value. In some contexts, readout may refer to an actual numerical representation of such collected or recorded data. For example, a readout of fluoresent intensity signals from a microarray is the address and fluorescene intensity of a signal being generated at each hybridization site of the microarray; thus, such a readout may be registered or stored in various ways, for example, as an image of the microarray, as a table of numbers, or the like. A readout is "digital" when the number or value is obtained by a counting process, e.g. determining a value by counting on a microarray the number of hybridization from which signals are being generated (as distinguished from those sites not generating signals).

"Sample" is used in at least two different contexts in connection with the invention. In one context, "sample," or equivalently "test sample," means a quantity of material from a biological, environmental, medical, or patient source in which detection or measurement of target polynucleotides or nucleic acids is sought. It may include a specimen or culture (e.g., microbiological cultures), or other types of biological or environmental samples. A test sample may include a specimen of synthetic origin. Biological test samples may be animal, including human, fluid, solid (e.g., stool) or tissue, as well as liquid and solid food and feed products and ingredients such as dairy items, vegetables, meat and meat by-products, and waste. Biological test samples may include materials taken from a patient including, but not limited to cultures, blood, saliva, cerebral spinal fluid, pleural fluid, milk, lymph, sputum, semen, needle aspirates, and the like. Biological test samples may be obtained from all of the various families of domestic animals, as well as feral or wild animals, including, but not limited to, such animals as ungulates, bear, fish rodents, etc. Environmental test samples include environmental material such as surface matter, soil, water and industrial samples, as well as test samples obtained from food and dairy processing instruments, apparatus, equipment utensils, disposable and non-disposable items. These examples are not to be construed as limiting the sample types applicable to the methods. In the other context, sample refers to a sample of selectable probes isolated from a reaction mixture. That is, it refers to a subset or subpopulation of selectable probes isolated from a reaction mixture that is representative of the full set or population of selectable probes formed in the reaction mixture.

Single-stranded or double-stranded DNA populations may refer to any mixture of two or more distinct species of single-stranded DNA or double-stranded DNA, which may include DNA representing genomic DNA, genes, gene fragments, oligonucleotides, PCR products, expressed sequence tags (ESTs), or nucleotide sequences corresponding to known or suspected single nucleotide polymorphisms (SNPs), having nucleotide sequences that may overlap in part or not at all when compared to one another. The species may be distinct based on any chemical or biological differences, including differences in base composition, order, length, or conformation. The single-stranded DNA population may be isolated or produced according to methods known in the art, and may include single-stranded cDNA produced from a mRNA template, single-stranded DNA isolated from double-stranded DNA, or single-stranded DNA synthesized as an oligonucleotide. The double-stranded DNA population may also be isolated according to methods known in the art, such as PCR, reverse transcription, and the like. Generally, one of ordinary skill in the art recognize when DNA called for in a process is required to be in single stranded form or double stranded form, such as, when hybridizing a primer to a target polynucleotide or processing a polynucleotide with a restriction endonuclease, respectively. Where the single-stranded DNA population is cDNA produced from a mRNA population, it may be produced according to methods known in the art. See, e.g., Maniatis et al. In a preferred embodiment, a sample population of single-stranded poly(A)+ RNA may be used to produce corresponding cDNA in the presence of reverse transcriptase, oligo-dT primer(s) and dNTPs. Reverse transcriptase may be any enzyme that is capable of synthesizing a corresponding cDNA from an RNA template in the presence of the appropriate primers and nucleotide triphosphates. In a preferred embodiment, the reverse transcriptase may be from avian mycloblastosis virus (AMV), Moloney murine leukemia virus (MMuLV) or Rous Sarcoma Virus (RSV), for example, and may be thermal stable enzyme (e.g., hTth DNA polymerase).

"Solid support", "support", and "solid phase support" are used interchangeably and refer to a material or group of materials having a rigid or semi-rigid surface or surfaces. In many embodiments, at least one surface of the solid support will be substantially flat, although in some embodiments it may be desirable to physically separate synthesis regions for different compounds with; for example, wells, raised regions, pins, etched trenches, or the like. According to other embodiments, the solid support(s) will take the form of beads, resins gels, microspheres, or other geometric configurations. Microarrays usually comprise at least one planar solid phase support, such as a glass microscope slide.

"Specific" or "specificity" in reference to the binding of one molecule to another molecule, such as a labeled target sequence for a probe, means the recognition, contract, and formation of a stable complex between the two molecules, together with substantially less recognition, contact, or complex formation of that molecule with other molecules. In one aspect, "specific" in reference to the binding of a first molecule to a second molecule means that to the extent the first molecule recognizes and forms a complex with another molecules in a reaction or sample, it forms the largest number of the complexes with the second molecule. Preferably, this largest number is at least fifty percent. Generally, molecules involved in a specific binding event have areas on their surfaces or in cavities giving rise to specific recognition between the molecules binding to each other. Examples of specific binding include antibody-antigen interactions, enzyme-substrate interactions, formation of duplexes or triplexes among polynucleotides and/or oligonucleotides, receptor-ligand interactions, and the like. As used herein, "contact" in reference to specificity or specific binding means two molecules are close enough that weak non-covalent chemical interactions, such as Van der Waal forces, hydrogen bonding, base-stacking interactions, ionic and hydrophobic interactions, and the like, dominate the interaction of the molecules.

"Tm" is used in reference to "melting temperature." Melting temperature is the temperature at which a population of double-stranded nucleic acid molecules becomes half dissociated into single strands. Several equations for calculating the Tm of nucleic acids are well known in the art. As indicated by standard references, a simple estimate of the tm value may be calculated by the equation. $T_m=81.5+0.41$ (% G+C), when a nucleic acid is in aqueous solution at 1 M NaCl (see e.g., Anderson and Young, Quantitative Filter Hybridization, in Nucleic Acid Hybridization (1985). Other references (e.g. Allawi H. T. & SantaLucia, J., Jr., Biochemistry 36, 10581-94 (1997)) include alternative methods of computation which take structural and environmental, as well as sequence characteristics into account for the calculation of Tm.

Uracil DNA glycosylase or UDG specifically recognizes uracil and removes it by hydrolyzing the N—C1' glycosylic bond linking the uracil base to the deoxyribose sugar. The loss of the uracil creates an abasic site (also known as an AP site or apurinic/apyrimidinic site) in the DNA. An abasic site is a major form of DNA damage resulting from the hydrolysis of the N-glycosylic bond between a 2-deoxyribose residue and a nitrogenous base. This site can be generated spontaneously or as described above, via UDG catalyzed hydrolysis See Marenstein et al. (2004) DNA Repair 3:527-533. Treatment of the sample DNA molecule or sample nucleic acid with alkaline solutions or enzymes, such as but not limited to apurinic/apyrimidinic endonucleases, will cause controlled breaks in the DNA at the abasic site. See U.S. Pat. No. 6,713,294. The abasic site can be cleaved by physical or enzymatic means. While high temperature or high pH induced hydrolysis can generate cleavage at abasic sites, the resulting 3' termini of the cleavage may not be a substrate for labeling by TdT. An apurinic/apyrimidinic endonuclease can cleave the DNA molecule or nucleic acid at the site of the dU residue yielding fragments possessing a 3'-OH termini, thus allowing for subsequent terminal labeling. One such apurinic/apyrimidinic endonuclease is *E. coli* Endo IV which catalyzes the formation of single-strand breaks at apurinic and apyrimidinic sites within a double-stranded DNA to yield 3'-OH termini suitable for terminal labeling. *E. coli* Endo IV may also be used to remove 3' blocking groups (e.g. 3'-phosphoglycolate and 3'-phosphate) from damaged ends of double-stranded DNA. See Levin, J. D., J. Biol. Chem., 263:8066-8071 (1988) and Ljungquist, et al., J. Biol. Chem., 252:2808-2814 (1977).

The AP endonuclease may be, for example, human APE 1 or a variant thereof. Human APE 1, unlike *E. coli* Endo IV, is capable of cleaving either single-stranded or double-stranded substrate at AP sites. APE 1 is also known as Hap1 Apex, and Ref1 and can be utilized in conjugation with UDG to perform cleavage at dU incorporation sites in single-strand and double strand DNA. APE 1 is an enzyme of the base excision repair pathway which catalyzes endonucleolytic cleavage immediately 5' to abasic sites. See Marenstein supra. Additional information about APE 1 may be found in Robson, C. N. and Hickson, D. I. (1991) Nucl. Acids Res., 19, 5519-5523, Vidal, A. E. (2001) EMBO J., 20, 6530-6539, Demple, B. et al. (1991) Proc. Natl. Acad. Sci. USA, 88, 11450-11454, Barzilay, G. et al. (1995) Nucl. Acids Res., 23, 1544-1550, Barzilay, G. et al. (1995) Nature Struc. Biol., 2, 451-468, Wilson, D. M. III et al. (1995) J. Biol. Chem., 270, 16002-16007, Gorman, M. A. et al (1997) EMBO J., 16, 6548-6558, Xanthoudakis, S. et al. (1992) EMBO J., 11, 3323-3335, Walker, L. J. et al. (1993) Mol. Cell. Biol., 13, 5370-5376, and Flaherty, D. M. (2001) Am. J. Respir. Cell. Mol. Biol., 25, 664-667, each of which is incorporated herein by reference in its entirety for all purposes.

The disclosure provides methods for appending one or more oligonucleotides directly to a single stranded nucleic acid template, typically (but not invariably) at one or more defined sites internal to the template. The oligonucleotides may be designed to provide one or more sites for priming the subsequent amplification of adjacent template regions. The methods may be readily multiplexed, permitting oligonucleotides to be appended, in a single reaction, to a plurality of templates. In multiplex embodiments in which the appended oligonucleotides provide one or more common priming sites, the plurality of templates may then be concurrently amplified using primers common to all templates. Such multiplexed amplification reactions provide high specificity and uniform amplification of all templates, solving problems that have plagued multiplex amplification reactions since the invention of PCR.

In a first aspect, methods are provided for appending at least a first oligonucleotide (probe) directly to a nucleic acid template. The method may conveniently be understood by reference to the illustrative reaction of FIG. 1, in which first oligonucleotide (probe) 20 is appended to a distinct site internal to template 10.

In the first step of the method, illustrated in FIG. 1A, first probe 20 is annealed to single stranded specific sequence of interest (template 10). Probe 20 includes at least one template complementarity region 21, a decoding (barcode) region 22, and at least one common sequence (primer) region 23 that may be used for PCR amplification. In the annealing step, template region 11, which contains the sequence of interest, hybridizes to the 3' end of the probe at complementarity region 21. Region 21 is selected to be complementary to the target over a length that may be, for example, about 10 to 25 bases. In a preferred embodiment, 21 is perfectly complementary to a region of target 11 so that each base of 21 forms a base pair with a base in the target region so that the entire length of 21 is participating in a base pairing arrangement with target 11. The length and sequence are chosen to confer sufficient stability and specificity of hybridization to the template. Probe 20 is preferably designed to include at least one sequence to which an oligonucleotide primer can later anneal (a "priming site" 23). It is to be understood that when referring to a priming site this includes the complement of that sequence. For example, priming site 23 is illustrated in the 5' to 3' orientation. A primer for amplification of the extension product of probe 20 would have the same orientation as priming site 23, i.e. 5' to 3' and would have a sequence that is identical to priming site 23 or a portion thereof, preferably at least 15 contiguous bases of priming site 23. The primer would hybridize to the complement of priming site 23 as illustrated in an extension reaction.

In step 101, the 3' end of the first probe 20 is extended by DNA synthesis using template 10. The information from template 10 that is 5' of where probe 20 hybridizes is copied into newly synthesized molecule 100. The newly synthesized region is represented by a dashed line and is the complement of template 10 over the length of the newly synthesized segment 100. Base pairing is represented schematically by vertical dotted lines, but the number is not intended to indicate any specific number of base pairs. The products resulting from step 101 are shown in the lower panel of FIG. 1A, illustrating that the first probe 20 is covalently attached to the 5' end of the newly synthesized linear molecule 100. In preferred aspects a polymerase extends first probe 20 from the 3' end. The product of the reaction is a duplex molecule including template 10 and newly synthesized linear molecule 100.

In step 102, the duplex molecule is dissociated, for example by heating, and second oligonucleotide probe 30 is annealed to a region within the newly synthesized linear molecule portion. The product is illustrated in FIG. 1B. Probe 30 includes at least one region 21b that is complementary to a sequence within the newly synthesized portion of the extended probe and also includes at least one sequence region 32 used as ligation template in the annealing step 104. The newly synthesized liner molecule 100 contains the sequence of interest and is shown hybridized to the 3' portion 21b of the second probe. Appropriate sequence and length of the complementary region 21b are preferably chosen to provide high specificity of hybridization to the newly synthesized linear molecule.

The sequence and length of the region 32 depend of the specific conditions of the subsequent ligation step, but can be between 5 and 40 nucleotides in length and may contain a sequence that is completely or partially complementary to a ligatable oligonucleotide.

In step 103, the non annealed single stranded 3' end 100b of the linear molecule is degraded by single stranded 3' to 5' exonuclease activity. Exonuclease degradation results in a 3' recessed end at the end of the linear molecule and a 5' single stranded overhanging portion of probe 30. Exonuclease degradation is used to degrades the bases from the 3' end of the extension product that are not in the duplex with second probe 30. The product of degradation is a complete duplex structure at the 3' end of the linear molecule with complementary region 31 of second probe 30. Region 32 at the 5' end of the second probe 30 remains single stranded and should not be degraded.

In step 104, illustrated in FIG. 1C, ligatable oligonucleotide 40 is ligated to the recessed 3' end of the linear extension molecule. Ligatable oligonucleotide 40 includes at least one region 41 partially or completely complementary to region 32 of second probe 30 and at least one common sequence region 42 that can be used as a priming site for PCR amplification. The sequence and length of the region 41 depend on the specific conditions which used for ligation of the ligatable oligonucleotide 40 to the recessed 3' end of the newly synthesized linear molecule. Under different conditions this sequence can between 1 and 40 nucleotides in length, but preferably 5 to 40, and may contain the sequence completely or partially complementary to region 32 of second probe 30.

Step 105 may include denaturation to remove probe 20. This is optional and may be accomplished by strand displacement during the extension of primer P2 or by heat denaturation as non limiting examples. The final product of the reaction consists of the complementary strand of the specific sequence of interest flanked at both sites by common sequences and can be used as template for PCR amplification. As shown in the bottom panel of FIG. 1C, P1 and P2 primers composed of sequences which can be used for priming at the priming sites located at common sequences can be used for amplification.

Template 10 may be derived directly from single-stranded cDNA, such as that obtained by first strand synthesis from mRNA transcripts, or from cDNA rendered single-stranded by denaturation of double-stranded cDNA obtained either directly after second strand cDNA synthesis or from prior-cloned double stranded cDNA. Template 10 may be derived from genomic DNA, which may be, for example, prepared directly from cells or from genomic DNA that has been cloned or amplified. Typically, genomic DNA is first denatured, e.g. by heat or treatment with base, to provide single stranded template 10.

Template 10 may be derived from a single individual or pooled from a plurality of individuals. Templates from a single individual are useful, for example, in genotyping or haplotyping. Pooled templates are useful in SNP discovery efforts, and may usefully be pooled from at least 10 individuals, 100 individuals, even 1000 individuals or more.

The target nucleic acids uses as templates may be derived from nucleic acids drawn from a prokaryote, eukaryote, or virus. Prokaryotes include both archaebacteria and eubacteria, including both gram negative and gram positive eubacteria, and the nucleic acids targets in some embodiments may be from pathogenic prokaryotes and may be in samples derived from patients that have symptoms of a disease caused by one or more pathogenic prokaryotes. Among eukaryotes, template 10 may usefully be drawn from a wide variety of protozoa, fungi, insects, plants, and animals. Animals may be selected from the group consisting of mammals, such as primates, including humans, monkeys, and apes, small laboratory animals, including rodents, such as mouse or rat, guinea pigs, lagomorphs, such as rabbits, livestock, such as cows, horses, chickens, geese, turkeys, goats, and sheep, and domestic pets, such as dogs and cats. Template 10 may also be derived from viral nucleic acids, including viruses selected from the group consisting of double-stranded DNA viruses, such as herpesviruses, retroviruses, including mammalian type B retroviruses, avian type C retroviruses such as avian leukosis virus; type D retroviruses such as Mason-Pfizer monkey virus; BLV-HTLV retroviruses such as bovine leukemia virus; lentiviruses, such as bovine lentiviruses, feline immunodeficiency virus, and primate lentiviruses such as human immunodeficiency virus 1 (HIV 1), and other types of pathogenic viruses.

Template 10 is typically at least about 40 nucleotides ("nt") in length, often at least 50, 75, 100, 125 or 150 nt in length, at times at least about 200 nt, 300 nt, 400 nt, or 500 nt or more in length, and when derived from genomic nucleic acid can be at least 1000 nt (1 kb), 2 kb, 3 kb, 4 kb, 5 kb, 10 kb, 20 kb, 30 kb, 40 kb or 50 kb in length. In preferred aspects more than 10, preferably more than 100, more preferably more than 1000 and sometimes more than 10,000 different targets may be amplified simultaneously using a single primer pair for PCR amplification. This allows for large numbers of specific targets to be amplified from a sample for enrichment of targets of interest. The amplified products may then be analyzed, for example by sequencing.

First probe 20 includes at least first template complementarity region 21. Template complementarity region 21 of first probe 20 is designed to have sufficient length and sufficient sequence complementarity to a region of template 10 as to permit annealing of probe 20 to template 10 under hybridization conditions of desired stringency. The region of template 10 to which probe template complementarity region 21 hybridizes is defined as template region 11. Template complementarity region 21 of first probe 20 is typically at least 10 nt in length, more typically at least 15, 20, 25, or 30 nt in length or even more in length. Region of interest 11 of template 10 is typically no more than about 1000 nt in length, typically no more than about 500 nt in length, often no more than 400 nt, 300 nt, 200 nt, even no more than 100 nt in length.

Decoding or tag region 22 is preferably not complementary to the template and designed for detection of the product without directly detecting the sequence of interest. Often the decoding sequence is composed of artificially designed sequences which are optimized for specific detection by hybridization. Each first probe 20 preferably contains a different individual decoding sequence. At the end of the reaction each specific product has the individual decoding sequence attached to it. Decoding region 22 of first probe 20 is typically at least 10 nt in length, more typically at least 15, 20, 25, or 30 nt in length or greater.

Probe 20 is typically further designed to include a sequence to be used as a "priming site", to which an oligonucleotide primer can anneal in later steps. The priming site may be at terminal region 23 or at decoding region 22 if decoding sequence is use for product specific amplification, or may be only a portion thereof. The length and sequence of the priming site sequence are chosen based upon considerations well known in the art, including the calculated Tm (melting temperature) of the duplex expected between the priming site and the primer, the absence of the priming site sequence or its complement in templates desired to be amplified, and the like.

Complementarity region 31 of second probe 30 is designed to have sufficient length and sufficient sequence complementarity to a newly synthesized linear molecule with in region 11 as to permit annealing of probe 30 to newly synthesized linear molecule under hybridization conditions of desired stringency. The region of template 10 to which probe template complementary region 31 hybridizes is defined as template region 11.

Complementarity region 31 of second probe 30 is typically at least 10 nt in length, more typically at least 15, 20, 25, or 30 nt in length or even more in length. Second probe 30 includes terminal region 32 which is used as template for ligation of ligatable oligonucleotide 40.

Region 32 of probe 30 is further designed to have sufficient sequence complementarity to region 41 of ligatable oligonucleotide 40 as to permit ligation of recessed 3' end of the newly synthesized linear molecule to 5' end of ligatable oligonucleotide 40. The region 32 of second probe 30 is typically at least 1 nt in length, more typically at least 4, 10, 20, or 30 nt in length or even more in length. Ligatable oligonucleotide 40 includes second probe complementarity region 41.

Region 41 of probe 40 is further designed to have sufficient sequence complementarity to region 32 of probe 30 as to permit ligation of recessed 3' end of the newly synthesized linear molecule to 5' end of ligatable oligonucleotide 40. Region 41 of ligatable oligonucleotide 40 is typically at least t least 1 nt in length, more typically at least 4, 10, 20, or 30 nt in length or even more in length. Ligatable oligonucleotide 40 is typically further designed to include a sequence, a "priming site", to which an oligonucleotide primer can anneal in later steps.

The priming site may be at terminal region 42 or include complete region 41 or part or may be only a portion thereof. The length and sequence of the priming site sequences uses in the methods throughout the disclosure are chosen based upon considerations well known in the art, including the calculated Tm of the duplex expected between priming site and primer, the absence of the priming site sequence or its reverse complement in templates desired to be amplified, and the like. Probe 20 and 30, and ligatable oligonucleotide may be synthesized chemically, using solid phase procedures well known in the art, or by ligation of smaller, chemically-synthesized fragments. Ligatable 3' recessed ends may be created using exonucleolytic digestion, with the choice of nuclease determined by the desired direction of digestion. For example, regions of newly synthesized linear molecule that are not complementarity to probe 30 may be removed by reaction with Exo I (3' to 5' exonuclease), Exo T (3' to 5'), Exo VII (both 3' to 5' and 5' to 3' exonuclease activity), and the 3' to 5' proof reading activity of DNA polymerase.

Figure 2D:
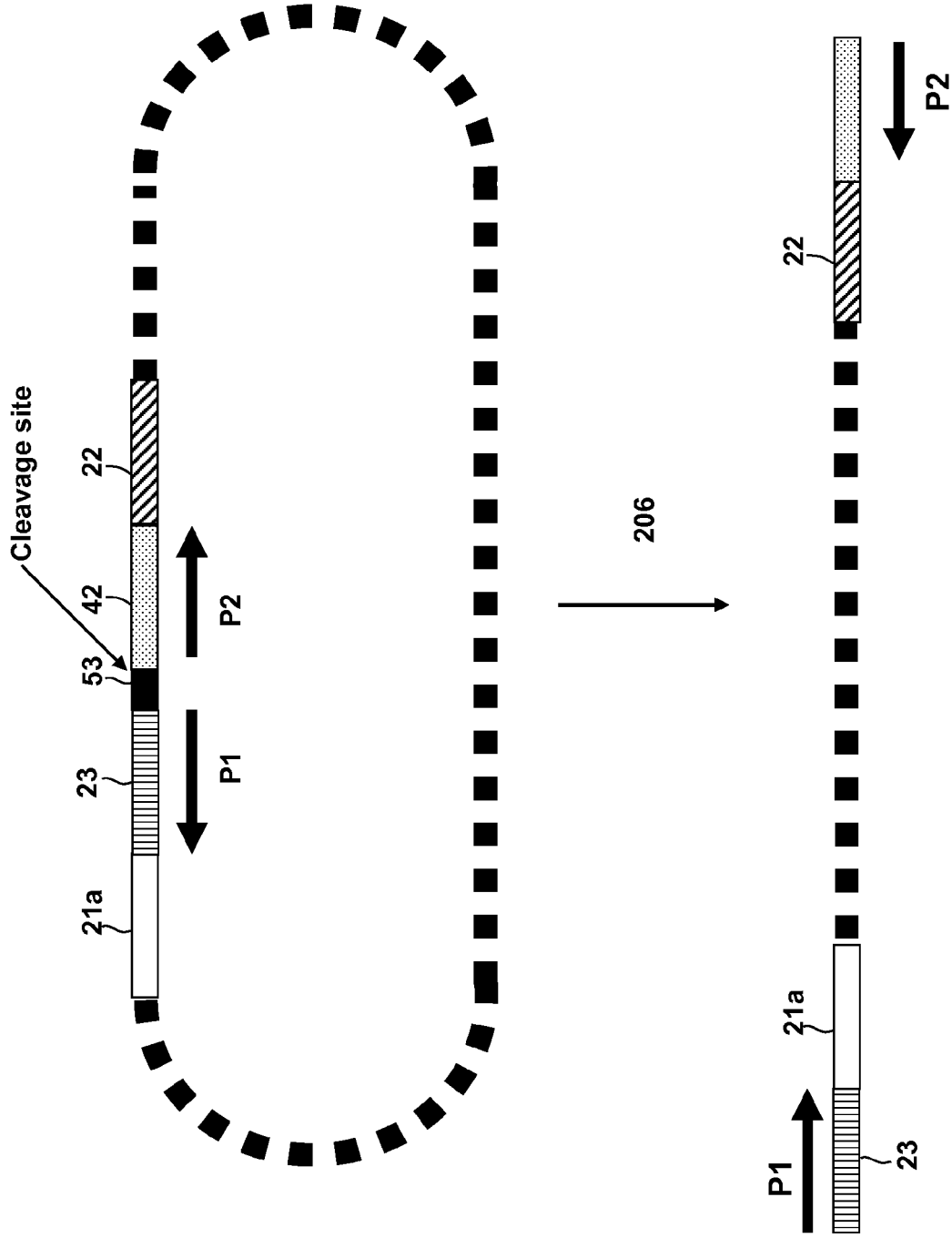
FIG. 2D illustrates opening the circular molecule at the cleavage site and the resulting product suitable for PCR amplification using primers P1 and P2.

In another series of embodiments, illustrated in FIG. 2, first and second probes are used for attachment of the common sequences through intra-molecular circularization between the recessed 3' end of the newly synthesized linear molecule and the 5' end of the first probe. A third probe for ligation is not required. In step 201, illustrated in FIG. 2A, first probe 50 is annealed to the sequence of interest (template 10). Probe 50 includes from the 3' end: template complementarity region 21a, first common sequence (primer 1) region 23 used for PCR amplification, cleavage site 53, second common sequence (primer 2) region 42 used for PCR amplification, and decoding (barcode) region 22. In probe 50 primer 1 and primer 2 are designed so that the primers P1 and P2 extend in opposite directions (see FIG. 2D). An alternative order of regions in probe 50 is from the 3' end: template complementarity region 21a, decoding (barcode) region 22, first common sequence (primer 1) region 23 used for PCR amplification, cleavage site 53, second common sequence (primer 2) region 42 used for PCR amplification.

In the annealing step, template complementarity region 21a, is hybridized to the 3' end of the first probe 50 at complementarity region 21a. Then, the 3' end of the first probe 50 is extended by DNA synthesis in step 201 using template 10. The information from template 10 in copied into newly synthesized molecule 100 represented by the dashed line. The first probe 50 is covalently attached to the 5' end of the newly synthesized linear molecule 100. The product of the reaction is a duplex molecule formed by template and newly synthesized linear molecule 100.

In step 202, the duplex molecule is dissociated (template 10 has dissociated from the extended probe 50) and second oligonucleotide (probe) 60 is annealed to the newly synthesized linear molecule. Probe 60 includes at least one region 21b complementary to the newly synthesized linear molecule and at least one sequence region 62 used as ligation template in steps 204 and 205. The 3' end of newly synthesized linear molecule 100, which contains the sequence of interest, is hybridized to the 3' end of the second probe at complementarity region 21b.

The sequence and length of the region 62 depend on the specific conditions required to facilitate the intra-molecular ligation of the 5' end of first probe 60 to the 3' end of the linear molecule 100 via circularization in a subsequent step. Under different conditions this sequence can be between 1 and 40 nucleotides in length, preferably 5 to 40 and more preferably 5 to 20 and may be completely or partially complementary to region 22 of probe 50.

In step 203, the non annealed single stranded 3' end 100b of the linear molecule 100 is degraded by single stranded 3' to 5' exonuclease activity. As the product of exonuclease degradation the 3' recessed end is generated between 3' end of linear molecule and second probe 60. Exonuclease degradation is used to degrade the bases which are not in the duplex with second probe 60. The product of degradation is a complete duplex structure at the 3' end of the linear molecule with complementary region 21b of second probe 60. Region 62 at the 5' end of the second probe 60 remains single stranded and is preferably not degraded so that it can serve a splinting function in steps 204 and 205.

In step 205, illustrated in FIG. 2C, the 5' end of the capture probe 50 is ligated to the recessed 3' end of linear molecule 100 via intra-molecular circularization which results in the closed circular structure illustrated in FIG. 2C lower panel. The region 62 and region 22 form a duplex. In some aspects a portion of region 22 is designed to be complementary to region 62. There may be, for example, 5 to 10 or 10 to 20 or more bases of complementarity. The circular molecule is largely single stranded and may be entirely single stranded after removal of probe 60, and may be opened in step 206 at cleavage site 53 as illustrated in FIG. 2D.

The final products of the reaction consist of the complementary strand of specific sequence of interest flanked at both sites by common sequences and can be used as template for PCR amplification. P1 and P2 primers can be used for priming at the priming sites located at common sequences as schematized in FIG. 2D lower panel.

Probe 50 includes at least one template complementarity region 21a. Template complementarity region 21a of first probe 50 is designed to have sufficient length and sufficient sequence complementarity to a region of template 10 as to permit annealing of probe 50 to template 10 under hybridization conditions of desired stringency. The region of template 10 to which probe template complementary region 21a hybridizes is defined as template region 11. Template complementarity region 21a of first probe 20 is typically at least 10 nt in length, more typically at least 15, 20, 25, or 30 nt in length or even more in length. First probe 50 includes preferably at least decoding (barcode) region 22.

Decoding region 22 typically is non complementary to template and designed for detection of the product without directly detecting sequence of interest. Often decoding sequence is composed of artificially designed sequences which are optimized for specific detection by hybridization. Each first probe 50 contains individual decoding sequence. At the end of the reaction each specific product has the individual decoding sequence attached to it. Decoding region 22 of first probe 50 is typically at least 10 nt in length, more typically at least 15, 20, 25, or 30 nt in length or even more in length. Probe 50 is typically further designed to include the sequences for two "priming sites", to which an oligonucleotide primers can anneal in later steps. The priming site may be at terminal region 23 and 42 or at decoding region 22 if decoding sequence is use for product specific amplification, or may be only a portion thereof.

Second probe 60 includes newly synthesized linear molecule complementary region 21b. Complementarity region 21b of second probe 60 is designed to have sufficient length and sufficient sequence complementarity to a newly synthesized linear molecule with 10 as to permit annealing of probe 60 to newly synthesized linear molecule under hybridization conditions of desired stringency. Complementarity region 21b of second probe 60 is typically at least 10 nt in length, more typically at least 15, 20, 25, or nt in length or even more in length.

Second probe 60 includes terminal region 62 which is used as template for intra-molecular ligation to 5' end of first probe 50. Region 62 of probe 60 is further designed to have sufficient sequence complementarity to region 22 of probe 50 as to permit ligation of recessed 3' end of the newly synthesized linear molecule to 5' end of probe 50 via intra-molecular circularization. The region 62 of second probe 60 is typically at least 1 nt in length, more typically at least 4, 10, 20, or 30 nt in length or even more in length. Probe 50 and 60 may be synthesized chemically, using solid phase procedures well known in the art, or by ligation of smaller, chemically-synthesized fragments.

In another aspect, illustrated in FIG. 3, probe 70 is hybridized to template 10 at two regions through base pairing to regions 21c and 21a of the probe with formation of a looped structure in the middle of the probe. Once the two duplexes have formed, the looped structure in between is protected from degradation by single stranded exonuclease activities and can be used for increasing the specificity of the first hybridization.

Figure 3A:
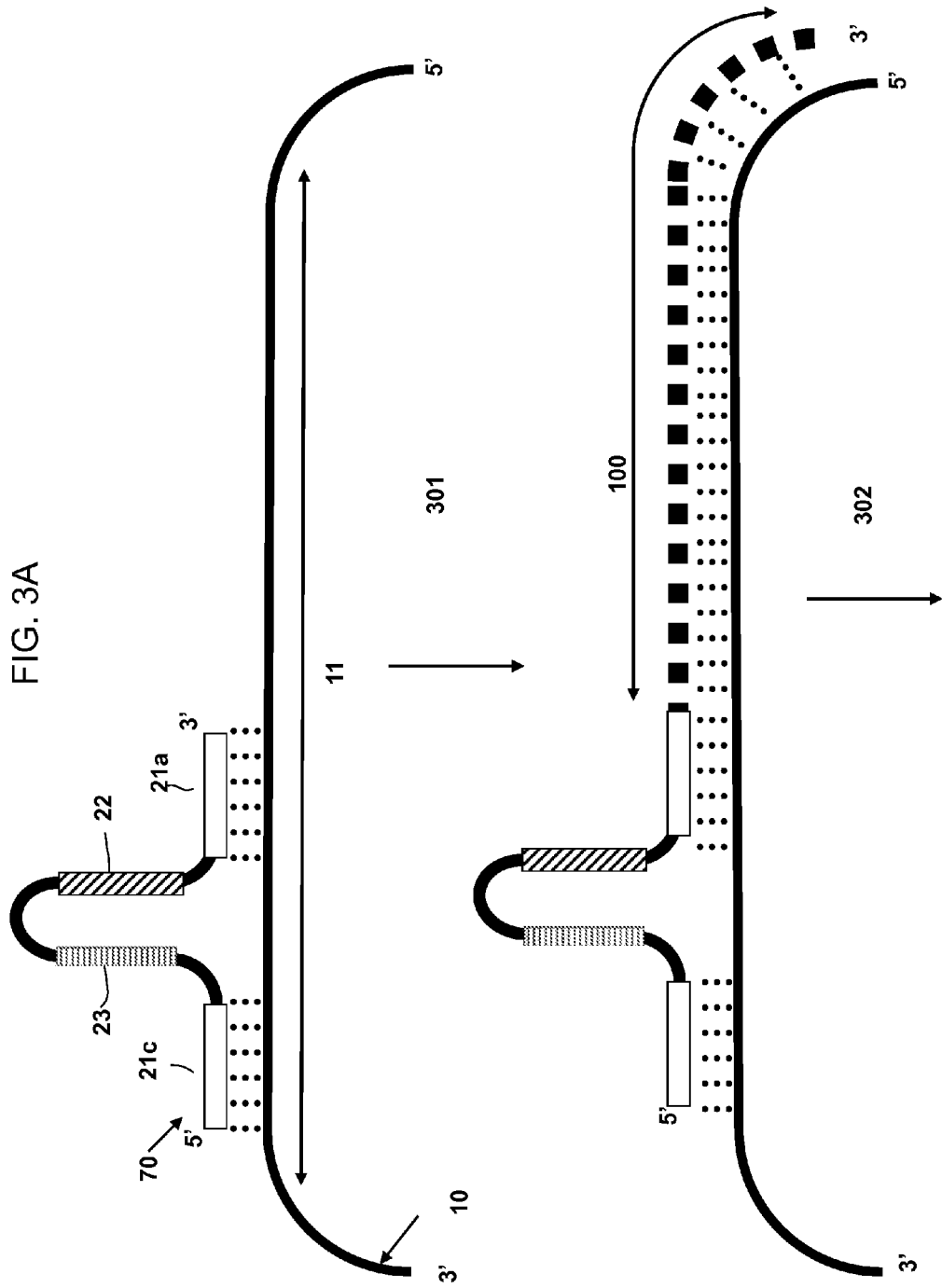
FIG. 3A is a schematic illustrating hybridization of a first oligonucleotide containing a common sequence flanked by two target complementary sequences to the target and extending that oligonucleotide using the target as template.

Prior to step 301, illustrated in FIG. 3A, first probes 70 are annealed to single stranded target having a specific sequence of interest. As in the embodiments described above, a different probe 70 is used for each sequence of interest so there is a collection of probes 70 that have regions that are common to all probes and regions that are variable and target specific. Region 23 is common to all probes in the collection of probes 70.

Probe 70 includes two target complementarity (target specific) regions 21c and 21a, optionally a decoding (barcode) region 22 that may be specific for a single target or common over two or more targets, and at least one common sequence region 23 that is preferably common to all or to many probes 70 and can be used, for example, for PCR amplification. In the annealing step, template region 11, which contains the sequence of interest, hybridizes to the 3' end of probe 70 at target complementarity regions 21c and 21a.

At lower probe 70 concentrations and lower stringency hybridization conditions the annealing of one of the complementarity regions will bring the second complementarity region within close proximity to the template, accelerating annealing of the second region. Once the two duplexes between the probe and template have formed the dissociation rate for the probe will be significantly lower. If dissociation of one region occurs the likelihood that it will re-associate is higher because it will be held in close proximity to the complementary region in the target via the association of the second duplex. Additionally the positioning of the common sequence between the two duplexes allows for protection of the loop area from degradation by single stranded exonuclease degradation.

In step 301, the 3' end of the first probe 70 is extended by DNA synthesis using target 10 as template. The information from the target is copied into the newly synthesized molecule 100. The products resulting from step 301 include a duplex molecule formed by target 10, the probe 70 and the newly added extended portion 100.

Figure 3C:
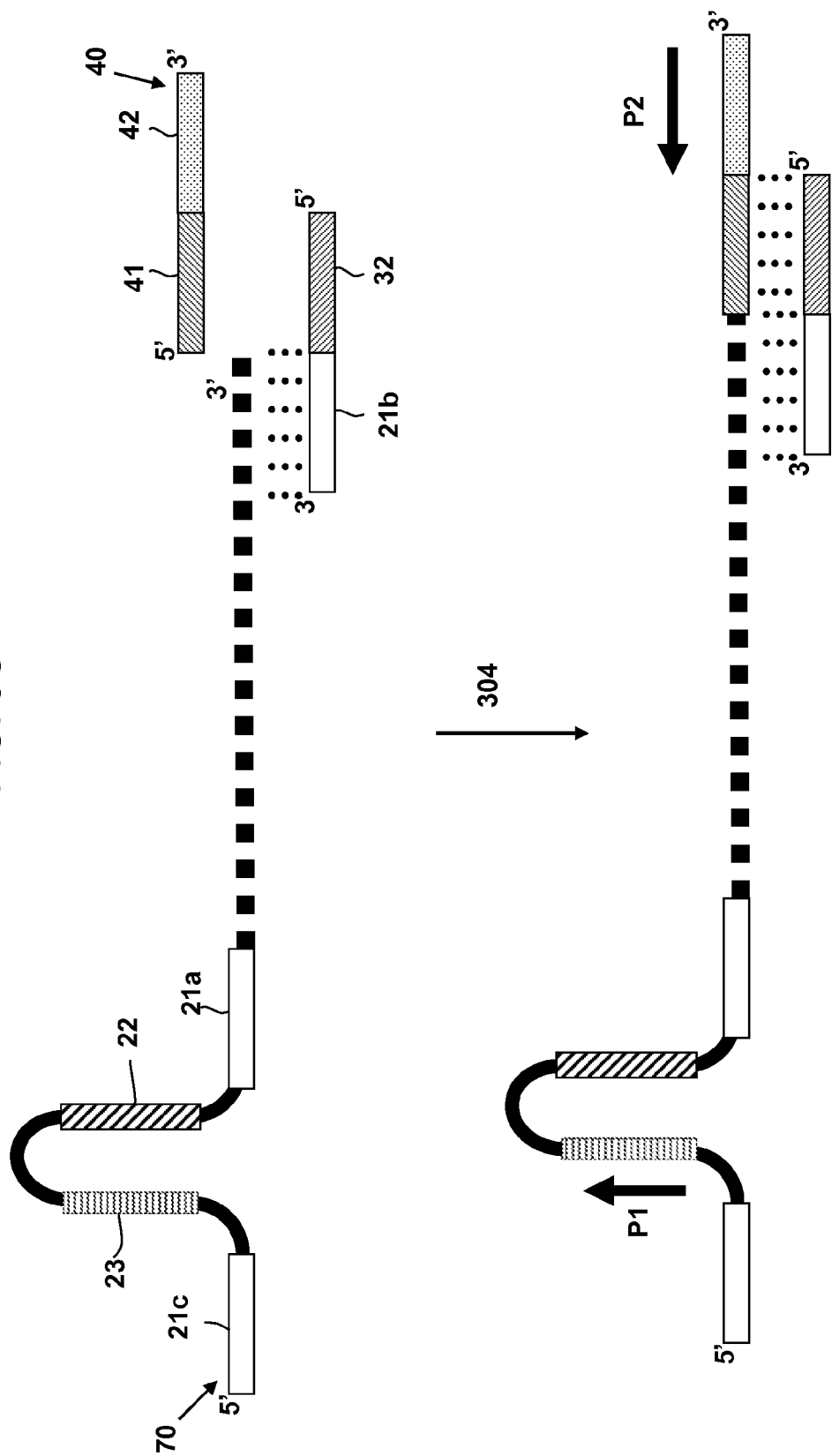
FIG. 3C illustrates hybridization of the ligatable polynucleotide at the recessed 3' end of linear molecule and ligation of 5' end of the ligatable oligonucleotide to the recessed 3' end of linear molecule.
Figure 3D:
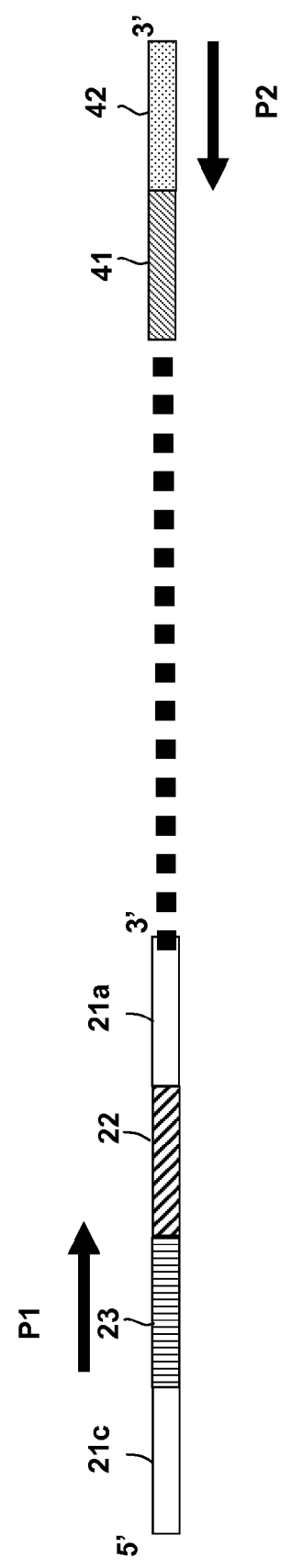
FIG. 3D is a schematic representation of the resulting product showing positions for hybridization of primers.

FIGS. 3B-3D illustrate a method for attaching a second common priming sequence to the 3' end of the extended probe 70. In step 302 the duplex molecule is dissociated, for example by heat denaturation and a second oligonucleotide 30 is annealed to the newly synthesized linear molecule through interaction with target complementary region 21b. If there is sequence in the extension product that is 3' of the region where 30 anneals, 100b as shown in the figure, that portion can be degraded in step 303 by a single stranded 3' to 5' exonuclease activity to obtain the duplex shown in the lower panel of FIG. 3B resulting in a 5' single stranded overhanging portion of probe 30 and a recessed 3' end of the extension product. In FIG. 3C a ligatable oligonucleotide 40, having region 41 that is complementary to region 32 of probe 30 is hybridized to probe 30 and ligated in step 304 to the end of the extension product, resulting in the duplex as schematized in the lower panel of FIG. 3C. Regions 42 and 23 are common priming sites that can be used for PCR amplification using primers P1 and P2 as schematized in FIG. 3D.

Target complementarity regions 21c and 21a of first probe 70 preferably have sufficient length and sequence complementarity to the target 10 to permit annealing of probe 70 to template 10 under hybridization conditions of desired stringency. The Tm of the regions 21c and 21a may be similar so they bind to their complementary segment of the target with similar stability, but in another aspect, the Tm of one target complementary region can be higher than the Tm of the other target complementary region, even substantially higher. Because regions 21c and 21a are part of the same probe, if one of the regions binds stably the second has a higher probability of annealing to its complement in the target due to close proximity to the target. Regions 21c and 21a are typically at least 10 nucleotides in length, more typically at least 15, 20, 25, or 30 nucleotides in length or even more in length.

The gap between the regions on target 10 that are complementary to regions 21c and 21a is typically at least 1 base in length, more typically at least 5, 10, 20, 30, 50, or 100 bases in length or even longer. Decoding region 322 is preferably not complementary to the target and is preferably designed for detection of the product without directly detecting the sequence of interest. Often decoding sequence is composed of artificially designed sequences which are optimized for specific detection by hybridization and may be referred to as a tag sequence. In one aspect, each different probe 70 contains a different decoding sequence that is characteristic of that probe. At the end of the reaction each specific product has the individual decoding sequence attached to it. The decoding sequence can be detected as a surrogate for detection of the specific target sequence of interest. Decoding region 22 of first probe 70 is typically at least 10 nt in length, more typically at least 15, 20, 25, or 30 nt in length or even more in length.

Probe 70 is typically further designed to include a sequence, a "priming site", to which an oligonucleotide primer can anneal in later steps. The priming site may be at region 23 or at decoding region 22 so the decoding sequence may be used for product specific amplification.

In other embodiments the position orders for regions 21c, 23, and 22 in probe 70 can vary, but preferably region 21a is at the 3' end of the probe 70. Probe 70 may contain additional sequence between regions 21c and 21a in addition to regions 22 and 23. The length of the loop may be up to about 200 nt in length or even greater in some aspects.

In some aspects there may be sequence 5' of region 21c that is not complementary to the target. There may also, in some aspects, be sequence 3' of region 21a that is not complementary to the target or is partially complementary to the target. If there are non-paired bases at the 3' end of the probe they are preferably degraded by single stranded exonuclease activity or a flap endonuclease activity prior to the extension step.

In another embodiment, illustrated in FIG. 4, a common sequence is added to the 3' end of the newly synthesized extension product by extension of the new 3' end using a hybridized probe 30 as template. The newly added portion 100 of the extended probe is hybridized to probe 30. Probe 30 includes at least one region 21b that is complementary to a region in the 3' end of extension product 100 and at least one common sequence (primer) region 32 that can be used for PCR amplification. The 3' end of the extension product is further extended in step 401 using region 32 of probe 30 as template to add region 83 to the extension product. If probe 30 hybridizes to the extension product so that there is a 3' overhang in the extension product that can be degraded by nuclease treatment as discussed above. After optional separation of the product from probe 30 in step 402, the final products of the reaction consist of the complementary strand of specific target sequence of interest flanked by common sequences and can be used as template for PCR amplification reaction. P1 and P2 primers can be used for priming at the priming sites located at common sequences as schematized in the bottom panel of FIG. 4. The length of complementarity region 21b is typically at least 10 nt, more typically at least 15, 20, 25, or nt in length or greater.

Figure 5A:
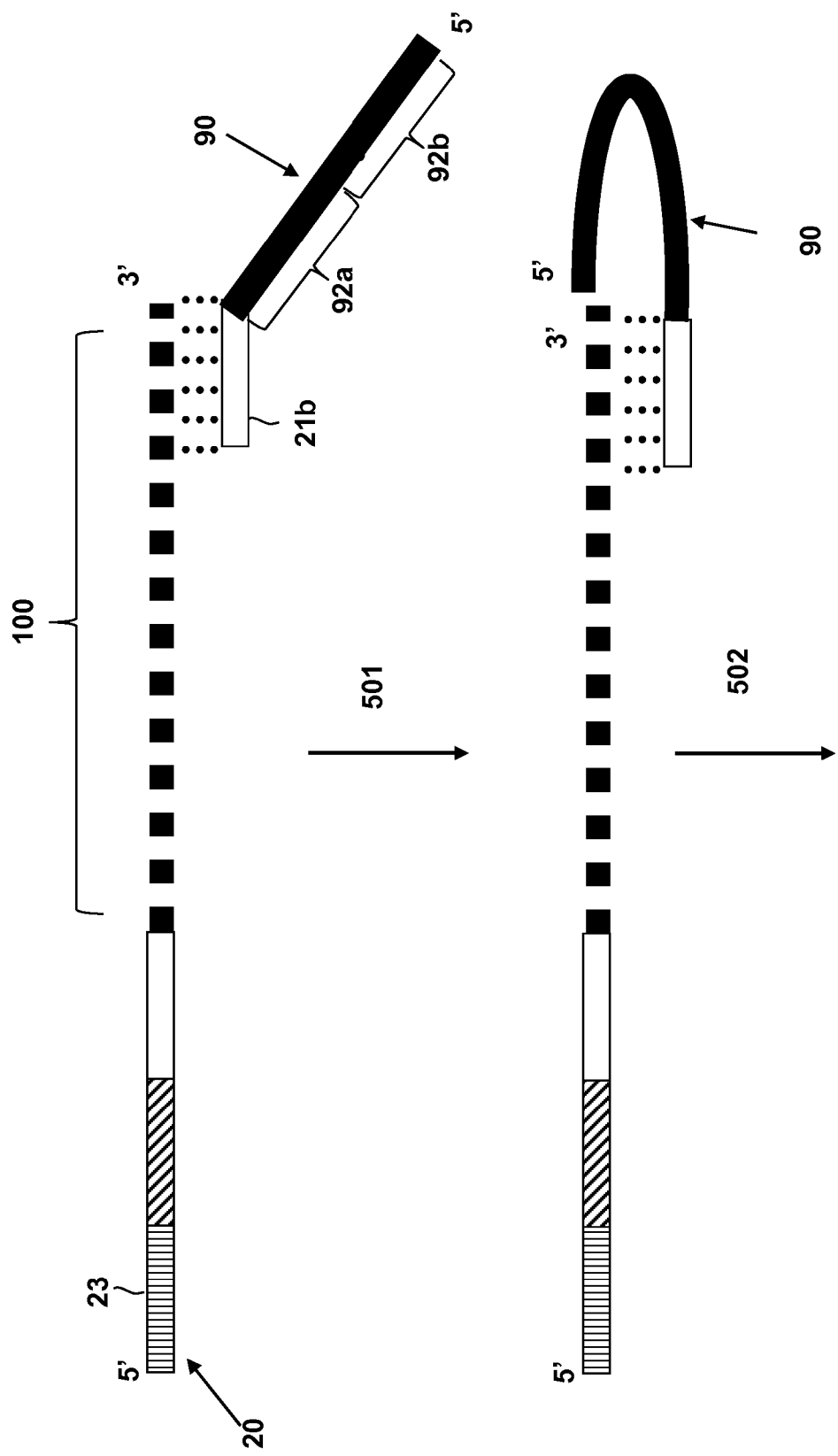
FIG. 5A is a schematic illustrating a method for attachment of common sequence at 3' end by intra-molecular ligation to the 5' end of the second probe.
Figure 5B:
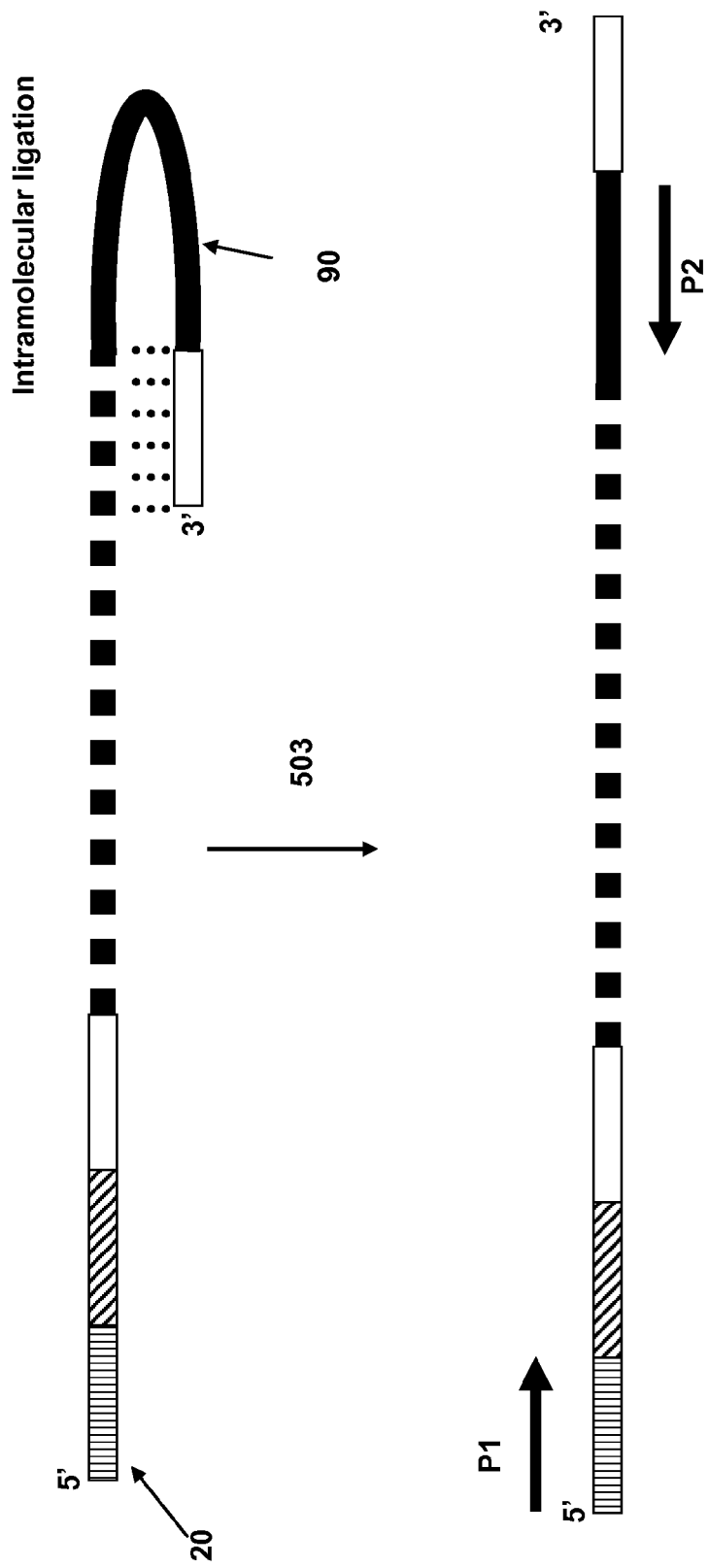
FIG. 5B shows the loop product formed after ligation of the 3' end of the linear molecule to the 5' end of the second primer and the resulting binding sites for primers P1 and P2.

In another embodiment, illustrated in FIG. 5, a common sequence is added to the 3' end of a target specific extension product 100 by intra-molecular looping and ligation to the 5' end of probe 90. Target specific extension product 100 is hybridized to second probe 90 through the basepairing of region 21b to its complement in 100. The non complementary single stranded 3' end of the newly synthesized linear molecule may be degraded by single stranded exonuclease activity to generation the recessed 3' end in 100 as discussed above. Probe 90 includes region 21b that is complementary to a region in the 3' end of 100 and at least one common sequence (primer) region 92 that can be used for PCR amplification. Region 92 can be divided into regions 92a and 92b which have some complementarity. In step 501 probe 90 forms an intra-molecular loop as a result of interaction between region 92a and 92b. In step 502 the 5' end of probe 90 is ligated to the 3' end of extension product 100. As shown in FIGS. 5B and 5C, the 5' end of probe 90 is then ligated to the 3' end of the linear molecule by loop formation.

Denaturation of the interaction between 92*a* and 92*b* in step 503 results in products having the complementary strand of specific sequence of interest flanked by common sequences and can be used as template for PCR amplification reaction. P1 and P2 primers can be used for priming at the priming sites located at common sequences as schematized in FIG. 5D. Complementarity region 92 of probe 90 is typically at least 10 nt in length, more typically at least 15, 20, 25, or 30 nt in length or even more in length. In order to ligate the end of probe 90 to the recessed 3' end of 100, the terminal 5' region of probe 90 may contain a region of self complementarity so that the 5' end of probe 90 forms one or more intra-molecular basepairs with the 3' end of region 92, thus juxtaposing the 5' end of probe 90 with the recessed 3' end of 100 for ligation. In preferred aspects 4 or more basepairs can be formed between the 3' end of probe 90 and region 92.

Figure 6:
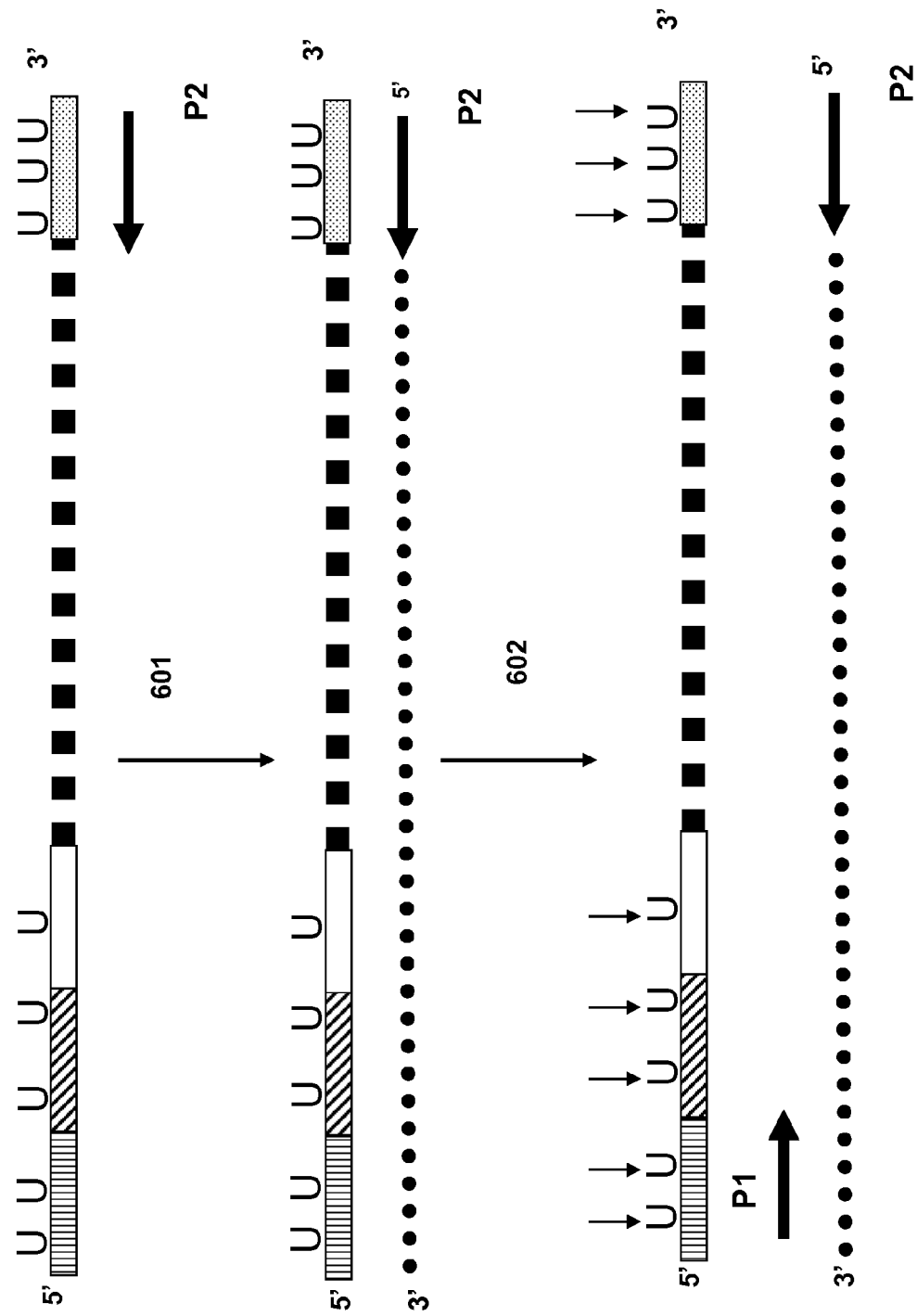
FIG. 6 is a schematic of a method where the extension product contains cleavable bases (U's) in the attached common sequences that can be used to degrade the extension product after the first extension using primer P2.

In another embodiment, illustrated in FIG. 6, the first and second probes, and ligatable oligonucleotides may include deoxyuridine residues as substitutes for some or all of the thymidine residues. Excess nonreacted probes and nonspecific product can be degraded in step 602 by cleavage at the uracil sites. In order to preserve the desired product of the reaction the common primer P2 is hybridized to the 3' end of the product and extended to generate the complement of the product. The new strand is synthesized in step 601 with natural nucleotides as illustrated in FIG. 6B. The deoxyuridine residues are presented as "U" in the figure. After synthesis the mixture is treated with uracil-DNA glycosylase ("UDG"), which catalyzes the release of free uracil from uracil-containing DNA, creating apurinic ("AP") sites. AP sites may then be cleaved enzymatically for example using an AP endonuclease, chemically for example by imidazole, or they may be allowed to decompose naturally. Natural decomposition of AP site can be accelerated by heat and appropriate pH. In another alternative, the probe can include purines such as 8-oxoguanine, 8-oxoadenine, fapy-guanine, methyl-fapy-guanine, fapy-adenine, aflatoxin B-fapy-guanine, 5-hydroxy-cytosine, and 5-hydroxy-uracil, that mimic damaged purines. Fpg glycosylase will release these residues from DNA and remove the resulting AP site, leaving a 1 nucleotide gap (see, for example, Tchou, J. et al. (1994) J. Biol. Chem., 269, 15318-15324). For further discussion of methods for cleaving uracil containing nucleic acids see, for example, US Patent Pub. No. 20070218478 (now abandoned).

In another embodiment, the deoxyuridine triphospate nucleotide is used instead of thymidine triphosphate nucleotide in synthesis of linear molecule 100 and in the extension of the recessed 3' end. After extension the deoxyuridine nucleotide is degraded, removed, or diluted from the product. In order to preserve the final product of the reaction the common primer P2 is hybridized to the common sequence at the 3' end of the linear molecule and a new strand is synthesized with natural nucleotides. Only the final product contains the sequence of interest which is flanked by the two common primer sites. Any non specific extensions of the first probes which do not have the second primer sequence at the end will be degraded UDG.

As used herein, the term amplification includes the production of RNA transcripts by polymerization driven from a phage promoter. More typically, however, the amplification product is DNA produced by polymerization primed using one or more oligonucleotides ("primers") that are capable of hybridizing to one or more priming sites within one or more of the oligonucleotides appended to the template. For example, a first primer capable of binding to a first priming site present in the first oligonucleotide may be used to prime unidirectional amplification. A second primer capable of binding to the complement of the second priming site present in the second oligonucleotide may be used concurrently to prime bidirectional amplification. In embodiments in which first and second priming sites are reverse complements of one another, the first and second primers may be the same. Amplification may be isothermal or thermal cycling.

Nucleic acid amplification methods useful in the methods of the disclosure are well known in the art and include, e.g., polymerase chain reaction (PCR), nucleic acid sequence-based amplification (NASBA), self-sustained sequence recognition (3SR), ligase chain reaction (LCR), transcription-mediated amplification (TMA), rolling circle amplification (RCA), and strand displacement amplification (SDA). Typically, bidirectional amplification is effected using PCR.

The methods of the disclosure may be readily multiplexed, permitting one or more oligonucleotides to be appended to a plurality of templates of distinct sequence in a single reaction. The templates may be separate nucleic acid molecules or separate loci of a single molecule such as a chromosome. In particularly useful multiplex embodiments, at least one, and typically two, common priming sites are appended to each of the plurality of templates. Thus, in another aspect, the disclosure provides methods for appending at least a one oligonucleotide directly to a plurality of nucleic acid templates of distinct sequence in a single reaction. In such multiplex embodiments of the disclosure, at least one oligonucleotide is appended to at least 2 templates of distinct sequence, typically at least 5 templates of distinct sequence, even at least 10, 20, 30, 40, or even at least 50 templates of distinct sequence, and may be appended to 100, 500, 1000, even 5000 or more templates of distinct sequence.

Each first oligonucleotide may include a first priming site that is common to all probes in a collection and each second oligonucleotide may include a second priming site that is common to all second oligonucleotides in a collection. In such embodiments, subsequent amplification of each of the templates of distinct sequence may be effected using common first and second primers. When the first and second priming sequences are reverse complements of one another, bidirectional amplification may be effected using a single common primer.

The multiplex methods of the disclosure may include the further steps of separating the plurality of templates from the plurality of probes and oligonucleotides, and then amplifying the plurality of templates in a common reaction.

In multiplex embodiments of the methods of the disclosure, the first and/or second oligonucleotide may usefully include a label ("barcode") that permits the separate identification of each unique template or product amplified therefrom. Barcode sequences are short nucleic acids having sequence that is designed algorithmically to maximize discrimination on a microarray displaying complements of the respective tags; a 1:1 correspondence as between tag sequence and nucleic acid to which it is appended permits each such nucleic acid to be identified by detection of the bar code uniquely associated therewith. See, e.g., Shoemaker et al., Nature Genet. 14(4):450 6 (1996); EP 0799897; Fan et al., Genome Res. 10:853 60 (2000); and U.S. Pat. No. 6,150,516, the disclosures of which are incorporated herein by reference in their entireties. In the methods of the disclosure, a distinct barcode sequence may be included in each species of first and/or each species of second oligonucleotide. In these embodiments, the terminal region of each species of oligonucleotide is distinct in sequence, and can anneal only to a single species of probe. The 1:1 correspondence as between tag sequence and template-appended oligonucleotide thus permits each template or product amplified therefrom to be identified by detection of the bar code uniquely associated therewith.

In one aspect, the number of target polynucleotides or sequences of interest amplified by a method of the invention depends on multiple factors known to those of ordinary skill in the art including, but not limited to, the type of nucleic acid e.g. RNA or DNA, that makes up the target polynucleotides, the quality of the sample, e.g. if and to what degree the target polynucleotides of the sample are degraded, the differences among the selection primer binding sites, the presence or absence of potentially interfering or homologous sequences in the sample, and the like. In one aspect, the number of target polynucleotides amplified in a method of the invention is in the range of from 10 to 100,000; and in another aspect, such number is in the range of from 10 to 1000; and in another aspect, such number is in the range of from 10 to 100, and in another aspect, such number is in the range of from 10 to 50.

The concentrations of probes and/or selection oligonucleotides are a matter of design choice for those of ordinary skill in the art; however, in one aspect, such concentrations may be selected that are equivalent to those used in conventional amplification reactions, such as PCR reactions. Generally, such concentrations are selected following well-known principles of hybridization reactions and PCR primer selections for example, disclosed in the references cited below.

The methods disclosed herein may also be used for RNA analysis and detection. In particular, methods for RNA detection that do not require conversion of the RNA, typically by reverse transcription, to cDNA are also disclosed. The methods may be particularly useful for degraded RNAs, such as RNA from FFPE (formalin fixed paraffin embedded) samples, and small RNAs, such as miRNA, microRNAs, and siRNAs because these RNAs may be too short to use as template for reverse transcription. In another aspect, methods for appending one or more small RNA molecule directly to a single stranded oligonucleotide (capture probe), at one or more defined sites internal to the template are disclosed. The presence of the appended RNA molecule is detected by its 3' end extension using capture probe as template for DNA synthesis. The capture probe may be designed to provide one or more sites for priming the subsequent amplification of adjacent probe regions. The methods may be readily multiplexed, permitting a plurality of RNAs to be appended, in a single reaction, to a plurality of capture probes. In multiplex embodiments in which the appended capture probes provide one or more common priming sites, the plurality of templates may generate and then be concurrently amplified using primers common to all templates. Such multiplexed amplification reactions provide the ability to detect the presence of multiple small RNA molecules with high specificity and uniformly amplify all generated templates so solve the problems with converting small RNA molecule into cDNA for subsequent amplification.

Small interfering RNA and miRNA have recently become the subjects of intense research interest in biology and medicine due to their apparent roles in the regulation of gene expression via a process termed RNA interference (RNAi). The ability of organisms to dynamically respond to their environment is due in large part to regulation of gene expression. Regulation of gene expression is also important for the ability of multicellular organisms to generate the proper type and number of cells to create complex tissues and organs at the appropriate locations and times during development. Control of gene expression by a cell requires perception of environmental signals and appropriate response to these signals. Proteins have been studied extensively as mediators of these signals and a large number of protein-based regulators of gene expression are known. In contrast, the process of RNAi and, in particular, the role of siRNA and miRNA in regulating gene expression is just beginning to be elucidated.

Micro-RNA molecules are produced as cleavage products of larger precursors that form self-complementary hairpin structures. The miRNA molecules are typically 21 or 22 nucleotides in length and are processed by a ribonuclease (such as Dicer in animals and DICER-LIKE1 in plants). A miRNA precursor can by polycistronic containing several different hairpin structures that each give rise to a different miRNA molecule. Small interfering RNA molecules are also generally about 21 or 22 nucleotides long but, on the other hand, are produced from long hairpin precursors processed such that several different siRNA molecules can arise from a single hairpin structure.

There has been great interest in the analysis of small RNAs, such as short interfering RNAs (siRNAs), microRNAs (miRNA), tiny non-codingRNAs (tncRNA) and small modulatory RNA (smRNA), since the discovery of siRNA biological activity over a decade ago. The levels of individual miRNAs seem to vary with developmental stages and tissue types. The level of fluctuation may be correlated with phenotype, mRNA levels, or protein levels for better biological insight. Thus quantitative measurements of miRNA may be of great importance. Further, viral miRNAs have been identified and may play a role in latency (see Pfeffer et al., Science, 304: 734-736 (2004)), making the detection and quantification of miRNAs a potentially valuable diagnostic tool.

Due to small size of small RNAs the number of the methods which can be successfully used for detection and measuring different levels of small RNAs is limited. The most used method of detecting multiple RNAs is direct labeling the small RNAs at 3' end hybridizing it to corresponding microarray. See, e.g., Liu et al., Proc. Nat'l Acad. Sci. USA, 101: 9740-9744 (2004); Thomson et al., Nature Methods, 1:1-7 (2004); and Babak et al., RNA, 10:1813-1819 (2004). However, this method required to use the substantial amount of material.

In one aspect, methods for modifying a small RNA molecule by the covalent attachment of additional sequence information to facilitate further analysis of the small RNA molecule are described. The method may conveniently be understood by reference to the illustrative reaction of FIG. 7. As illustrated in FIG. 7A, the small RNA molecule 710 is hybridized to region 721 of capture probe 720. Capture probe 720 includes at least one small RNA complementarity region 721, decoding (barcode) region 22, and at least one common sequence (primer) regions 23 and 42 that may be used for PCR amplification. In the annealing step, small RNA sequence 710 hybridizes to the 3' end of the capture probe at complementarity region 721. Then the 3' end of the small RNA 710 is extended by a polymerase activity in step 701 using capture probe 720 as template. The information from capture probe 720 is copied into newly synthesized molecule 7100. Newly synthesized molecule 7100 is represented by dotted line in FIG. 7A. The small RNA molecule is covalently attached to the 5' end of the newly synthesized linear molecule 7100. The product of the reaction is a duplex molecule formed by the capture probe and the extended small RNA. As shown in FIG. 7B, the duplex molecule may then be dissociated in step 702 and the capture probe removed or destroyed. In some aspects the capture probe may contain cleavable bases like uracil (U) that facilitate degradation as discussed above. Capture probe may also contain chemical modifications like biotin which can be used for affinity separation of capture probe using streptavidin beads to separate biotinylated material from non biotinylated material. Free capture probe may also be degraded by single stranded exonuclease treatment.

The method generates newly synthesized molecule 7100, which contains the complement of the decoding sequence flanked at both sides by common sequences and can be used as template for PCR amplification reaction. P1 and P2 primers can be used for priming at the priming sites located at common sequences as schematized in FIG. 7B. The product of step 703 is an amplification product that includes a double stranded PCR product as shown.

The presence of the specific barcode sequence in PCR product is indicative of the presence of the small RNA. Each RNA target 710 has a different probe 720 having a unique barcode 22 that is indicative of the identity of the RNA 710. Detection of a barcode 22 can be used to determine if the RNA 710 was present. The PCR product can be detected by multiple methods like microarray hybridization or by sequencing. Small RNA molecule 710 is typically at least 10 nt in length, more typically at least 15, 20, 25, or 30 nt in length or even more in length.

Capture probe 720 can be synthesized chemically, using solid phase procedure well known in the art, by ligation of smaller, chemically-synthesized fragments, or produced enzymatically by DNA synthesis or other recombinant methods. Capture probe 720 is typically at least about 40 nt in length, often at least 50, 75, 100, 125 or 150 nt in length, at times at least about 200 nt, 300 nt, 400 nt, or 500 nt or more in length, and when derived from recombinant nucleic acid molecule can be at least 1000 nt (1 kb), 2 kb, 3 kb, 4 kb, 5 kb, 10 kb, 20 kb, 30 kb, 40 kb or 50 kb in length.

RNA complementarity region 721 of capture probe 720 is designed to have sufficient length and sufficient sequence complementarity to small RNA molecule 710 as to permit annealing of RNA molecule 710 to capture probe 720 under hybridization conditions of desired stringency.

RNA complementarity region 721 of capture probe 720 is typically at least 10 nt in length, more typically at least 15, 20, 25, or 30 nt in length or even more in length. Capture probe 720 includes at least decoding (barcode) region 22. Decoding region 22 is non complementary to template and designed for detection of the product without directly detecting sequence of interest. Often decoding sequence is composed of artificially designed sequences which are optimized for specific detection by hybridization.

Each capture probe 720 contains individual decoding sequence. At the end of the reaction each specific product has the individual decoding sequence attached to it. Decoding region 22 of capture probe 720 is typically at least 10 nt in length, more typically at least 15, 20, 25, or 30 nt in length or even more in length. Probe 720 is typically further designed to include a sequence, a "priming site", to which an oligonucleotide primer can anneal in later steps.

In another series of embodiments, illustrated in FIG. 8, methods for specific selection of RNA molecules with defined 3' end positions are disclosed. During template/primer based synthesis the primers that form completely paired 3' ends with the template are successfully extended by nucleic acid synthesis. However the position of the 3' end relative to the template will have no effect on the efficiency of the extension, so two primers with even one base difference in the position of the 3' end will be extended by synthesis. In order to mitigate this problem, additional steps can be added.

Figure 8A:
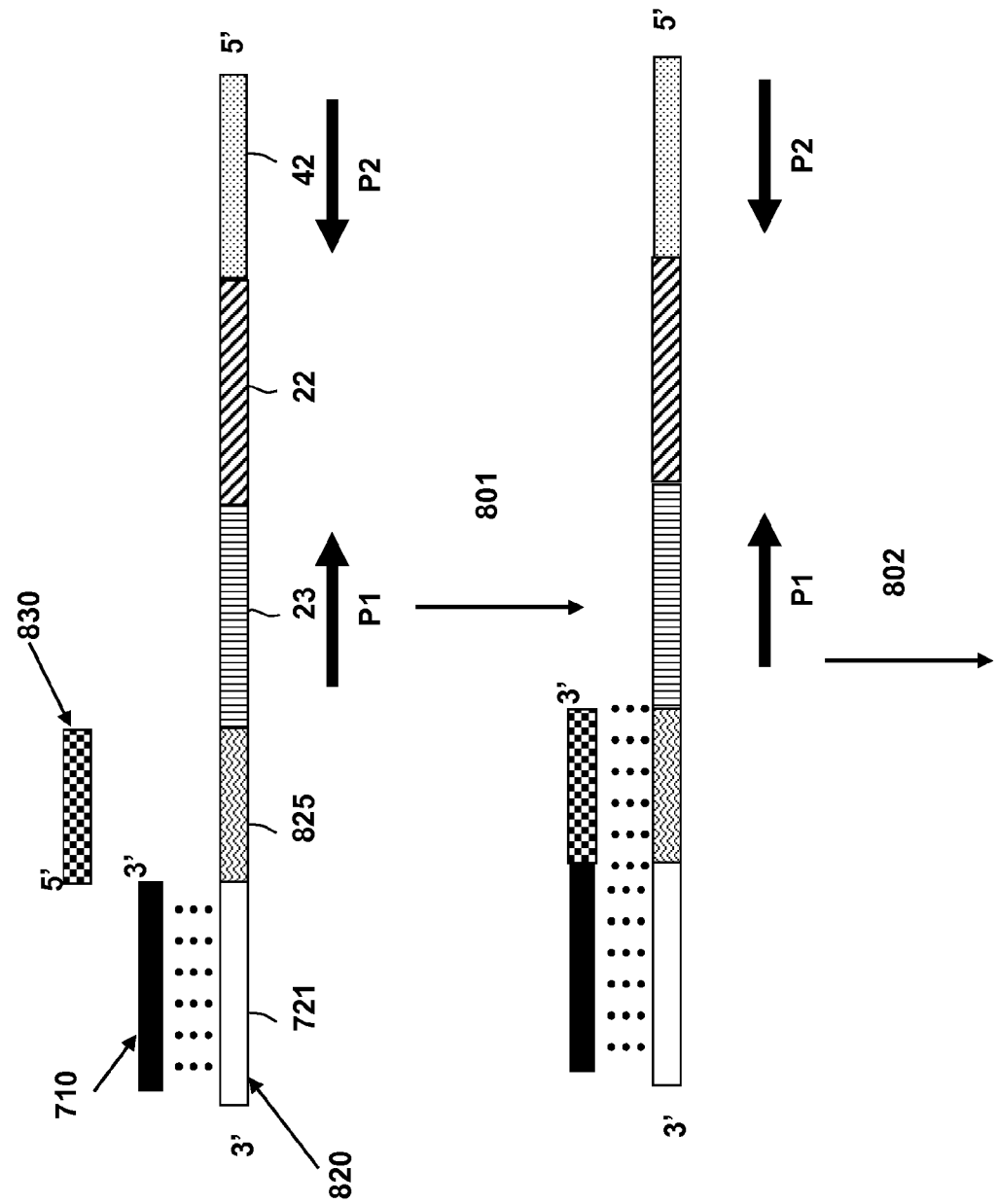
FIG. 8A is a schematic illustrating a small RNA molecule being appended directly to a single stranded capture probe and ligation of a selection oligonucleotide to the 3' end of the RNA.

In the first step, illustrated in FIG. 8A, small RNA molecule 710 is concurrently annealed to single stranded capture probe 820. Capture probe 820 varies from capture probe 720 because it has additional region 825 added for specific selection of the RNA molecule 3' end position. Probe 820 includes from 3' end: RNA complementarity region 721, position selection region 825, first common sequence (primer 1) region 23 used for PCR amplification, decoding (barcode) region 22, and second common sequence (primer 2) region 42 used for PCR amplification. Additional oligonucleotide 830 is added and contains sequence complementary to region 825. In probe 820 primer 1 and primer 2 are directed toward each other as illustrated. P2 is not complementary to 42 but is of the same sequence so that it hybridizes to the extension product formed when probe 820 is used as template for formation of an extension product. In the absence of the extension product P2 does not hybridize and a PCR product is not formed.

In the annealing step, small RNA 710 needs to be hybridized to the 3' end of the capture probe 820 at RNA complementarity region 721. Oligonucleotide 830 hybridizes to selection region 825 of capture probe 820. Annealing of small RNA 710 and oligonucleotide 830 can be performed simultaneously or in any sequential order. As a result of hybridization both small RNA 710 and oligonucleotide 830 anneal to probe 820 and form a hybrid molecule duplex with a nick between 830 and 710. In step 801, illustrated in FIG. 8A, the nick between small RNA molecule 710 and oligonucleotide 830 is closed by ligation covalently attaching the RNA molecule to the oligonucleotide 830. Then the 3' end of the ligated molecule is extended in step 802 by using capture probe 820 as template. The information from probe 820 is copied into newly synthesized molecule 8100.

The products resulting from step 802 are shown in FIG. 8B, illustrating that the small RNA and oligonucleotide 830 are covalently attached to 5' end of the newly synthesized linear molecule 8100. The product of the reaction is duplex molecule formed by capture probe 820 and the extension product. The duplex molecule may then be dissociated and the capture probe removed or destroyed as described above. In some aspects it is important to remove the capture probe before PCR amplification because while it is not template for P2 it is template for extension using P1. Using the difference between the melting temperature of individual molecules, small RNA and oligonucleotide 830 and ligated hybrid molecule, nucleotide synthesis at higher temperatures can be performed to select the longer more stable hybrid molecule.

If oligonucleotide 830 is composed of deoxiribonucleotides (DNA), DNA polymerase extending only from deoxiribonucleotide primer can be used to even more increase specificity of small RNA detection. Only hybrid molecule containing DNA at 3' end will be extended with these DNA polymerases. Different types of ligases may be used in one or more of the disclosed methods. Ligases that may be used, depending on the application, include for example, T4 RNA ligase 1 (RNA/DNA or DNA/DNA with or without RNA or DNA template), T4 RNA ligase 2 (RNA/RNA or RNA/DNA with RNA or DNA template), T4 RNA ligase 2, truncated (RNA/DNA or RNA/RNA with RNA template or without template), T4 RNA ligase 2, truncated K227Q (same), T4 DNA ligase (DNA template RNA/DNA or DNA/DNA). See also, Bullard and Bowater (2006) Biochem. J. 398, 135-144, which is incorporated herein by reference.

In another aspect, the disclosure provides an alternative selection of RNA molecule with defined 3' end. The ligation of oligonucleotide 830 to small RNA on capture probe can be replaced by synthesis. If the sequence of region 825 is a homopolymer region, only RNA molecules with the correct position 3' end will be extended after addition of the corresponding single nucleotide. For example, it region 825 is one or more A bases the extension can be done initially in the presence of only T, A subsequent extension with all four bases present may then be used provided that only extension products from the first extension can be used as substrates for the second extension. This may be by blocking of unextended RNAs or by extending under conditions such that the RNA does not serve as template for initiation of synthesis and only the partially extended product extends further. Oligonucleotide 830 is typically at least 4 nt in length, more typically at least 6, 10, 15, 20, 25, 30, or 50 nt in length or even more in length.

For ligation based 3' end selection capture probe includes position selection region 25. Position selection region 25 of capture probe 20 is designed to have sufficient length and sufficient sequence complementarity to oligonucleotide 30 to permit annealing of probe 20 to oligonucleotide 30 under hybridization conditions of desired stringency. Position selection region 25 of capture probe 20 is typically at least 4 nt in length, more typically at least 6, 10, 15, 20, 25, 30, or 50 nt in length or even more in length.

In another embodiment, illustrated in FIG. 9, small RNA 710 is appended to capture probe 920. The capture probe contains two primer regions P1 in 23 and P2 in 21 that are oriented in the same direction. Positioning the PCR primers in the same direction prevents the formation of PCR product from the capture probe. Moreover the sequence of the second primer P2 is the reverse complement of the sequence primer used for PCR. In this case degradation or complete removal of capture probe 920 from reaction is not required. The sequence of the primer cP2 located at 5' end of the probe 920 also contains the degradable or cleavable bases designated at U.

Figure 9A:
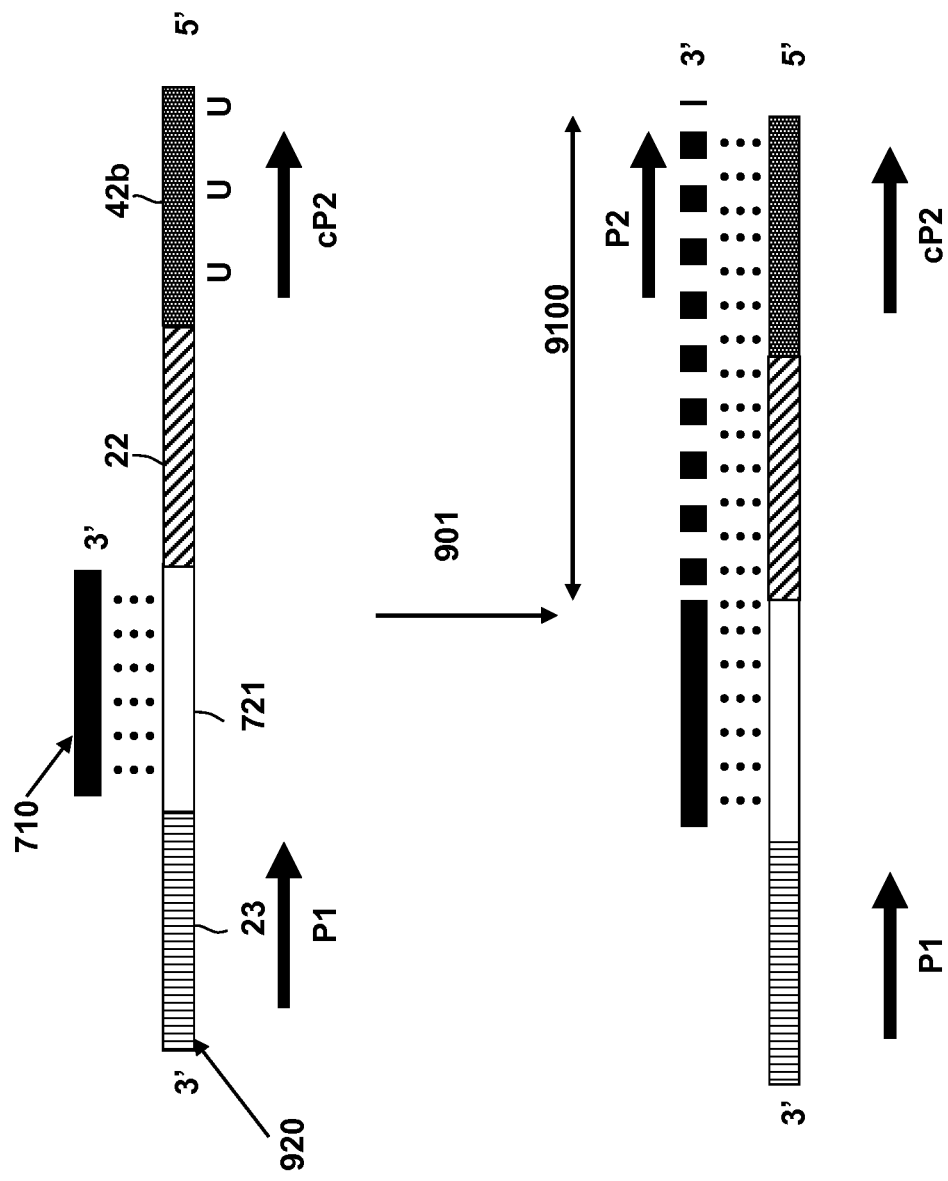
FIG. 9A is a schematic illustrating a method for using capture probes with primer sequences pointing in the same direction. The small RNA molecule hybridizes to the capture probes and is extended. The capture probe also contains cleavable bases at the 5' end.

In the first step of the method, illustrated in FIG. 9A, small RNA molecule 710 is annealed to complementary region 721 of the capture probe 920. Capture probe 920 contains starting from 3' end: P1 common primer sequence region 23; RNA complementary region 721; decoding (barcode) region 22; and cP2 reverse compliment second common primer sequence region 921 used for PCR amplification. The directions of the PCR primers are indicated by arrows.

In step 901, the 3' end of the small RNA 710 is extended by synthesis using capture probe 920 as template. The information from the capture probe in copied into newly synthesized molecule 9100. Newly synthesized molecule 9100 is represented by a dotted line and includes a sequence that is complementary to the priming sequence in region 21.

The products resulting from step 901 are shown in FIG. 9A lower panel, illustrating that the small RNA 710 is covalently attached to the 5' end of the newly synthesized linear molecule 9100. The product of the reaction is a duplex molecule formed by template and newly synthesized linear molecule. In the newly synthesized linear molecule P2 is the complement of cP2.

In step 902, illustrated in FIG. 9B, the region 42b of capture probe 920 is degraded, using for example cleavable bases that may be incorporated into region 42b. For example, deoxyuridine residues (presented as "U" on the illustration) incorporated into the sequence of the region 42b is released by uracil-DNA glycosylase ("UDG") creating apurinic ("AP") sites. AP sites may then be cleaved enzymatically for example by using an AP endonuclease, chemically for example by imidazole, or decompose naturally. Natural decomposition of AP site can be accelerated by heat and pH. The degradation of that portion of capture probe 920 is shown in FIG. 9B. Incorporating the ribonucleotide bases into region 42b of capture probe 920 allows the removal of ribonucleotide bases by RNase degrading enzymatic activities or by nicking RNaseH like activities. Ribonucleotide bases also can be chemically degraded.

As the result of cleavage the sequence of region 42b should be completely degraded or partially degraded. Cleavage of the base should result in formation of polynucleotide with 5' H or 5' P end. Cleavage leaves a 3' overhanging end of 9100 as shown in FIG. 9B lower panel.

Next, in step 903 as illustrated in FIG. 9C, the 3' end of the linear molecule 9100 forms an intra-molecular loop in step 903 and is ligated to the recessed 5' end of the probe 920 in step 904 by intra-molecular loop formation. The length of the 3' end of linear molecule 9100 forming the loop is typically at least 10 nt in length, more typically at least 15, 20, 30, 50, 100 or 200 nt in length or even more in length. The sequence at the 3' end of the linear molecule 9100 preferably contains no complementary bases to form duplex structure with its internal sequence, or it may contain 1, 2, 5, 10, 15 and 20, or more complementary bases which can form duplex structure with internal sequence, resulting in a hairpin loop structure.

After ligation the newly synthesized primer P2 sequence located at the 3' end of linear molecule is linked to the 5' end of the region 22 of probe 920. The regions 721 and 22 are flanked at both sites by primer P1 and P2 sequences and can be used as template for PCR amplification reaction as schematized in FIG. 9C.

Figure 10A:
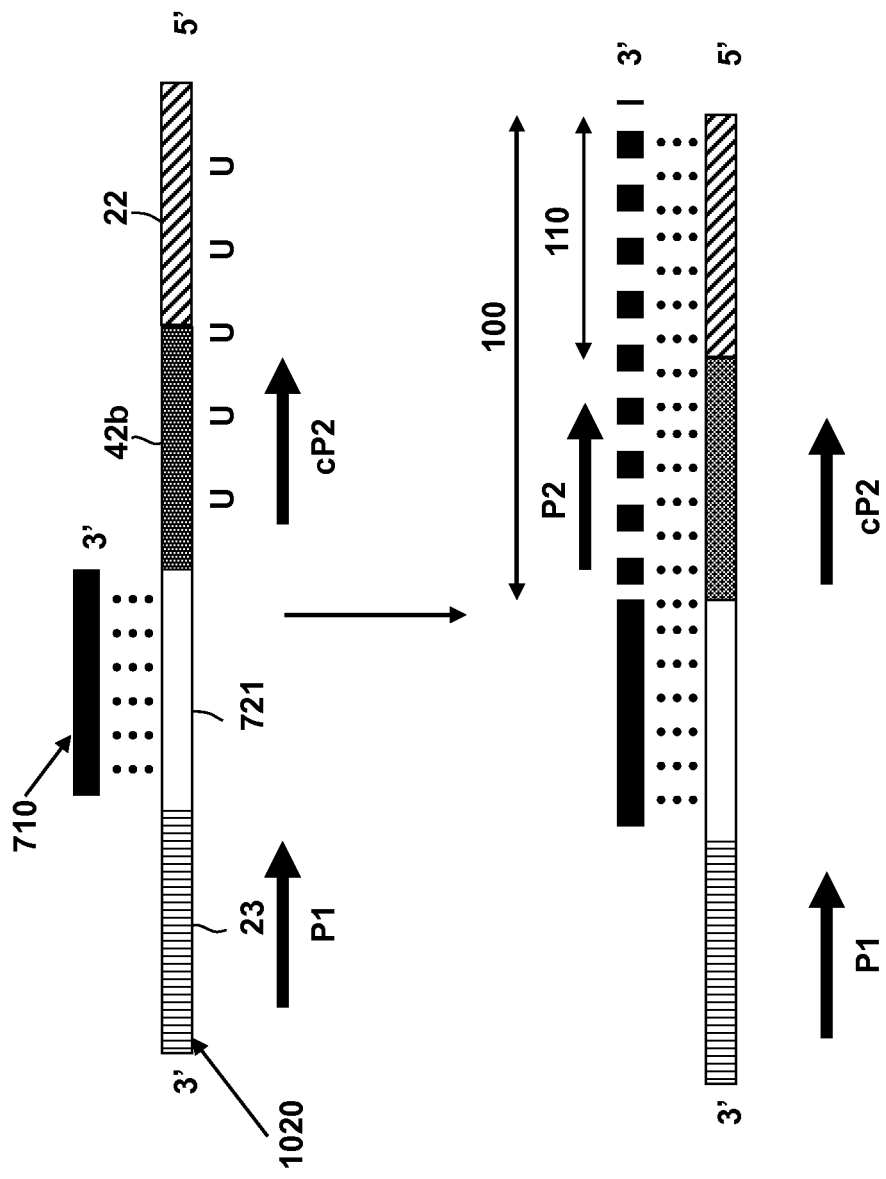
FIG. 10A illustrates hybridization of the RNA to a capture probe having P1 and P2 facing the same direction and extending the RNA to incorporate the complement of P2 and a region that can loop back to form a ligatable 3' end.

In other embodiment, illustrated in FIG. 10A, another composition of the capture probe 1020 containing two primer regions facing in the same direction is used for intra-molecular ligation described above in FIG. 9. Capture probe 1020 contains starting from 3' end: P1, common primer sequence region 23; RNA complementary region 721; cP2 reverse compliment and second common primer sequence region 42b used for PCR amplification, and decoding (barcode) region 22. The sequence of the primer cP2 and decoding region 22 are located at the 5' end of the capture probe and preferably contain degradable or cleavable bases, for example uracils that can be treated with a uracil DNA glycosylase followed by AP endonuclease treatment to cleave that region of the capture probe. The resulting small fragments are preferably small and can be disassociated from the extended RNA by, for example, denaturation.

In the first step of the method, illustrated in FIG. 10A upper panel, the mall RNA molecule 710 is annealed to complementary region 721 of the capture probe 1020. In the next step, illustrated in the lower panel, the 3' end of the small RNA 710 is extended by synthesis using capture probe 1020 as template. The information from the capture probe is copied into newly synthesized region 100. Newly synthesized region 100 is represented by a dotted line. Region 42b containing complementary sequence of primer cP2 is converted by synthesis into primer sequence P2, and region 22 containing decoding sequence is converted into complimentary sequence 110.

Figure 10B:
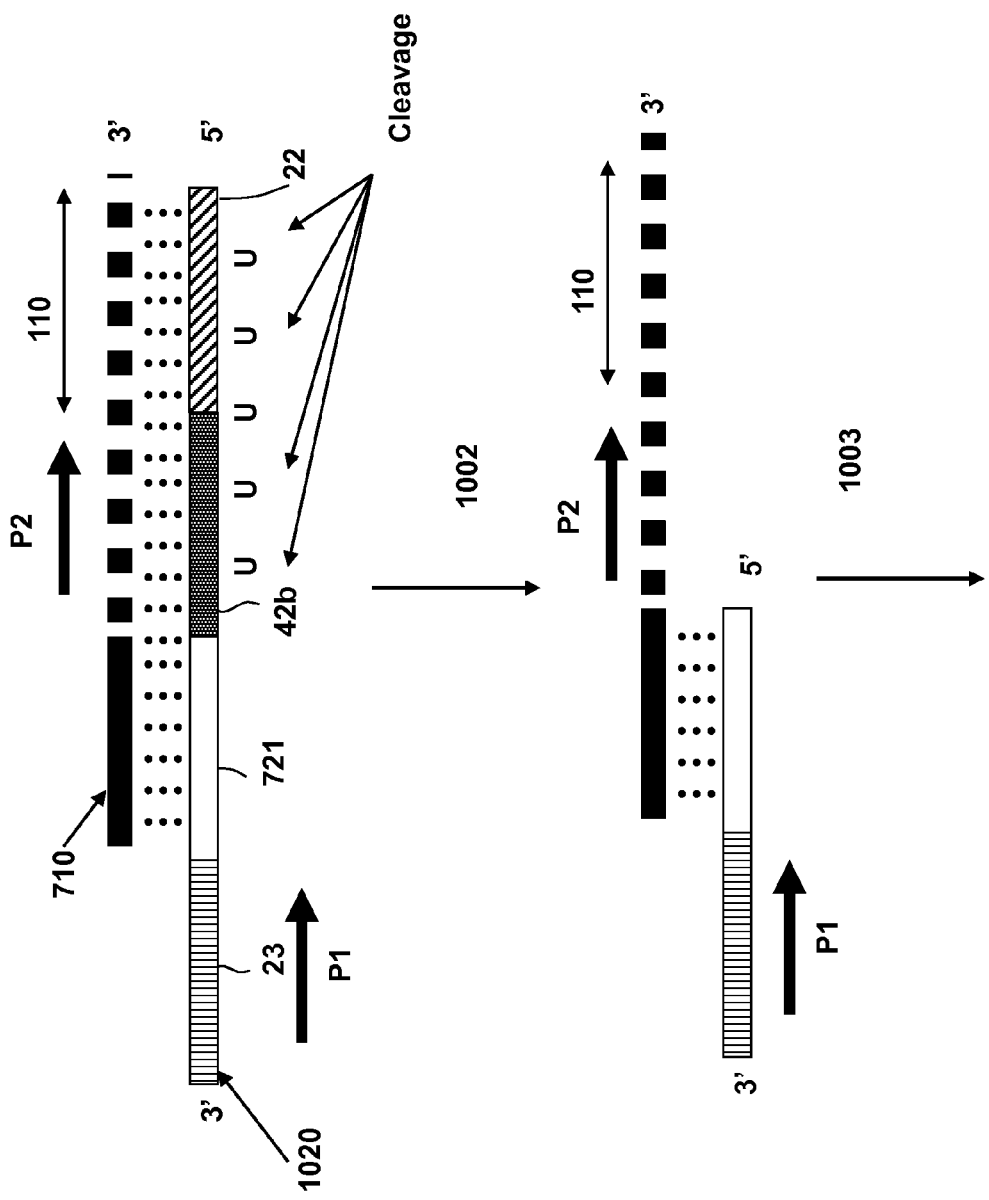
FIG. 10B illustrates cleavage of the sequence located at the 5' end of the capture probe at the positions marked by "U" resulting in degradation of the 5' end of the capture probe.
Figure 10D:
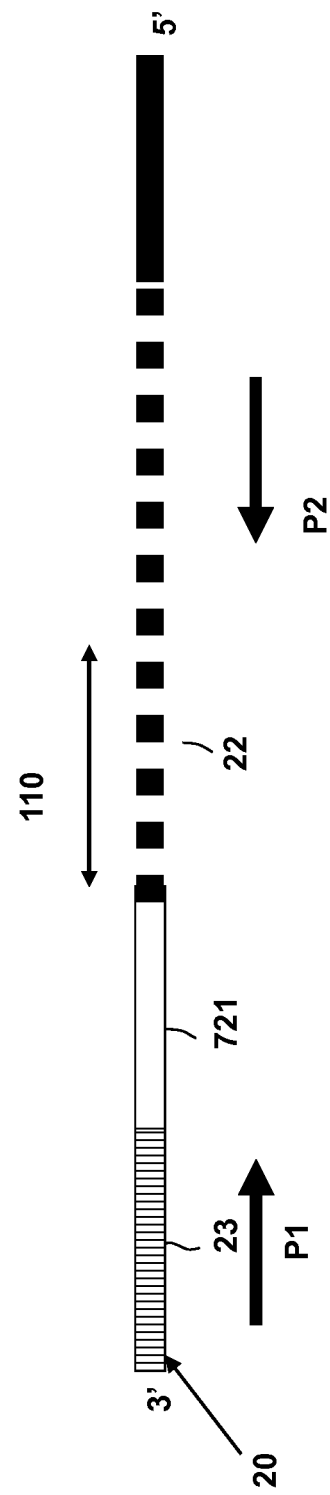
FIG. 10D illustrates the final product of the intra-molecular ligation with primer sequences facing toward each other so that the sequence between the primers can be amplified by PCR.

In next step, illustrated in FIG. 10B, the regions 42b and 22 of capture probe 1020 are degraded in step 1002 at the cleavable bases with formation of duplex with single stranded 3' end. In step 1003 an intra-molecular loop structure is formed. In final steps 1004 and 1005, illustrated in FIG. 10C, the 3' end of the linear molecule 100 ligates to the recessed 5' end of the probe 1020 by intra-molecular loop formation. After ligation the newly synthesized primer P2 sequence and sequence 110 containing complementary sequence for decoding sequence located at 3' end of linear molecule is linked to the 5' end of the region 721 of probe 1020. In the newly joined molecule the regions 721 and sequence 110 are flanked at both sites by primer P1 and P2 sequences and can be used as template for PCR amplification reaction as schematized in FIG. 10D.

Figure 11B:
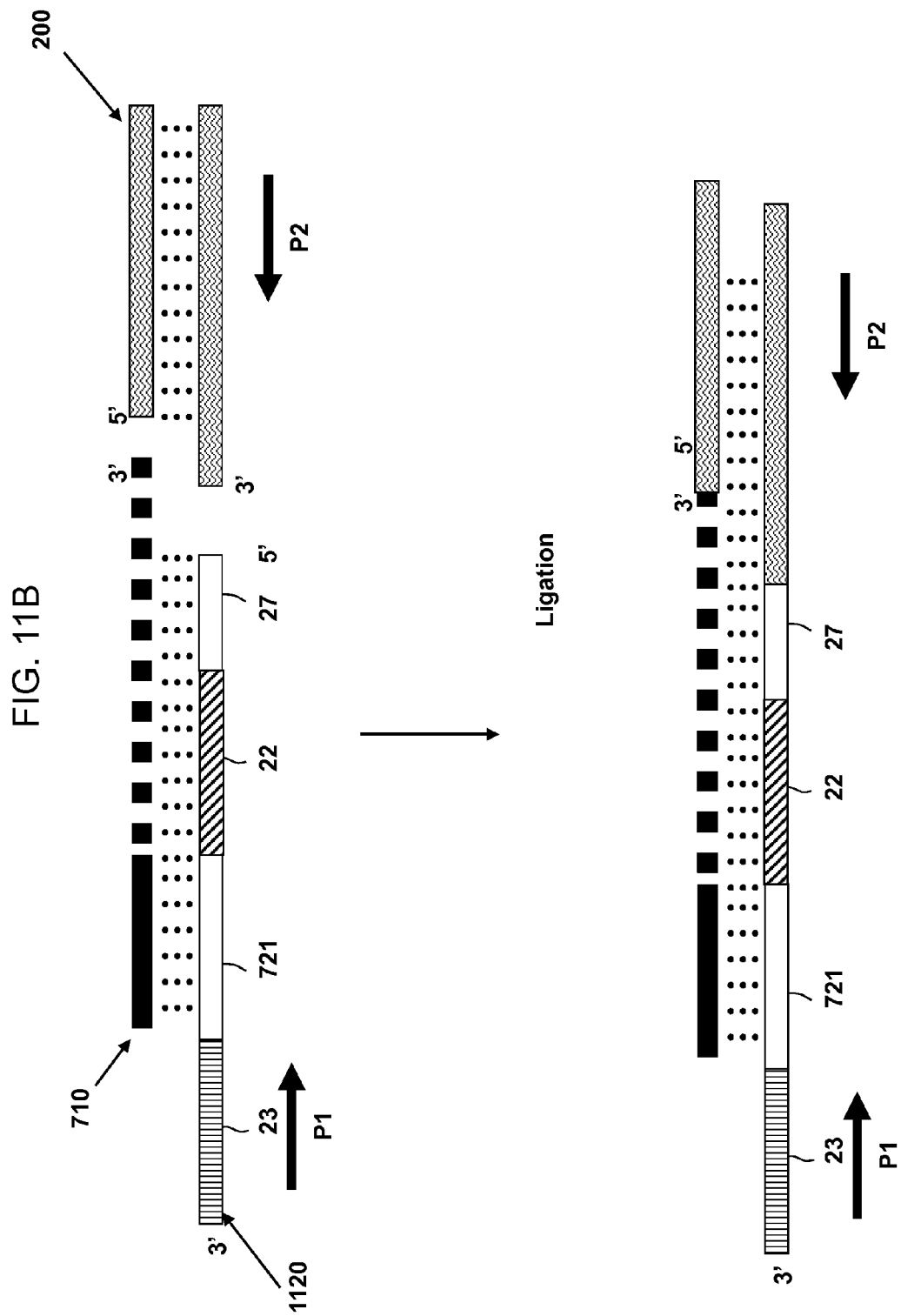
FIG. 11B illustrates adding a duplex molecule which contains a second primer sequence to the cleaved end of the duplex between the probe and linear molecule by ligation.

In another series of embodiments, different methods of detecting small RNA molecules by using of the capture probe 20 containing only one primer P1 and attaching another primer P2 to regenerate template amplifiable by PCR are described. One method is illustrated in FIGS. 11A and 11B. Capture probe 20 contains, starting from the 3' end: P1 common primer sequence region 23; RNA complementary region 24; decoding (barcode) region 22, and region 27 containing a restriction endonuclease cleavage site sequence. In the first step of the method, illustrated in FIG. 11A, the small RNA molecule is annealed to complementary region 24 of the capture probe 20. Next, the 3' end of the small RNA 10 is extended by synthesis using capture probe 20 as template. Newly synthesized linear molecule 100 forms a duplex with capture probe 20. In the next step, illustrated in the lower panel of FIG. 11A, the duplex molecule is cleaved at region 27 by restriction endonuclease. The cleavage preferably generates a ligatable end, for example a single stranded overhang or "sticky end" although a blunt end may also be generated and used for ligation.

The duplex molecule 200 has an end that is compatible with the end generated by restriction digestion and can be ligated to the end of the molecule as shown in FIG. 11B. The double stranded adapter 200 has primer region P2 and its complement.

In other embodiments the position orders for regions 21c, 73, and 22 in probe 70 can be use at any combination, except the region 71 should be at 3' end of the probe 70.

The additional non complementary or partial complementary to template sequence can be used for creating the loop between regions 21c and 71 of probe 70. The length of the loop between regions 21c and 21a is typically at least 1 nt in length, more typically at least 5, 10, 20, 30, 50, 100 or 200 nt in length or even more in length.

Other non complementary or partial complementary to template sequences can be added to the 5' or 3' end or both ends of the probe 70. The addition of non complementary sequences at 3' end of the probe 70 will generate duplex between probe 70 and template 10 with non paired single stranded 3' end. The non paired 3' end should be degraded by single stranded exonuclease activity for subsequent steps.

Figure 12B:
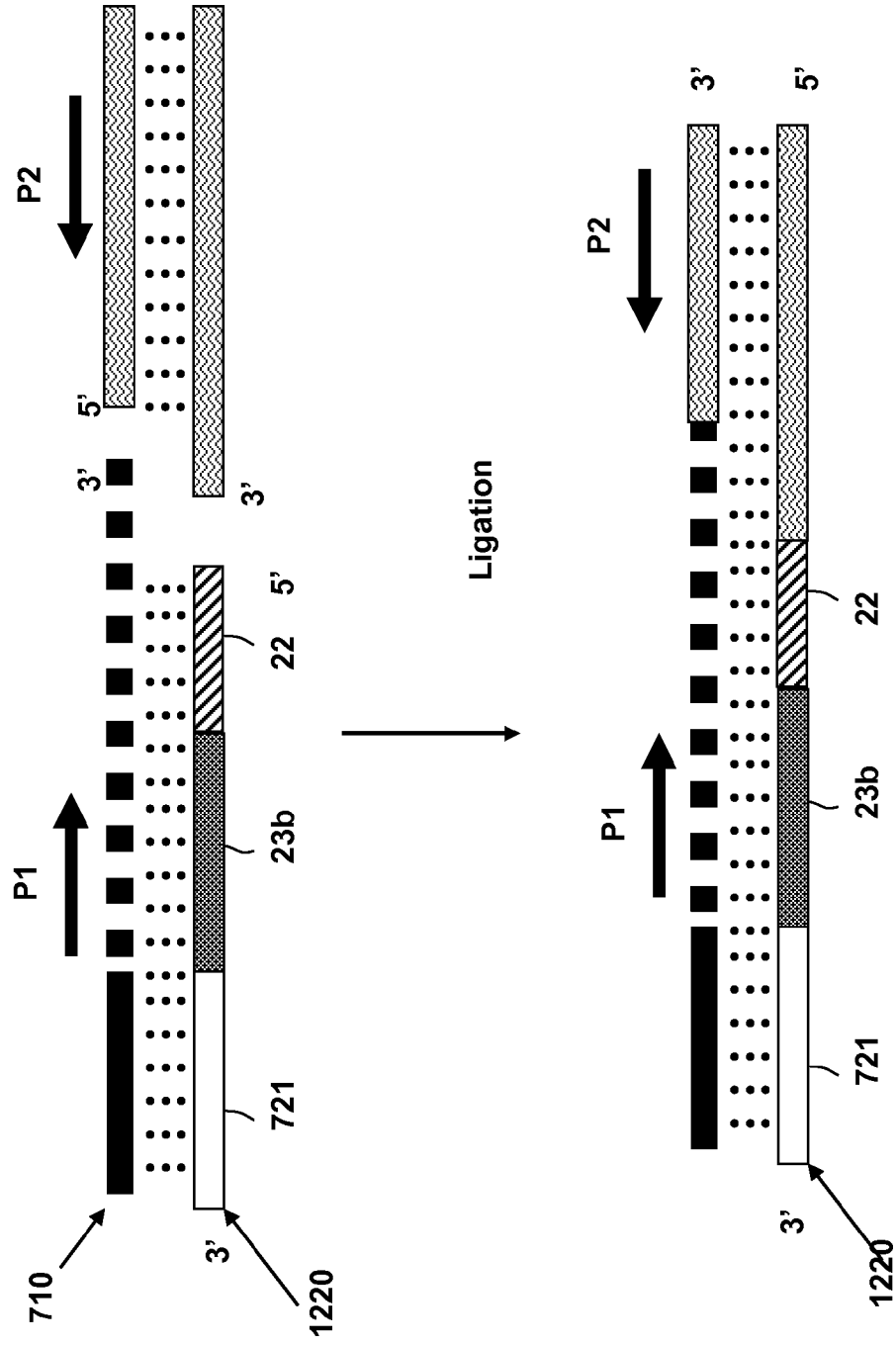
FIG. 12B shows ligation of the adapter containing the P2 sequence to the overhang generated by restriction enzyme cleavage to generate target with P1 and P2 priming sequences.
Figure 12C:
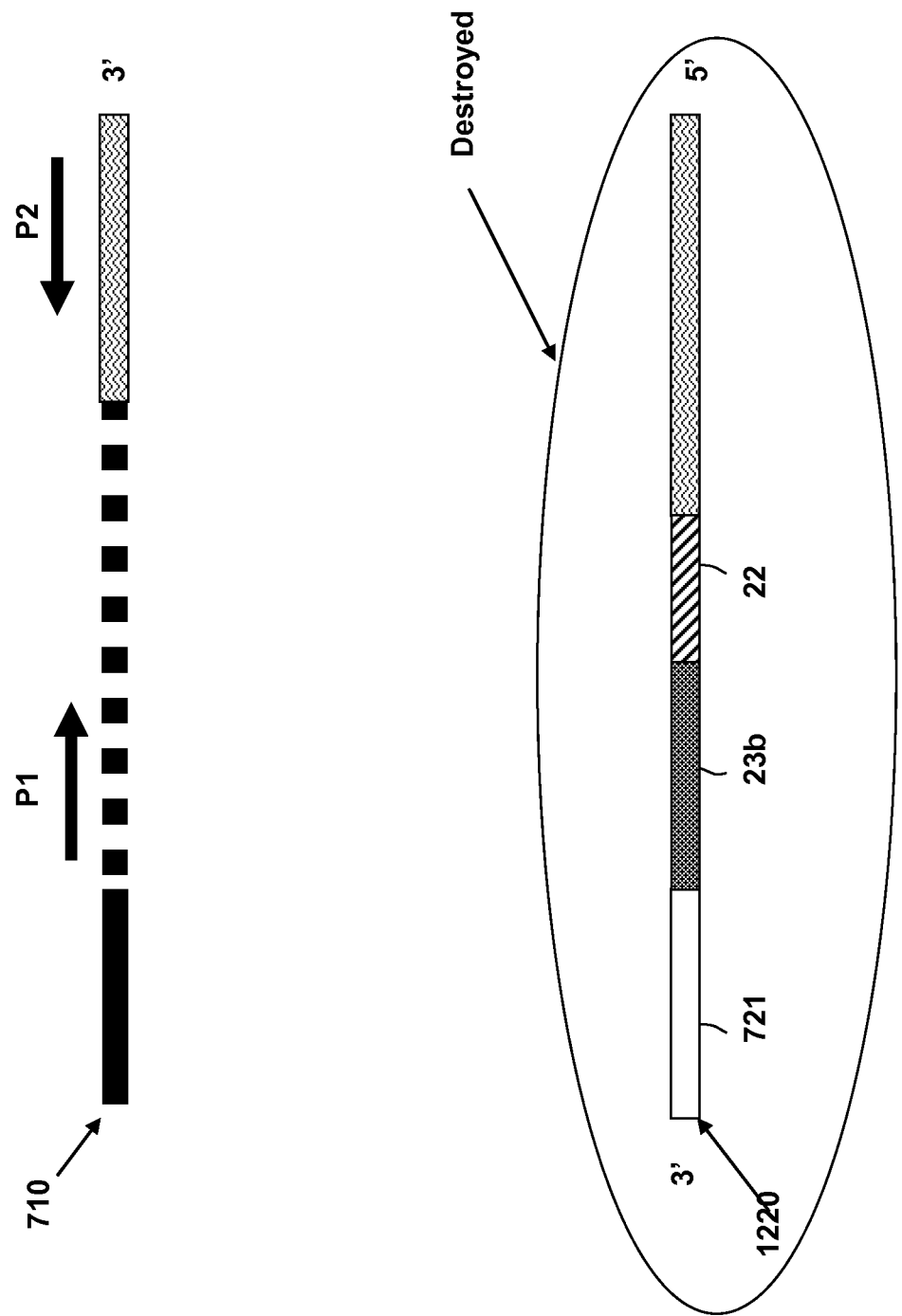
FIG. 12C shows the PCR template and optional degradation of the capture probe.

In another embodiment, illustrated in FIG. 12, the first or second probes, or ligatable oligonucleotides may include deoxyuridine residues as substitutes for all or for a fraction of the thymidine residues. This embodiment provides for the elimination of excess non-reacted and nonspecific product by incorporating the cleavable nucleotides in the sequence of the first and second probe and ligatable oligonucleoide.

In order to preserve the final product of the reaction the common primer P2 is appended to 3' end common sequence attached to 3' end of the linear molecule and new strand is synthesized with natural nucleotides using linear molecule as template as illustrated in FIGS. 12A and 12B. The deoxyuridine residues are presented as "U" on the illustration.

After synthesis the mixture is treated with uracil-DNA glycosylase ("UDG"), which catalyzes the release of free uracil from uracil-containing DNA, creating apurinic ("AP") sites. AP sites may then be cleaved enzymatically for example by using an AP endonuclease, chemically for example by imidazole, or decompose naturally. Natural decomposition of AP site can be accelerated by heat and pH.

In yet a further alternative, the probe can include purines such as 8-oxoguanine, 8-oxoadenine, fapy-guanine, methyl-fapy-guanine, fapy-adenine, aflatoxin B-fapy-guanine, 5-hydroxy-cytosine, and 5-hydroxy-uracil, that mimic damaged purines. Fpg glycosylase will release these residues from DNA and remove the resulting AP site, leaving a 1 nucleotide gap.

In another embodiment, the deoxyuridine triphospate nucleotide is used instead of thymidine triphostate nucleotide in synthesis of linear molecule 100 and extending recessed 3' end. After synthesis completed the deoxyuridine nucleotide is degraded, removed, or diluted from the product. In order to preserve the final product of the reaction the common primer P2 is appended to 3' end common sequence attached to 3' end of the linear molecule and new strand is synthesized with natural nucleotides using linear molecule as template as similarly to the methods described above. Only final product contains the sequence of interest which is flanked by two primer sites. Any non specific extensions of first probes which does not have the second primer sequence at the end will be degraded UDG.

FIG. 13A is a schematic showing a method for using a capture probe containing a single primer sequence and attaching a second primer sequence by ligation. The duplex between the newly synthesized linear molecule and the capture probe is formed after extending captured small RNA molecule 10 by DNA synthesis as described above to add new sequence 100 that is complementary to the capture probe. In FIG. 13A lower panel the duplex between the capture probe and the extended RNA is denatured into two separate single strand molecules: capture probe and linear molecule. The capture probe also can be degraded. In FIG. 13B upper panel a duplex is formed between oligonucleotide 30 and the extended target RNA. Oligonucleotide 30 has a 5' region that is complementary to a second primer sequence 40 that will be ligated to the 3' end of the linear molecule extension product. The duplex molecule has single strand sequence at the 5' end, which is complementary to the sequence at 3' end of the linear molecule, and forms a duplex structure between the linear molecule and probe 30. The nick between the linear molecule and oligonucleotide 40 is closed by ligation. The ligated molecule contains sequences of first and second primers facing forward each other and can be amplified by PCR with two primers.

Figure 14B:
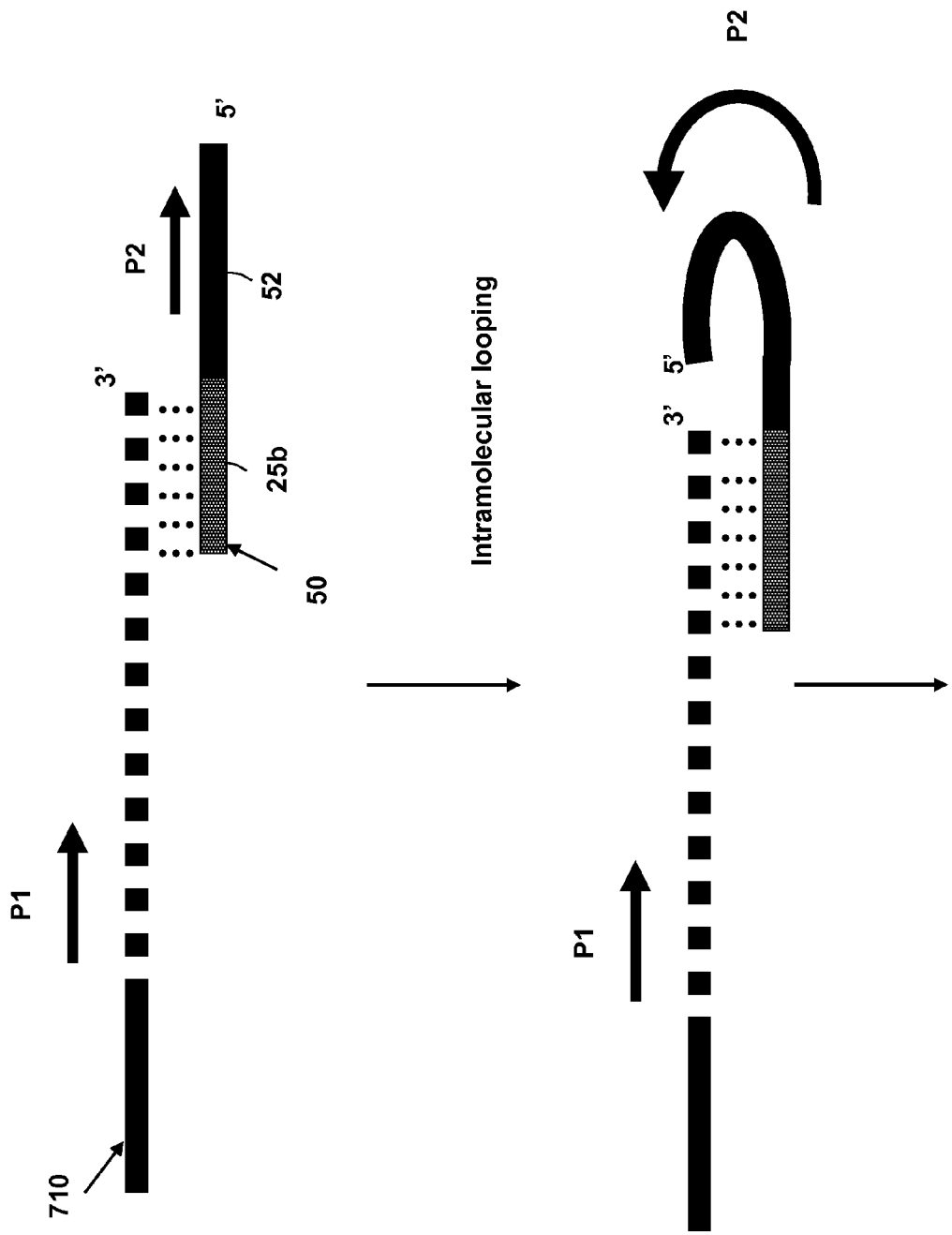
FIG. 14B shows appending the single stranded oligonucleotide to the 3' end of the linear molecule after hybridization of the single stranded oligonucleotide.
Figure 14C:
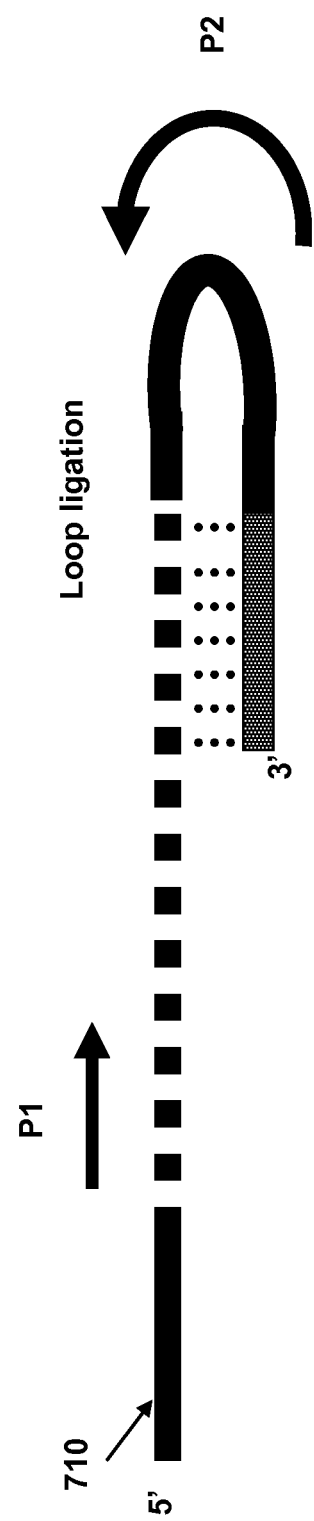
FIG. 14C shows the intra-molecule looping between the recessed 3' end of the linear extension product and the single stranded 5' end of appended oligonucleotide.

FIG. 14A is a schematic representation of a method for using capture probes containing only one primer sequence and attaching a second primer sequence by ligation. The duplex between the newly synthesized linear molecule and capture probe is formed by extending captured small RNA molecule 10 by DNA synthesis as described above. In the lower panel of FIG. 14A the newly synthesized duplex is denatured to form two separate single strand molecules, the capture probe and the newly extended linear molecule including the RNA 10 and newly synthesized DNA 100. The capture probe also can be degraded to leave only the newly extended linear molecule. As shown in FIG. 14B single stranded oligonucleotide 50 is hybridized to the end of the linear molecule via a basepairing interaction between the 3' end of the linear molecule and region 51 of probe 50. Region 52 of probe 50 forms an intra-molecular loop as shown in the lower panel of FIG. 14B. The 5' end of probe 50 loops back on itself and is juxtaposed near the 3' end of the linear extension product. The ends can be joined by ligation as shown in FIG. 14C. Now primer P2 can be used in combination with primer P1 to amplify the linear extension product.

Figure 15A:
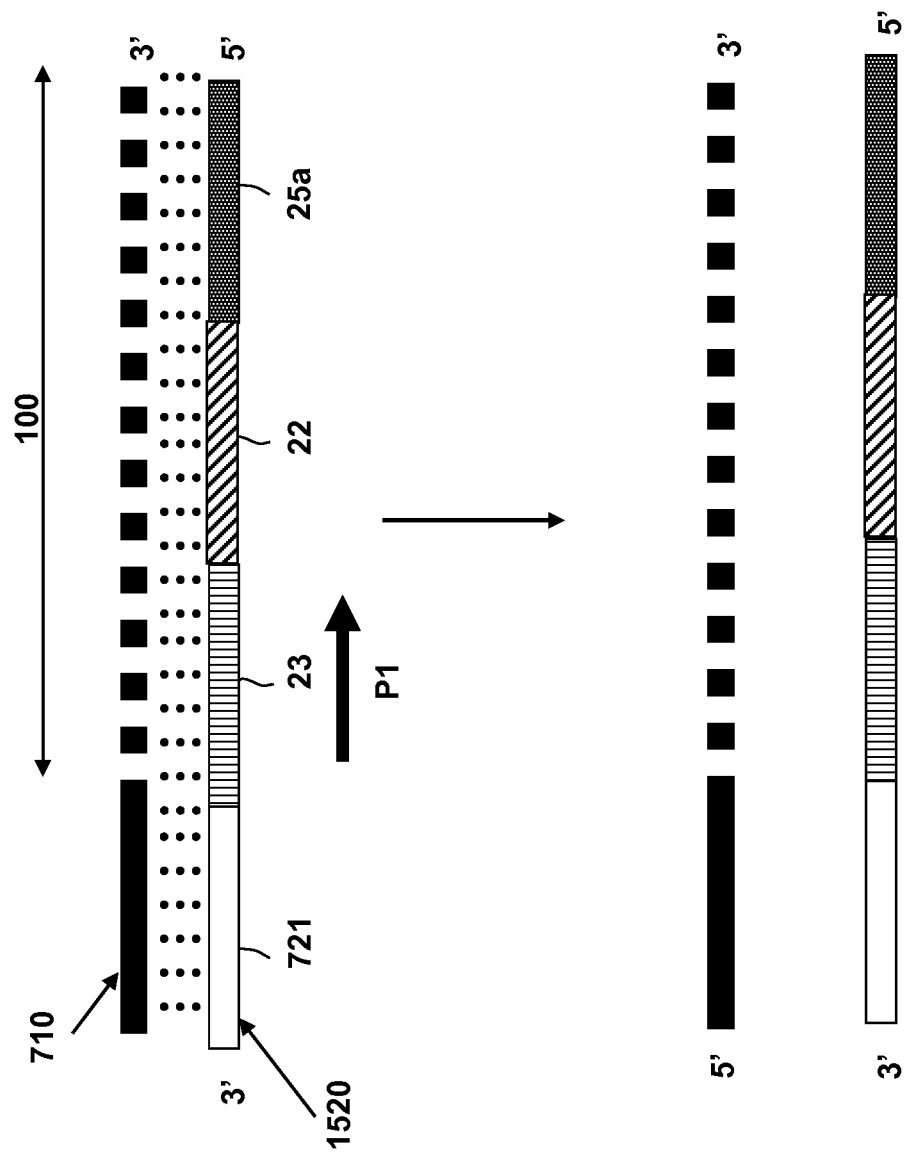
FIG. 15A shows a method for using capture probes containing one primer sequence and attaching second primer sequence by DNA synthesis.
Figure 15B:
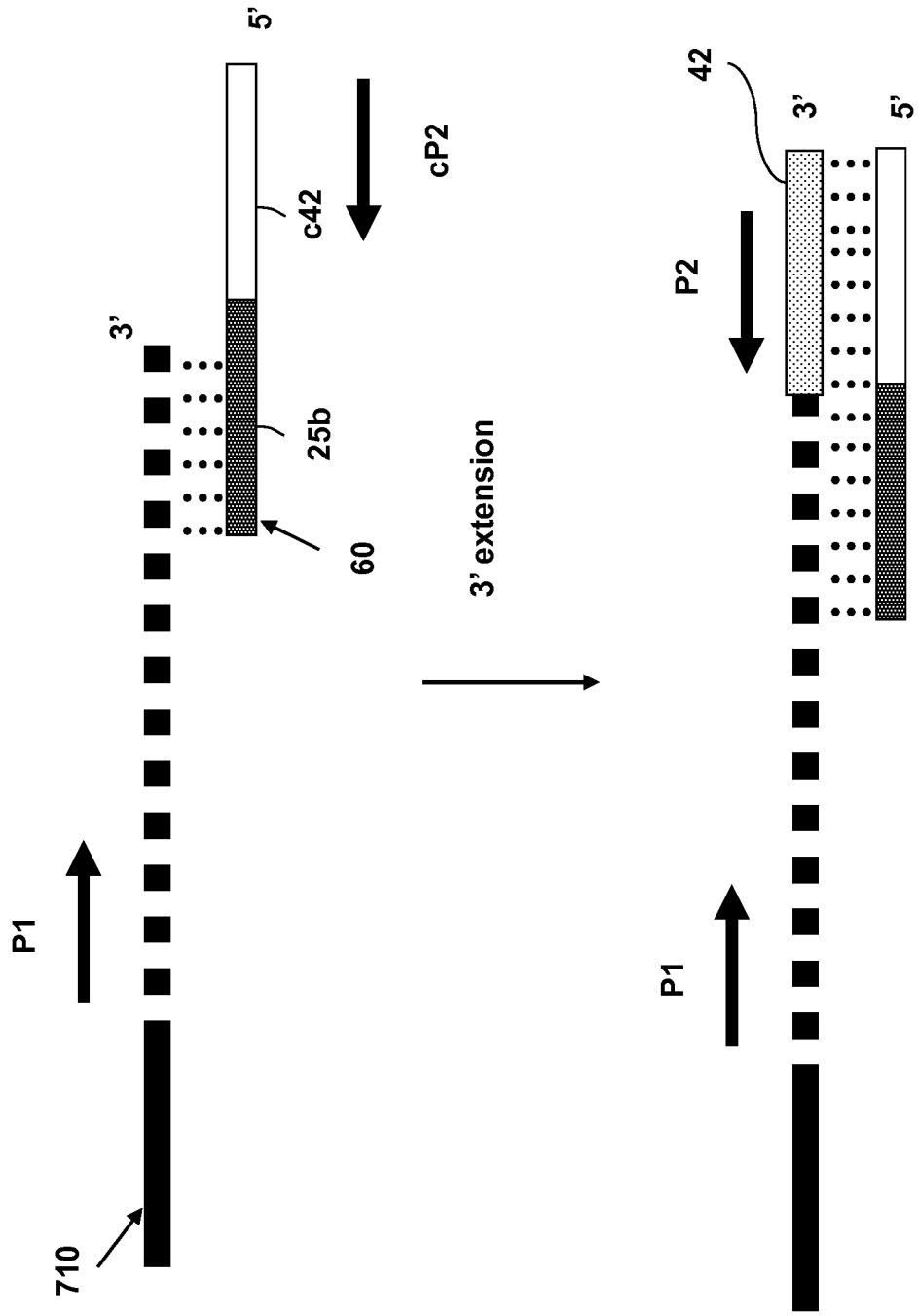
FIG. 15B illustrates the extension of the 3' end of the linear molecule using a hybridized oligonucleotide as template for DNA synthesis.

FIG. 15A is a schematic of a method for using capture probes containing only one primer sequence and attaching a second primer sequence by DNA synthesis. The duplex between newly synthesized linear molecule and capture probe 20 is formed after extending captured small RNA molecule 10 by DNA synthesis as described above. As shown above, the linear extension product is separated from the capture probe 20 by denaturation or degradation of the capture probe, as shown in the lower panel of FIG. 15A. As shown in FIG. 15B probe 60 can be hybridized to the end of the extension product and the 3' end of the extension product can be further extended to add the complement of region 62 which contains the primer 2 sequence (the complement of the primer 2 binding site) as shown in the lower panel. Newly synthesized sequence at 3' end of linear molecule contains the second primer sequence. Extended linear molecule contains sequences of first and second primers facing forward each other and can be amplified by PCR with two primers.

Figure 16A:
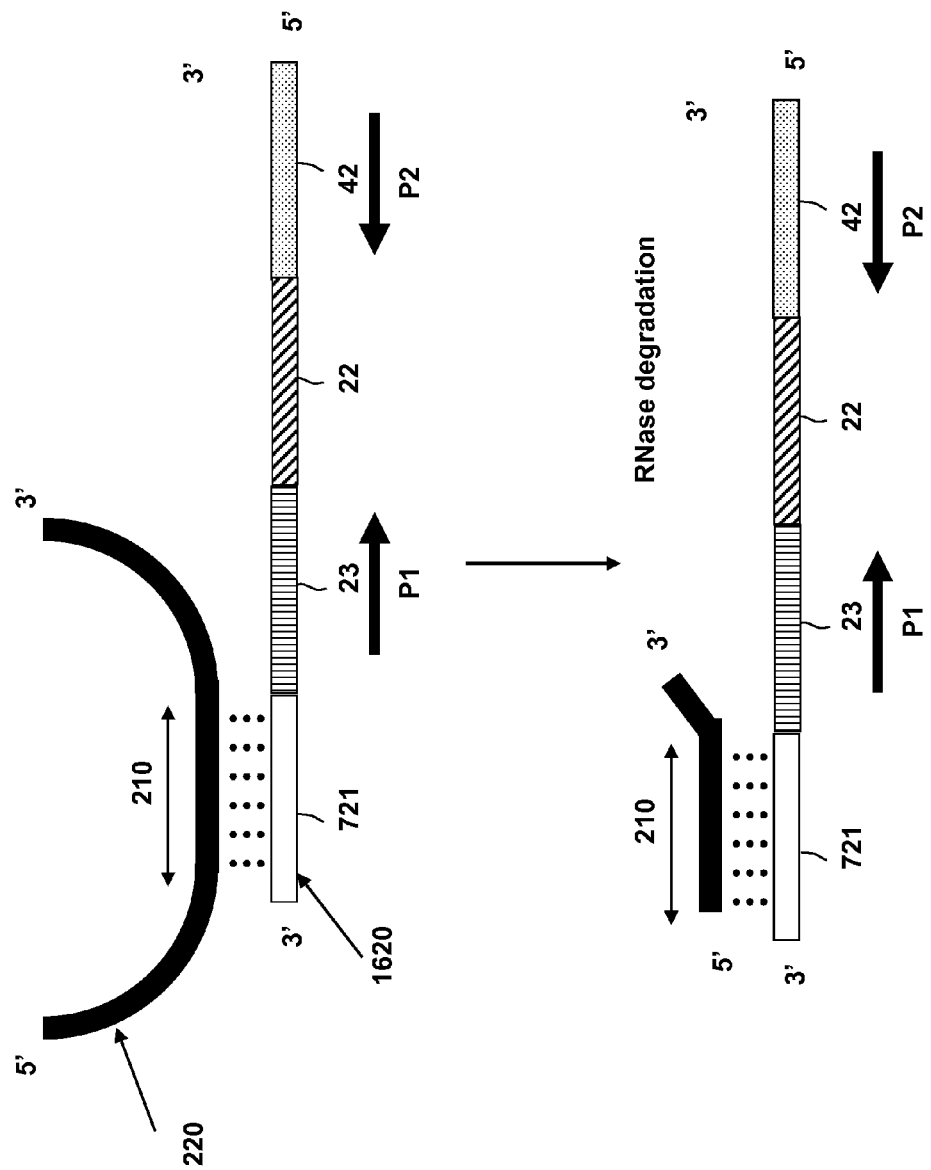
FIG. 16A illustrates a method for appending primer sequences to longer RNA molecules by degrading the overhanging regions.
Figure 16B:
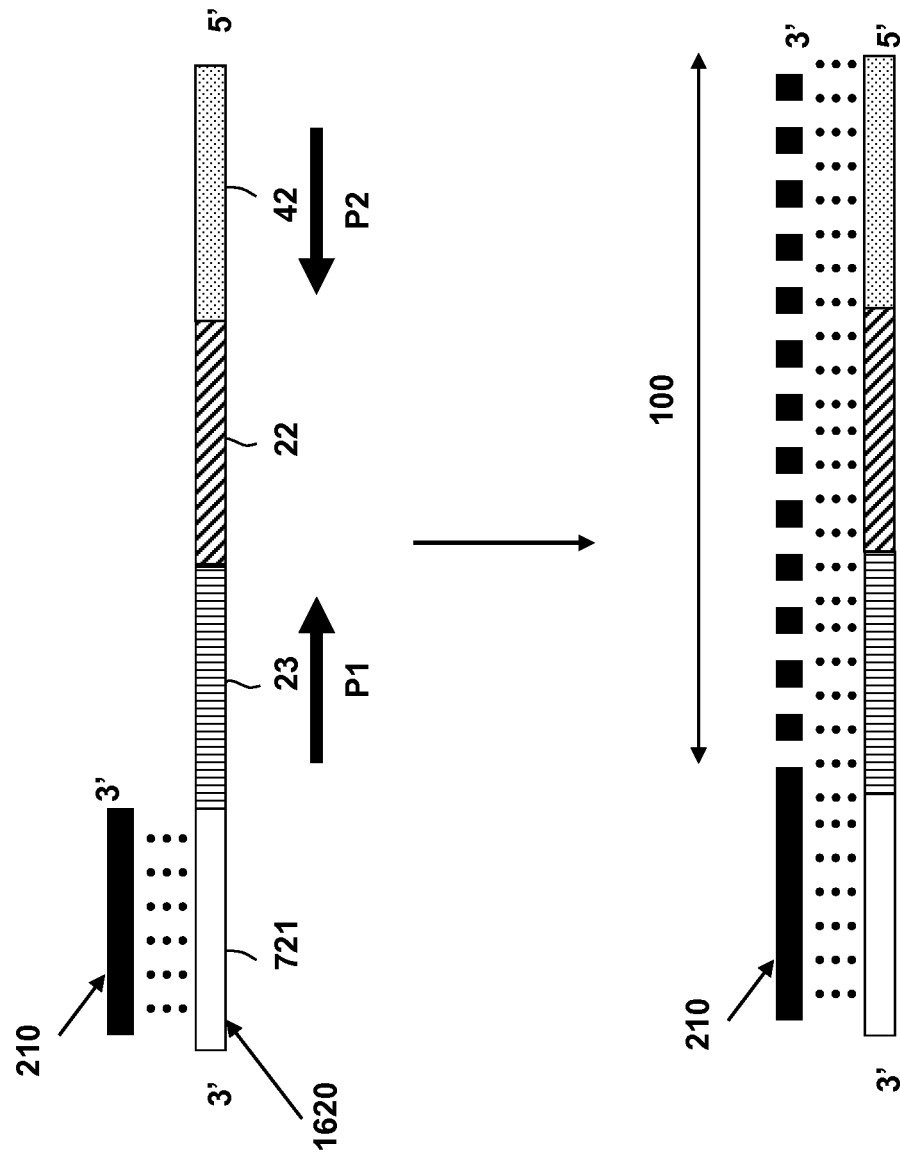
FIG. 16B illustrates extension of the remaining duplex region using the capture probe as template for DNA synthesis.

FIG. 16A illustrates a method for use with longer RNA molecules such as the one shown 200. The capture probe 20 has a region 24 that is complementary to a sub-region 210 of longer RNA 200. The RNA hybridizes with a 5' and 3' overhang as shown. RNase is used to degrade the single stranded part of the RNA molecule as shown in the lower panel of FIG. 16A. RNase activity degrades non paired parts of the RNA molecule and produces the duplex between capture probe and non degraded RNA molecule with a 3' mispaired end as shown. The mispaired 3' base can be removed by exonuclease activity to form the structure shown in FIG. 16B. The remaining small piece of RNA 210 can now be extended and treated as described above and as shown in the lower panel of FIG. 16B. The template molecule for amplification PCR can be produced by any combinations of the methods described above.

Figure 17A:
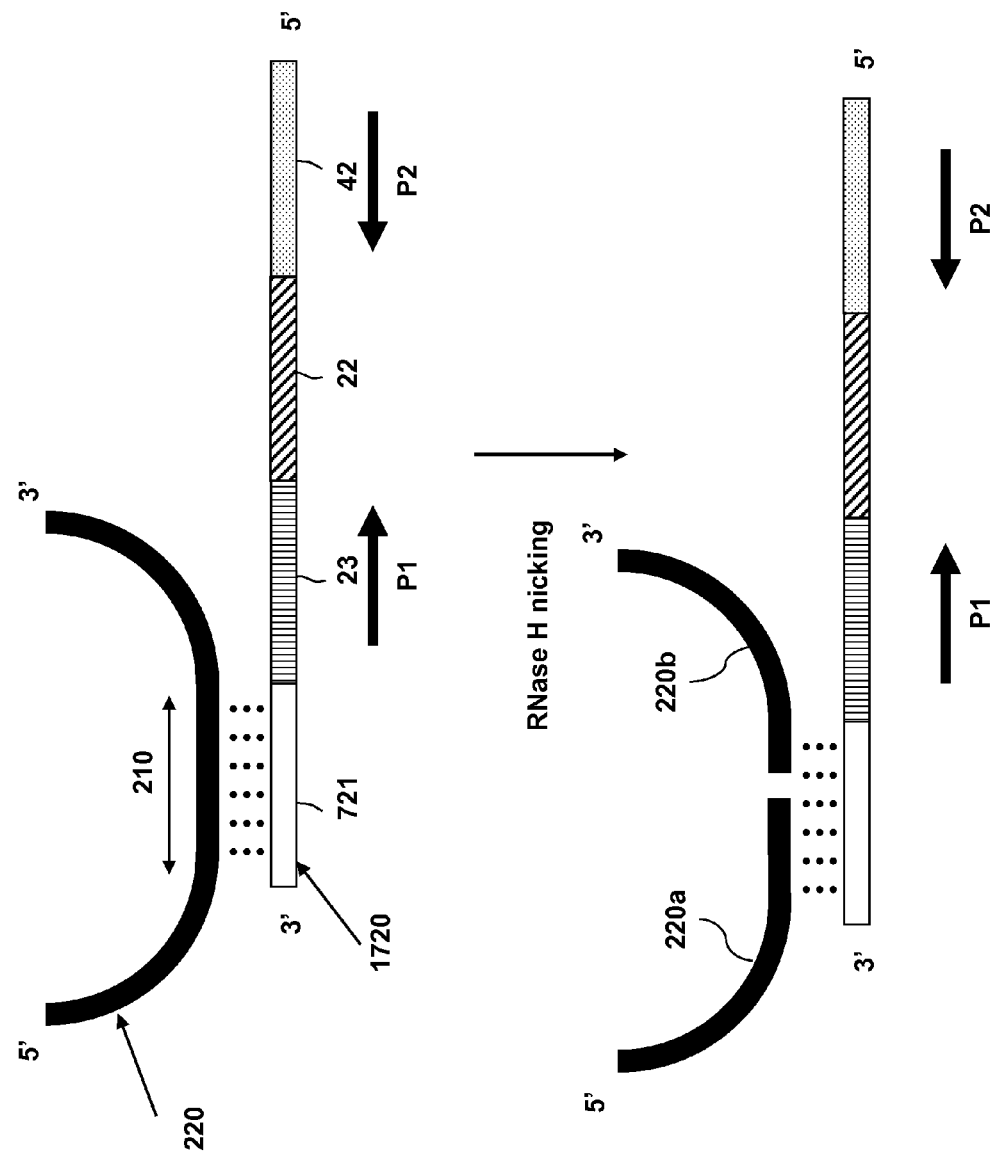
FIG. 17A illustrates hybridization of a longer RNA to a capture probe resulting in single stranded overhangs and a partial duplex region followed by RNase H nicking within the duplex region.
Figure 17B:
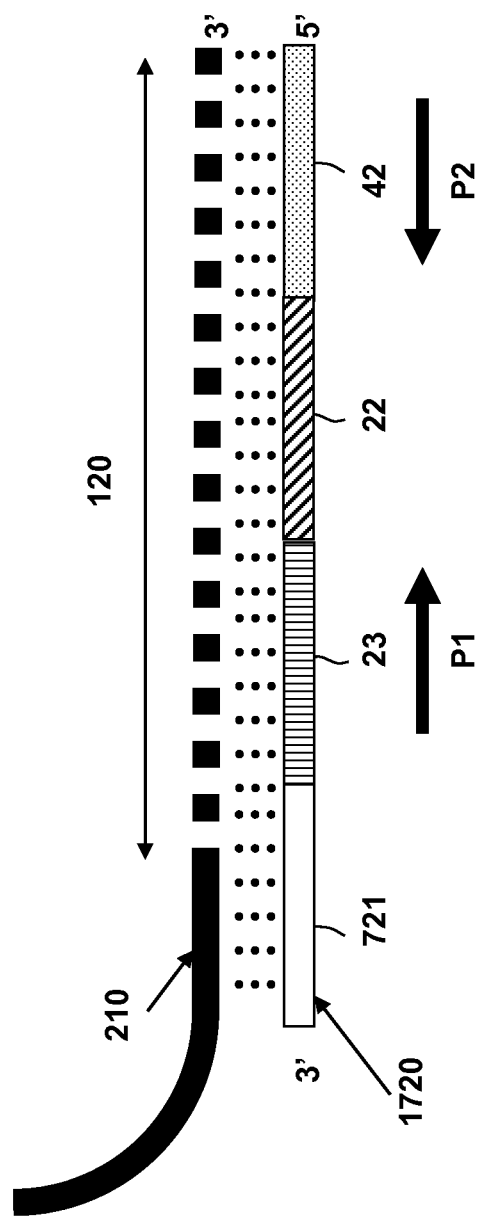
FIG. 17B illustrates extension from the nick to incorporate priming sequences into the extension product.

FIG. 17 illustrates a method for appending primer sequences to a longer RNA molecule. In one aspect, the capture probe contains the capture sequence which is complementary to the specific part of the RNA molecule and forms a duplex structure with the RNA molecule. As shown in FIG. 17B the RNA molecule in the RNA/DNA hybrid duplex is nicked using an RNase H like activity and generating a new 3' end that can be extended as shown in FIG. 17C by DNA synthesis. The template molecule for amplification PCR can be produced by any combinations of the methods described above.

As used herein, the term amplification includes the production of RNA transcripts by polymerization driven from a phage promoter. More typically, however, the amplification product is DNA produced by polymerization primed using one or more oligonucleotides ("primers") that are capable of hybridizing to one or more priming sites within one or more of the oligonucleotides appended to the template. For example, a first primer capable of binding to a first priming site present in the first oligonucleotide may be used to prime unidirectional amplification. A second primer capable of binding to the complement of the second priming site present in the second oligonucleotide may be used concurrently to prime bidirectional amplification. In embodiments in which first and second priming sites are reverse complements of one another, the first and second primers may be the same. Amplification may be isothermal or thermal cycling.

Nucleic acid amplification methods useful in the methods disclosed herein are well known in the art and include, e.g., polymerase chain reaction (PCR), nucleic acid sequence-based amplification (NASBA), self-sustained sequence recognition (3SR), ligase chain reaction (LCR), transcription-mediated amplification (TMA), rolling circle amplification (RCA), and strand displacement amplification (SDA). Typically, bidirectional amplification is effected using PCR.

The methods disclosed herein may be readily multiplexed, permitting one or more oligonucleotides to be appended to a plurality of templates of distinct sequence in a single reaction. The templates may be separate nucleic acid molecules or separate loci of a single molecule such as a chromosome. In particularly useful multiplex embodiments, at least one, and typically two, common priming sites are appended to each of the plurality of templates. Thus, in another aspect, methods are provided for appending at least a one oligonucleotide directly to a plurality of nucleic acid templates of distinct sequence in a single reaction.

In such multiplex embodiments, at least one oligonucleotide is appended to at least 2 templates of distinct sequence, typically at least 5 templates of distinct sequence, even at least 10, 20, 30, 40, or even at least 50 templates of distinct sequence, and may be appended to 100, 500, 1000, even 5000 or more templates of distinct sequence.

Each first oligonucleotide may usefully include a first priming site that is common thereamong, and each second oligonucleotide may usefully include a second priming site that is common thereamong. In such embodiments, subsequent amplification of each of the templates of distinct sequence may be effected using common first and second primers. When the first and second priming sequences are reverse complements of one another, bidirectional amplification may be effected using a single common primer.

The multiplex methods disclosed herein may include the further steps of separating the plurality of templates from the plurality of probes and oligonucleotides, and then amplifying the plurality of templates in a common reaction.

In multiplex embodiments of the disclosed methods, the first and/or second oligonucleotide may usefully include a genotypic label ("barcode") that permits the separate identification of each unique template or product amplified therefrom.

Barcodes may be short nucleic acids having sequence that is designed algorithmically to maximize discrimination on a microarray displaying complements of the respective tags; a 1:1 correspondence as between tag sequence and nucleic acid to which it is appended permits each such nucleic acid to be identified by detection of the bar code uniquely associated therewith. See, e.g., Shoemaker et al., Nature Genet. 14(4): 450 6 (1996); EP 0799897; Fan et al., Genome Res. 10:853 60 (2000); and U.S. Pat. No. 6,150,516, the disclosures of which are incorporated herein by reference in their entireties.

In the methods disclosed herein, a distinct barcode sequence may be included in each species of first and/or each species of second oligonucleotide. In these embodiments, the terminal region of each species of oligonucleotide is distinct in sequence, and can anneal only to a single species of probe. The 1:1 correspondence as between tag sequence and template-appended oligonucleotide thus permits each template or product amplified therefrom to be identified by detection of the bar code uniquely associated therewith.

In one aspect, the number of target polynucleotides or sequences of interest amplified by a method of the invention depends on numerous factors known to those of ordinary skill in the art including, but not limited to, the type of nucleic acid e.g. RNA or DNA, that makes up the target polynucleotides, the quality of the sample, e.g. if and to what degree the target polynucleotides of the sample are degraded, the differences among the selection primer binding sites, the presence or absence of potentially interfering or homologous sequences in the sample, and the like. In one aspect, the number of target polynucleotides amplified in a method of the invention is in the range of from 10 to 100,000; and in another aspect, such number is in the range of from 10 to 1000; and in another aspect, such number is in the range of from 10 to 100, and in another aspect, such number is in the range of from 10 to 50.

The concentrations of probes and/or selection oligonucleotides are a matter of design choice for those of ordinary skill in the art; however, in one aspect, such concentrations may be selected that are equivalent to those used in conventional amplification reactions, such as PCR reactions. Generally, such concentrations are selected following well-known principles of hybridization reactions and PCR primer selections for example, disclosed in the references cited below.

In some aspects assays may be performed on encoded particles as described, for example, in US Patent Publication Nos. 20090149340, 20080038559 (now U.S. Pat. No. 7,745,091) and 20070148599 (now U.S. Pat. No. 7,745,092), which are incorporated herein by reference for all purposes, particularly for methods of making, using and imaging encoded microparticles as disclosed therein. In some aspects, methods that combine hybridization or capturing of an analyte with a purification step may be used. This allows for use of a crude or partially purified sample for hybridization. The hybridization conditions that are used may be similar to those used for proteinase treatment. Additional enzymatic steps may be added to increase specificity over hybridization alone. Enzymatic steps such as ligation or nucleotide extension may be used to increase specificity. In preferred aspects the product of the enzymatic step is covalently attached to the surface of the microparticle so that nonspecific binding can be removed by a stringent wash that includes denaturing conditions. Methods that reduce background relative to signal provide for improved sensitivity and specificity.

Figure 18A:
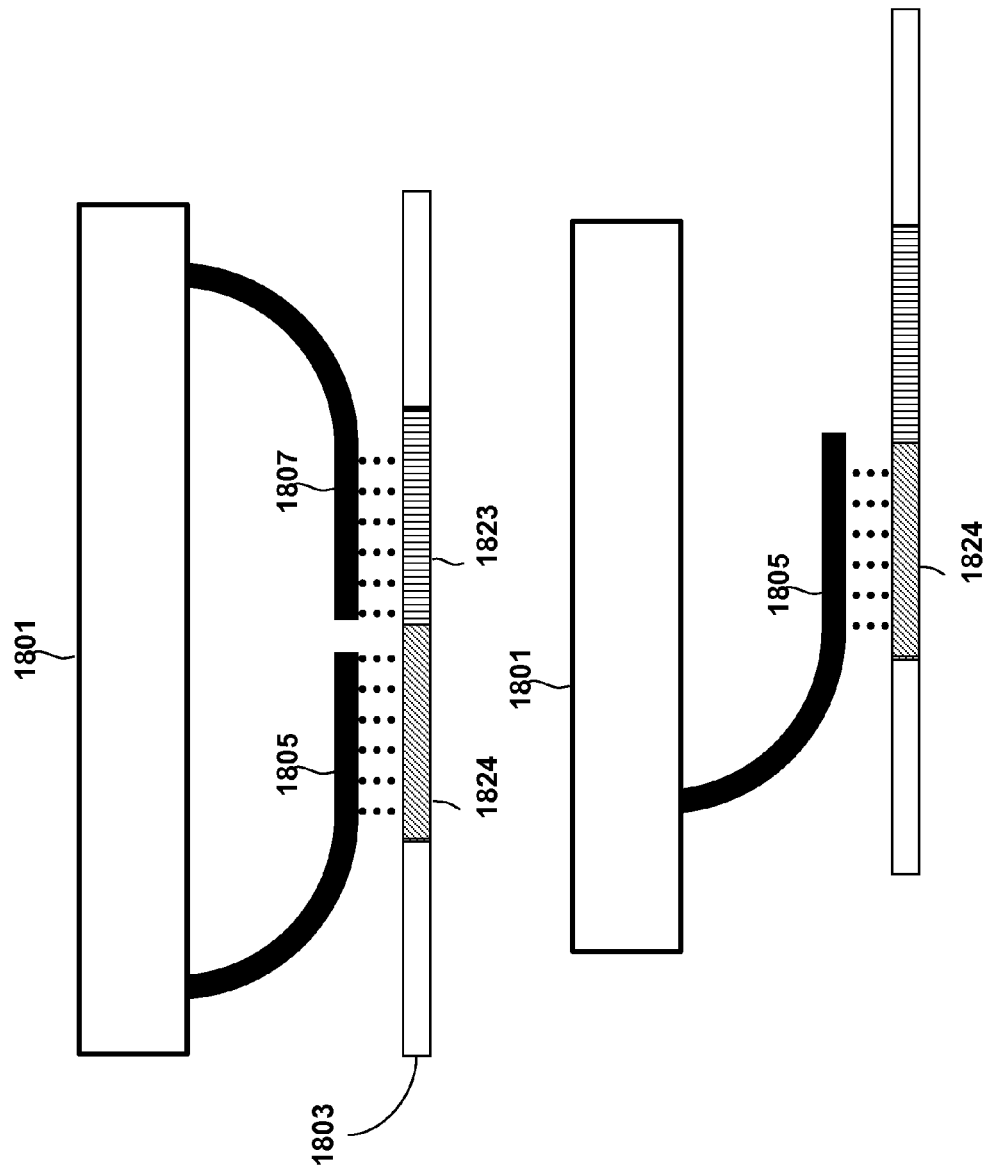
FIG. 18A shows methods for increasing specificity by utilizing the proximity of two probes.

As shown in FIG. 18, the specificity can be improved by using two probes having a close proximity. The microparticle 1801 has two probes each having a region that is complementary to a different region on a target. The microparticle 1803 has a single probe complementary to a single region on the particle. On the left, the length of the probe complementary region is longer than on the right, for example, if the double stranded region of 24 is 20 bases and the double stranded region of 23 is 20 bases, there is 40 bases of complementarity on the left and only 20 on the right. Also, if the two regions are sufficiently close an increase in the stability of both probes is observed due to a stacking effect, for example, it may result in a Tm that is about 5° C. higher. The stringency of the wash can be increased accordingly. Also, the specificity increases if there are two probes each to a different sequence.

Figure 18B:
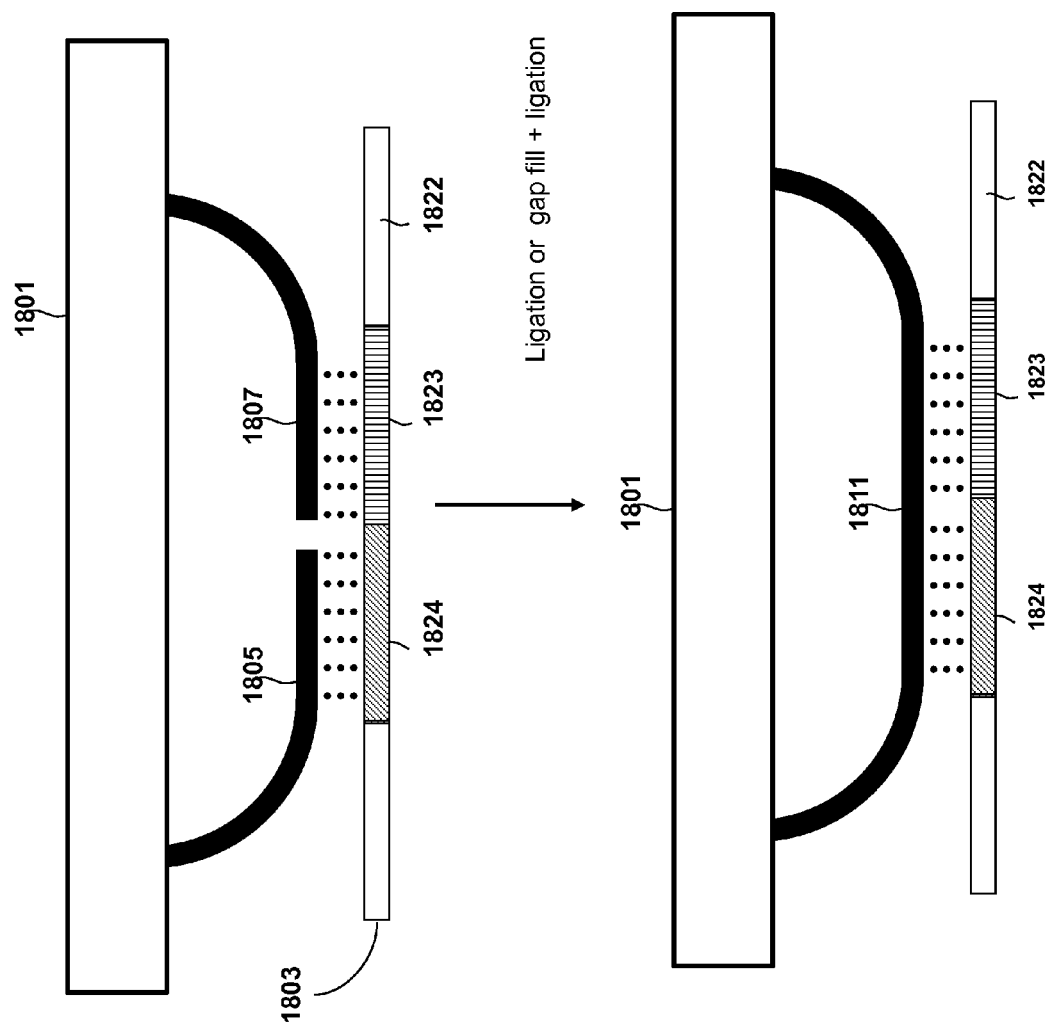
FIG. 18B shows an enzymatic ligation or gap fill followed by ligation of the two probes shown in FIG. 18A.

FIG. 18B shows how two probes in close proximity can be ligated after hybridization, thus increasing the specificity and stability of the resulting probe:target hybrid. The two probes attached to microparticle 1801 are shown hybridized to their corresponding target region on the target 1822. The ends of probes 1805 and 1807 can be ligated together to form a single contiguous probe 1811. In some embodiments the 3' end of one probe is extended to close a gap, if one exists, between the ends of the probes when hybridized with the target. The ligation step increases the Tm, for example, if each probe is a 20 mer before ligation and has a Tm of about 45° C. then after ligation, the probe is now a 40 mer and the Tm would increase to about 65° C.

FIG. 18C illustrates the use of a cleavage step following the ligation step of FIG. 18B, to facilitate labeling or extension. After ligation to form contiguous probe 1811, the probe can be cleaved at cleavage site 1830 to generate a free end and separating 1811 into two pieces, 1811a and 1811b. A label moiety 1833 can be attached to the newly created end. The label can be added, for example, by extension or by ligation.

Figure 18D:
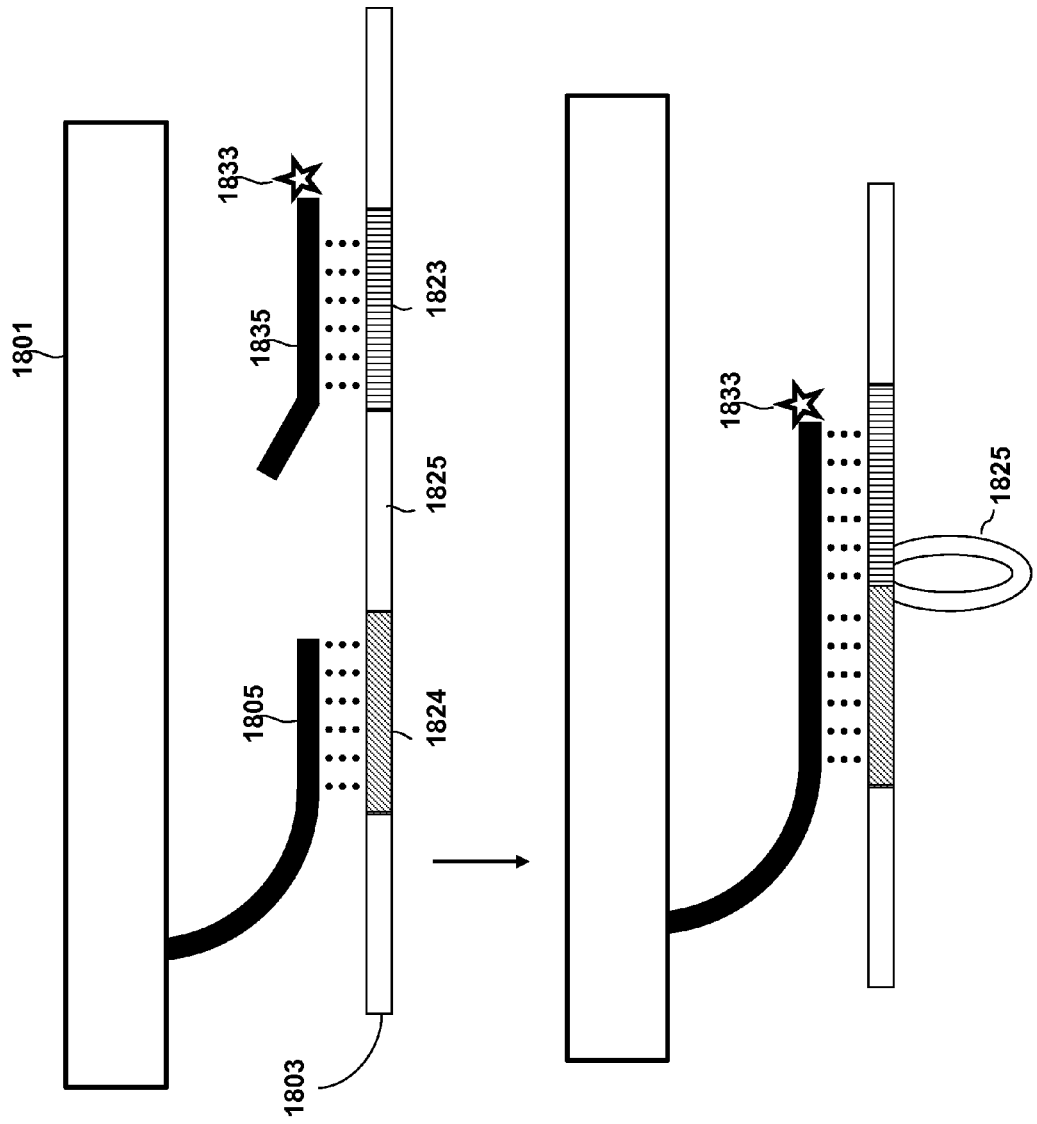
FIG. 18D shows two near proximity probes being ligated through a gap to covalently attach a label from the second probe to the solid support.

FIG. 18D illustrates another method for detection and labeling. A first probe 1805 is covalently attached to the microparticle 1801 and has a region that is complementary to a first target region 1824. There is a second probe 1835 in the solution that is complementary to a second target region 1823 and may be labeled with labeling moiety 1833. The two target regions are separated by a third target region 1825. The two probes can be ligated together to form a ligated probe attached to the microparticle by looping out region 1825 so that the ends of the probes 1805 and 1835 are juxtaposed. As a result, probe 1805 becomes covalently attached to label moiety 1833 and the microparticle is labeled. The joining of probes 1805 and 1835 may also follow extension of probe 1805 through gap 1825. Alternatively, the gap 1825 may be absent and the ends ligated directly. Probe 1835 may or may not have a 5' flap. A flap endonuclease may be used to remove flaps if they are present. For a discussion of methods for using flap endonucleases and methods for removing flap overhangs see, US Patent Pub. 20080199916 (now U.S. Pat. No. 7,682,999), which is incorporated herein by reference in its entirety.

The methods may be used to perform assays, for example, genotyping assays, RNA expression measurement or multiplex PCR, in crude cell lysates. Purification of targets can be combined in a first step with sequence capture. A bead, microparticle or other solid support with a common sequence attached can be hybridized to a capture probe. The sequence specific capture (SSC) probe has a 5' region that is complementary to the common sequence and a 3' region that is complementary to a region of a target. The crude cell lysate is mixed with the bead bound probe and the SSC probe so that the genomic DNA target can hybridize to the complex. The beads may be magnetic to facilitate capture and recovery of the beads with bound target from the lysate. After incubation to allow hybridization of the target the complexes are recovered by recovering the beads. The complexes can be washed to remove protein and non-specifically associated nucleic acids. Multiple different targets can be captured simultaneously by including different SSC probes that are specific for different targets but can have the same common sequence and thus hybridize to beads having the same common nucleic acid attached. After hybridization the SSC can be extended enzymatically form the 3' end using the hybridized target as a template. In a preferred aspect the region of the target used as template contains a region of interest, for example, a SNP, a variant that is associated with a disease, a splice junction or a copy number polymorphism. The extension of the SSC incorporates the complement of the target into the extended SSC. The extended SSC has a common sequence at the 3' end that can be used as a universal priming site. A second target specific oligo can be hybridized to the extended SSC and then extended using the extended SSC as template. Preferably the second target specific oligo hybridizes 3' of the region of interest in the extended SSC so that when the second target specific oligo is extended it will incorporate a copy of that region. The second target specific oligo preferably has a second common sequence at its 5' end and optionally a tag sequence 3' of that and 5' of the target specific sequence. The resulting double stranded product has a target region flanked on one side by a first common sequence and on the other side by optionally a tag sequence and a second common sequence. The first and second common sequences can be used as universal priming sites for PCR amplification of the products. For genotyping the second target specific oligos may be allele specific, having an allele specific base at the 3' end so that when the allele is present the oligonucleotide hybridizes and can be extended but if the allele is not present the oligo hybridizes with a mismatch at the 3' end and will not be efficiently extended. The presence of an amplification product can be detected by hybridization to a tag array after amplification. The method is illustrated in FIG. 19.

In preferred aspects, assay methods may be designed to address a particular market, for example, FFPE, RNA, infectious disease diagnostics, or blood testing. Many of the methods employ common detection and readout platforms and pre-amplification steps are employed in some aspects to amplify material and decrease relative complexity. Reducing the number of operations, particularly those that require addition of material to the reaction is beneficial and the assays should require less than 2 days to observe results, preferably less than 1 day. In general the methods provide mechanisms by which common primers are attached to targets of interest to provide for multiplex amplification using a common primer pair. Common primer PCR can be easily multiplexed to more than 100,000 amplicons compared to multiplex PCR using specific primers, which is typically limited to about 10 to 40 plex.

The above teachings are intended to illustrate the invention and do not by their details limit the scope of the claims of the invention. While preferred illustrative embodiments are described, it will be apparent to one skilled in the art that various changes and modifications may be made therein without departing from the invention, and it is intended in the appended claims to cover all such changes and modifications that fall within the true spirit and scope of the invention.

CONCLUSION

While preferred embodiments have been shown and described herein, it will be obvious to those skilled in the art that such embodiments are provided by way of example only. Numerous variations, changes, and substitutions will now occur to those skilled in the art without departing from the invention. It should be understood that various alternatives to the embodiments of the invention described herein may be employed in practicing the invention. It is intended that the following claims define the scope of the invention and that methods and structures within the scope of these claims and their equivalents be covered thereby. All cited references, including patent and non-patent literature, are incorporated herein by reference in their entireties for all purposes and particularly to disclose and describe the methods or materials in connection with which the publications are cited.

I claim:

1. A method for amplifying a plurality of target nucleic acids comprising:
   (a) obtaining a plurality of capture probes comprising a capture probe for each target nucleic acid in the plurality of target nucleic acids, wherein each capture probe comprises a first 3' region that is complementary to a target nucleic acid in the plurality of target nucleic acids, a second region that has a first priming sequence, and optionally a third region between said first and second regions that comprises a tag sequence;
   (b) mixing the capture probes with a nucleic acid sample that includes the target nucleic acids under conditions that allow hybridization of the capture probes to form duplexes between the capture probes and the target nucleic acids;
   (c) extending the capture probes from the 3' end with a polymerase using the target nucleic acids as template to form extended capture probes that comprise a newly added region that is complementary to the target nucleic acid;
   (d) hybridizing a splint probe, comprising a target complementary region and a 5' overhang region, to a portion of the newly added region to form a duplex between the target complementary region of the splint probe and a portion of the newly added region leaving a 3' region of the extended capture probe single stranded, wherein the 3' region includes the 3' end of the extended capture probe;
   (e) degrading the 3' region of the extended capture probes with a single strand specific 3' endonuclease;
   (f) forming a duplex between the 5' overhang region of the splint probe and a ligatable sequence comprising a region that is complementary to a region of the splint probe and a second priming sequence, and ligating said ligatable sequence to the 3' end of the extended capture probe to form a ligated product; and
   (g) amplifying the ligated product using the first and second priming regions.

2. The method of claim 1 wherein said ligatable sequence is an oligonucleotide having a 5' region that is complementary to a region of the splint probe and a 3' region that comprises the second priming sequence.

3. The method of claim 1 wherein the capture probe comprises from the 3' end, a template complementary region, the first priming sequence, wherein the first priming sequence is common to all capture probes, a cleavage site, the second priming sequence, wherein the second priming sequence is common to all capture probes, the tag sequence, and a region that is complementary to the overhang region of the splint probe, wherein step (f) comprises:
   forming a duplex between the overhang region of the splint probe and the region that is complementary to the overhang region of the splint probe, thereby bringing the 5' end of the extended capture probe so that it is adjacent to the 3' end of the extended capture probe; and
   ligating the 5' end of the extended capture probe to the 3' end of the extended capture probe, thereby forming a closed circle prior to step (g).

4. The method of claim 3 further comprising cleaving the closed circle at the cleavage site in the capture probe prior to step (g).

5. The method of claim 2 wherein the capture probes comprise in the 5' to 3' direction, a first target complementary region, the first priming sequence, wherein the first priming sequence is common to all capture probes, the tag sequence and a second target complementary region.

6. The method of claim 1 wherein the splint probe comprises the target complementary region, the 5' overhang region, and thee ligatable sequence comprising a region that is complementary to another region of the splint probe and thee second priming sequence, and wherein step (f) comprises:
   forming an intra-molecular loop between the 5' overhang region and the ligatable sequence of the splint probe, so that the 5' end of the splint probe is adjacent to the 3' end of the extended capture probe; and
   ligating the 5' end of the splint probe to the 3' end of the extended capture probe prior to step (g).

7. The method of claim 1 wherein the capture probe comprises a plurality of uracil residues, the method further comprising degrading the extended capture probe after making at least one complimentary copy.

8. The method of claim 1 wherein the splint probe comprises a plurality of uracil residues, the method further comprising degrading the extended capture probe after making at least one complimentary copy.

9. The method of claim 7 wherein the splint probe comprises a plurality of uracil residues.

* * * * *